US011547753B2

(12) United States Patent
Müller et al.

(10) Patent No.: US 11,547,753 B2
(45) Date of Patent: Jan. 10, 2023

(54) CUTANEOUS PAPILLOMA VIRUS VACCINE

(71) Applicant: Deutsches Krebsforschungszentrum, Heidelberg (DE)

(72) Inventors: Martin Müller, Neckargemünd (DE); Simone Ottonello, Heidelberg (DE); Angelo Bolchi, Heidelberg (DE); Filipe Mariz, Heidelberg (DE); Xueer Zhao, Dossenheim (DE); Kathrin Balz, Gießen (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 16/651,338

(22) PCT Filed: Oct. 1, 2018

(86) PCT No.: PCT/EP2018/076651
§ 371 (c)(1),
(2) Date: Mar. 26, 2020

(87) PCT Pub. No.: WO2019/063841
PCT Pub. Date: Apr. 4, 2019

(65) Prior Publication Data
US 2020/0261563 A1    Aug. 20, 2020

(30) Foreign Application Priority Data

Sep. 29, 2017  (EP) ..................................... 17194145

(51) Int. Cl.
| | | |
|---|---|---|
| *C07K 14/025* | (2006.01) | |
| *A61K 39/12* | (2006.01) | |
| *A61K 39/295* | (2006.01) | |
| *A61P 31/20* | (2006.01) | |
| *A61P 37/06* | (2006.01) | |
| *C12N 7/00* | (2006.01) | |
| *A61K 39/00* | (2006.01) | |

(52) U.S. Cl.
CPC .............. *A61K 39/12* (2013.01); *A61P 31/20* (2018.01); *A61P 37/06* (2018.01); *C07K 14/025* (2013.01); *C12N 7/00* (2013.01); *A61K 2039/55566* (2013.01); *A61K 2039/575* (2013.01)

(58) Field of Classification Search
None
See application file for complete search history.

(56) References Cited

U.S. PATENT DOCUMENTS 9,303,082 B2 *  4/2016  Mueller ................ A61K 39/385
2010/0297144 A1 * 11/2010  Roden ..................... A61K 39/12
424/159.1

FOREIGN PATENT DOCUMENTS

| EP | 2 199 301 A1 | 6/2010 |
|---|---|---|
| WO | WO 2007/062819 A2 | 6/2007 |
| WO | WO 2009/059325 A2 | 5/2009 |
| WO | WO 2010//070052 A2 | 6/2010 |
| WO | WO 2011/151335 A1 | 12/2011 |
| WO | WO 2013/106525 A1 | 7/2013 |
| WO | WO 2015/068101 A | 5/2015 |
| WO | WO 2015/068101 A1 * | 5/2015 |

OTHER PUBLICATIONS

GenBank: AYV61480.1. L2 [Human papillomavirus type 16], Dated Nov. 19, 2018.*
Chan et al. Phylogenetic Analysis of 48 Papillomavirus Types and 28 Subtypes and Variants: a Showcase for the Molecular Evolution of DNA Viruses. Journal of Virology, Oct. 1992, vol. 66, No. 10, p. 5714-5725.*
Jagu et al., Optimization of Multimeric Human Papillomavirus L2 Vaccines. PLoS ONE , 2013, 8(1): e55538.*
Sun et al. Salt-Dependent Aggregation and Assembly of E coli-Expressed Ferritin. Dose-Response: An International Journal. Jan.-Mar. 2016:1-6.*
Choi et al. Effective Delivery of Antigen—Encapsulin Nanoparticle Fusions to Dendritic Cells Leads to Antigen-Specific Cytotoxic T Cell Activation and Tumor Rejection. ACS Nano 2016, 10, 7339-7350.*
Kasyutich et al. Silver Ion Incorporation and Nanoparticle Formation inside the Cavity of Pyrococcus furiosus Ferritin: Structural and Size-Distribution Analyses. J. Am. Chem. Soc. 2010, 132, 3621-3627.*
Akita et al. The Crystal Structure of a Virus-like Particle from the Hyperthermophilic Archaeon Pyrococcus furiosus Provides Insight into the Evolution of Viruses. J. Mol. Biol. (2007) 368, 1469-1483.*
Wiryaman et al. Recent advances in the structural biology of encapsulin bacterial nanocompartments. Journal of Structural Biology: X 6 (2022) 100062.*
Minhinnick et al. A first-in-human phase 1 trial to evaluate the safety andimmunogenicity of the candidate tuberculosis vaccine MVA85A-IMX313, administered to BCG-vaccinated adults. Vcaccine. 2016, 34:1412-1421.*
Schmiedeskamp, et al., "Human Papillomavirus Vaccines," *Annals of Pharmacotherapy*, vol. 40, pp. 1344-1352 (Jul./Aug. 2006).
Roden et al., How will HPV Vaccines Affect Cervical cancer?), *Nat Rev Cancer*, vol. 6:, pp. 753-763 (2006).

(Continued)

*Primary Examiner* — Nianxiang Zou
(74) *Attorney, Agent, or Firm* — Foley & Lardner LLP

(57) ABSTRACT

The present invention relates to an immunogenic polypeptide comprising a multitude of papillomavirus (PV) L2 N-terminal peptides corresponding to amino acids 20 to 50 of the L2 polypeptide of HPV16, wherein said HPV L2 N-terminal peptides are L2 N-terminal peptides from at least four different cutaneous HPV genotypes; and to the aforesaid immunogenic polypeptide for use in medicine and for use in vaccination of a subject against cutaneous HPV infection and/or mucosal HPV infection. The present invention further relates to a polynucleotide encoding the aforesaid immunogenic polypeptide and to vectors, host cells, methods for producing an antibody, as well as antibodies related thereto.

29 Claims, 7 Drawing Sheets

Figure 1:
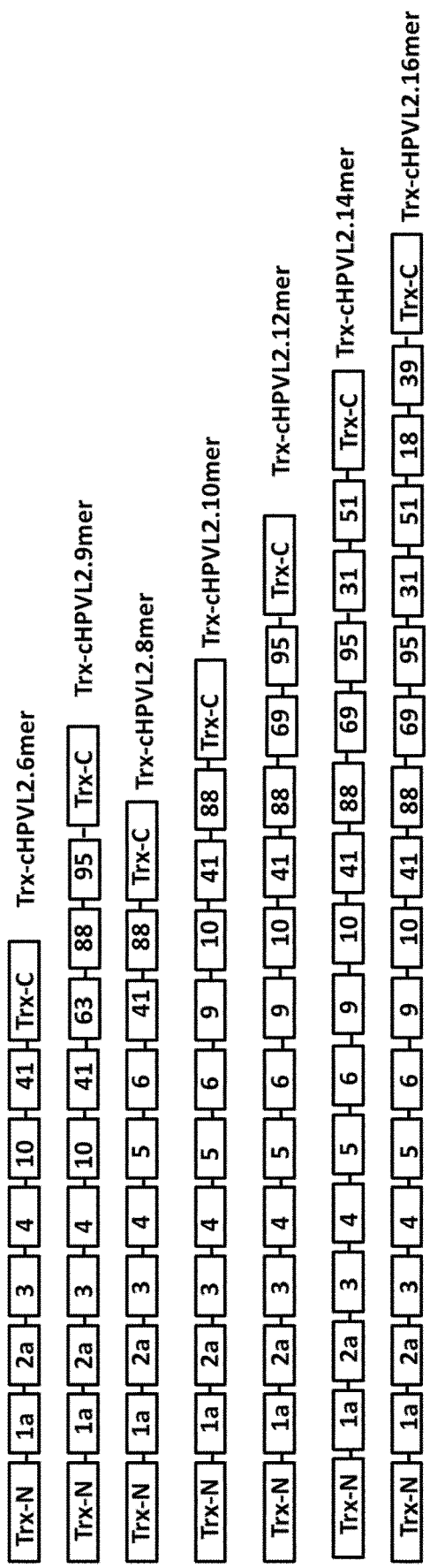

Specification includes a Sequence Listing.

(56) References Cited

OTHER PUBLICATIONS

Giroglou et al., "Immunological Analyses of Human Papillomavirus Capsids," *Vaccine*, vol. 19, pp. 1783-1793 (2001).
Moretto et al., "Conformation-sensitive Antibodies against Alzheimer Amyloid-ß by Immunization with a Thioredoxin-constrained B-cell Epitope Peptide," J. Biol. Chem., vol. 282, pp. 11436-11445 (2007).
Canali, et al., "A high-performance thioredoxin-based scaffold for peptide immunogen construction: proof-of-concept testing with a human papillomavirus epitope," (2014), Scientific Reports 4, Art. No 4729:1 (2014).
Zur Hausen, "Cervical Carcinoma and Human Papillomavirus: On the Road to Preventing a Major Human Cancer," J. Natl. Cancer Inst., vol. 93, pp. 252-253 (2001).
Van Doorslaer, et al., "Papillomaviruses: evolution, Linnaean Taxonomy and Current Nomenclature," Trends *Microbiol.*, vol. 19, pp. 49-50; author reply 50-41 (2011).
Bernard, et al., "Classification of Papillomaviruses (PVs) based on 189 PV types and proposal of taxonomic amendments," *Virology*, vol. 401, pp. 70-79 (2010).
Munoz et al., "Against which Human Papillomavirus types shall we Vaccinate and Screen? The International Perspective," *Int. J. Cancer*, vol. 111, pp. 278-285 (2004).
Pfister, "Chapters: Human Papillomavirus and Skin Cancer," J. Natl. Cancer Inst. Monographs, pp. 52-56 (2003).
Howley et al., "Beta Genus Papillomaviruses and Skin Cancer," Virology, pp. 479-480, 290-296 (2015).
Wieland et al., "Human papillomavirus and Immunosuppression," *Curr Probl Dermatol.*, vol. 45, pp. 154-165 (2014).
Egawa, et al., "The Low-Risk Papillomaviruses," *Virus Research*, vol. 231, pp. 119-127 (2017).
Day et al.,"A Human Papillomavirus (HPV) In Vitro Neutralization Assay That Recapitulates the In Vitro Process of Infection Provides a Sensitive Measure of HPV L2 Infection-Inhibiting Antibodies," *Clinical and Vaccine Immunology*, vol. 19, No. 7, pp. 1075-1082 (2012).
Spagnoli, et al., "Broadly neutralizing antiviral responses induced by a singlemolecule HPV vaccine based on thermostable thioredoxin-L2 multiepitope nanoparticles," *Scientific Reports*, 13 pages (Dec. 2017).
Pouyanfard, et al., "Minor Capsid Protein L2 Polytope Induces Broad Protection against Oncogenic and Mucosal Human Papillomaviruses," *Journal of Virology*, vol. 92, No. 4, 18 pages (Feb. 2018).
Seitz et al., Influence of Oxidation and Multimerization on the Immunogenicity of a Thioredoxin-L2 Prophylactic Papillomavirus Vaccine, Clin. Vaccine Immunol., vol. 20, pp. 1061-1069 (2013).
Wang et al.,"Production of Furin-Cleaved Papillomavirus Pseudovirions and Their Use for In Vitro Neutralization Assays of L1- or L2-Specific Antibodies," Curr Protoc Microbiol, vol. 38, 14B.5.1-14B.5.26 (2015).
Jagu et al., "Phylogenetic Considerations in Designing a Broadly Protective Multimeric L2 Vaccine," *Journal of Virology*, vol. 87, No. 11, pp. 6127-6136 (Mar. 2013).
Skerra et al., "Alternative non-antibody scaffolds for molecular recognition", *Current Opinion Biotechnology*, vol. 18, No. 4, Sep. 14, 2007 (Sep. 14, 2007), pp. 295-304 (Sep. 2007).
International Search Report and Written Opinion issued in co-pending International Patent Application No. PCT/EP2018/076651, completed Nov. 5, 2018.

\* cited by examiner

CUTANEOUS PAPILLOMA VIRUS VACCINE

CROSS-REFERENCE TO RELATED APPLICATIONS

This application is the U.S. National Stage of International Patent Application No. PCT/EP2018/076651, filed Oct. 1, 2018, which claims priority from European Patent Application No. 17194145.3, filed Sep. 29, 2017. The contents of these applications are incorporated herein by reference in their entirety.

SEQUENCE LISTING

The present application contains a Sequence Listing which has been filed electronically in ASCII format and is hereby incorporated by reference in its entirety.

The present invention relates to an immunogenic polypeptide comprising a multitude of papillomavirus (PV) L2 N-terminal peptides corresponding to amino acids 20 to 50 of the L2 polypeptide of HPV16, wherein said HPV L2 N-terminal peptides are L2 N-terminal peptides from at least four different cutaneous HPV genotypes; and to the aforesaid immunogenic polypeptide for use in medicine and for use in vaccination of a subject against cutaneous HPV infection and/or mucosal HPV infection. The present invention further relates to a polynucleotide encoding the aforesaid immunogenic polypeptide and to vectors, host cells, methods for producing an antibody, as well as antibodies related thereto.

HPV vaccines as yet have been produced only for high-risk mucosal HPV genotypes. The first two anti-HPV vaccines for the prophylaxis of cervical cancer have been licensed recently by Merck (Gardasil™) and GlaxoSmithKline (Cervarix™) (Schmiedeskamp et al, (2006), Ann Pharmacother, 40: 1344-1352). Both vaccines rely on the major capsid protein L1 in the form of virus-like particles (VLPs) as antigen (Roden et al., (2006), Nat Rev Cancer, 6: 753-763); they protect against the HPV types from which the L1-VLPs were derived, yet are largely ineffective against all but the most closely related HPV types. The limited cross-protective capacity of L1-based vaccines, which is the main reason for the continuing effort toward the development of improved vaccination strategies, likely reflects the HPV type specificity of L1 neutralizing epitopes (Giroglou et al., (2001), Vaccine, 19: 1783-1793).

A recently developed alternative strategy for increasing peptide immunogenicity relies on the use of thioredoxin (Trx) as a scaffold protein with the ability to constrain the structure of single-copy as well as multimeric (tandemly repeated) peptide epitopes inserted within its surface-exposed active site loop (Moretto et al. (2007), J Biol Chem, 282, 11436-11445). This strategy has also been used to present HPV L2 peptides for immunization (WO 2010/070052). For thioredoxin as scaffold protein, it was found that by using Trx variants from Archaebacteria, induction of anti-host thioredoxin antibodies can be significantly reduced (Canali et al. (2014), Scientific Reports 4, Art. No 4729:1).

Infections with Human papillomavirus (HPV) are a worldwide health challenge, particularly in resource-limited regions (H. zur Hausen, J Natl Cancer Inst 93, 252-253 (2001)). HPV-related diseases are pre-malignancies or overt malignancies of the skin and mucosal surfaces and are an important personal and public health problem causing physical, mental, sexual and financial detriments. The World Health Organization estimates that there are approximately 14 million new HPV infections each year. Currently, ~200 different HPV genotypes are described with varying tropism for anogenital mucosa or skin (K. Van Doorslaer et al., Trends Microbiol 19, 49-50; author reply 50-41 (2011); H. U. Bernard et al., Virology 401, 70-79 (2010)). A subgroup of about 15 HPV, all belonging to the alpha papillomaviruses (high risk, HR-HPV) are causatively associated with invasive anogenital cancer, in particular cervical carcinomas (N. Munoz et al., Int J Cancer 111, 278-285 (2004)). In addition, some of the HR-HPV are found in tumors of the oropharynx. Most women become infected with one or more of the HR-HPV but less than 1% (developing countries) develop cervical cancer. Thus, the majority of women are able to control the HR-HPV infections which are mostly short lived. But in some women a persistent infection is established, and this is the main risk factor for HPV associated cancer.

The skin and mucosa of all individuals constantly harbor a plethora of HPV which, because being rarely associated with malignant disease, are considered low risk HPV (LR-HPV). A number of these are found in common, plantar, or flat warts. Beta papillomaviruses have been attributed as commensals, because they can be detected frequently in skin swaps or hair bulbs without causing any visible lesions or warts (H. Pfister, J Natl Cancer Inst Monogr, 52-56 (2003)). Skin warts are common in children but evidently lesions are rarely found in healthy adults. The most frequent HPV associated lesions in sexually active persons are genital warts, skin warts are found in less than 2% of adults but are more frequent in children. Taken together, there is an obvious evolution driven adaptation between LR-HPV and the host. While healthy individuals can control the constant exposure to LR-HPV well, this, however, is dysregulated in situations of immune suppression: In organ transplant recipients (OTRs) the most important cutaneous complications are development of warts and squamous cell carcinomas, both associated with HPV infections, although a clear causal role is only established for the first (P. M. Howley et al., Virology 479-480, 290-296 (2015); U. Wieland et al., Curr Probl Dermatol 45, 154-165 (2014)). Likewise, HIV+ individuals are also not able to efficiently control HPV infections, although there are significant differences in the disease spectrum compared to OTRs.

Skin warts are found in a small fraction of healthy adults and these are caused by HPV from different genera. While β-papillomaviruses are among the most abundant HPV in the skin, they do not cause lesions in healthy individuals. In OTRs the number of skin warts are constantly rising corresponding with the duration of the iatrogenic immune suppression. Similar observations are being made in other immune compromised individuals, e.g. HIV+. Five years after transplantation up to 92% of the OTRs are suffering from skin warts. Skin warts constitute a significant burden and reduced quality of life in OTRs due to their confluent occurrence at multiple body sites. The warts in OTRs usually do not regress spontaneously and therefore require repeated and costly treatment which, however, can only alleviate the symptoms and does not provide a lasting cure.

Invasive tumors are the main cause of death in OTRs and the most frequent type of tumor is squamous cell carcinoma (SCC) of the skin. SCC develops much more frequently in OTRs and the tumors are more aggressive. In OTRs SCC have a 30% chance to metastasize compared to a 3% risk in immune competent individuals. Skin SCC and actinic keratosis, a precursor lesion of SCC, have been associated with HPV infections in a large number of studies (Wieland et al., loc. cit.). Thus, although being regarded as low-risk infectious agents, the impact of cutaneous HPV infection on human health is substantial, in particular in immunocompromised patients (Egawa & Doorbar (2017), Virus Res 231: 119).

There is, thus, a need in the art for improved means and methods for vaccination against HPV, in particular cutaneous HPV, and in particular for immunogenic polypeptides that are highly immunogenic and allow for a cross-neutralization of various HPV genotypes without the drawbacks as referred to above. The technical problem underlying the present invention can be seen as the provision of means and methods for complying with the aforementioned needs. The technical problem is solved by the embodiments characterized in the claims and herein below.

Accordingly, the present invention relates to an immunogenic polypeptide comprising a multitude of human papillomavirus (HPV) L2 N-terminal peptides corresponding to amino acids 20 to 50 of the L2 polypeptide of HPV16, wherein said HPV L2 N-terminal peptides are L2 N-terminal peptides from at least four, preferably at least five, more preferably at least 6, different cutaneous HPV genotypes.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

Moreover, if not otherwise indicated, the term "about" relates to the indicated value with the commonly accepted technical precision in the relevant field, preferably relates to the indicated value±20%, more preferably ±10%, most preferably ±5%. Further, the term "essentially" indicates that deviations having influence on the indicated result or use are absent, i.e. potential deviations do not cause the indicated result to deviate by more than ±20%, more preferably ±10%, most preferably ±5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 1%, most preferably less than 0.1% by weight of non-specified component(s). In the context of nucleic acid sequences, the term "essentially identical" indicates a % identity value of at least 80%, preferably at least 90%, more preferably at least 98%, most preferably at least 99%. As will be understood, the term essentially identical includes 100% identity. The aforesaid applies to the term "essentially complementary" mutatis mutandis.

The term "immunogenic polypeptide", as used herein, relates to a, preferably non-naturally occurring, polypeptide comprising a multitude of L2 N-terminal sequences as specified herein. The immunogenic polypeptide referred to herein comprises at least a multitude of human papillomavirus (HPV) L2 N-terminal peptides as specified herein. As specified herein below, the immunogenic polypeptide may comprise further domains, like, preferably, scaffold polypeptides, e.g. thioredoxin, immune enhancers, oligomerization domains, and the like. Preferably, said domains are linked by non-covalent bonds and have a dissociation constant of at most $10^{-6}$ mol/l, more preferably of at most $10^{-7}$ mol/l, most preferably at most $10^{-8}$ mol/l. More preferably, at least two domains are covalently connected, preferably by a peptide bond. Most preferably, all domains of the immunogenic polypeptide are covalently connected, preferably by peptide bonds; i.e. preferably, the immunogenic polypeptide is a polypeptide having a contiguous chain of amino acids. Thus, preferably, the immunogenic polypeptide is encoded by a single open reading frame. Preferably, the immunogenic polypeptide has the biological function of being an immunogenic polypeptide, inducing a humoral and/or a cellular immune response in a subject, more preferably inducing a humoral immune response in a subject. Most preferably, the immunogenic polypeptide has the biological function of inducing immunity to at least one, more preferably at least three, still more preferably at least eight, most preferably at least ten HPV genotypes.

Preferably, the term immunogenic polypeptide includes variants of the specific immunogenic polypeptides described herein. As used herein, the term "polypeptide variant" relates to any chemical molecule comprising at least the polypeptides as specified herein, having the indicated activity, but differing in structure from said polypeptide indicated herein. Preferably, the polypeptide variant comprises a peptide having an amino acid sequence corresponding to an amino acid sequence of from 25 to 500, more preferably of from 30 to 300, most preferably, of from 35 to 150 consecutive amino acids comprised in a polypeptide as specified herein. Moreover, also encompassed are further polypeptide variants of the aforementioned polypeptides. Such polypeptide variants have at least the same essential biological activity as the specific polypeptides. Moreover, it is to be understood that a polypeptide variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the full length of the peptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants referred to above may be derived from allelic variants or any other species specific homologs, paralogs, or orthologs. Moreover, the polypeptide variants referred to herein include fragments of the specific polypeptides or the aforementioned types of polypeptide variants as long as these fragments and/or variants have the biological activity as referred to above. Such fragments may be or be derived from, e.g., degradation products or splice variants of the polypeptides. Further included are variants which differ due to posttranslational modifications such as phosphorylation, glycosylation, ubiquitinylation, sumoylation, or myristylation, by including non-natural amino acids, and/or by being peptidomimetics. Moreover, variants of the immunogenic polypeptide of the present invention, preferably, include variants wherein at least one domain is a variant of a domain described herein.

As used herein, the term "papillomavirus" (PV) relates to a DNA virus from the papillomaviridae family of viruses that infects the skin and mucous membranes of mammals, preferably livestock, more preferably cattle and horses, most preferably humans. Thus, the papillomavirus preferably is a human papillomavirus (HPV). Preferably, the PV, preferably HPV, is a PV infecting the skin, i.e. preferably, is a cutaneous PV type, more preferably a cutaneous HPV. More preferably, the cutaneous HPV is HPV genotype 1a, 2a, 3, 4, 5, 6, 9, 10, 41, 69, 88, or 95. As is understood by the skilled person, the cutaneous HPV preferably is a Low-Risk-HPV (LR-HPV). In some embodiments, the PV is a mucosal PV, preferably a mucosal HPV. Preferably, mucosal HPVs are High-risk HPV genotypes (HR-HPVs), which are the main cause for the development of cervical cancer. Thus, preferably, mucosal HPVs are HPV 16 and/or 18; more preferably are HPV 11, 16, 18, 31, 35, 39, 51, 58, and 73.

The term "L2 N-terminal peptide" refers to a peptide having an amino acid sequence of a peptide occurring in the N-terminus of a HPV L2 polypeptide. HPV L2 polypeptides are known in the art; preferred HPV L2 polypeptides are the L2 polypeptides of HPV1a, preferably having the amino acid sequence of SEQ ID NO: 1, HPV2a, preferably having the amino acid sequence of SEQ ID NO: 2, HPV3, preferably having the amino acid sequence of SEQ ID NO: 3, HPV4, preferably having the amino acid sequence of SEQ ID NO: 4, HPV5, preferably having the amino acid sequence of SEQ ID NO: 5, HPV6, preferably having the amino acid sequence of SEQ ID NO: 6, HPV9, preferably having the amino acid sequence of SEQ ID NO: 7, HPV10, preferably having the amino acid sequence of SEQ ID NO: 8, HPV18, preferably having the amino acid sequence of SEQ ID NO: 9, HPV31, preferably having the amino acid sequence of SEQ ID NO: 10, HPV39, preferably having the amino acid sequence of SEQ ID NO: 11, HPV41, preferably having the amino acid sequence of SEQ ID NO: 12, HPV51, preferably having the amino acid sequence of SEQ ID NO: 13, HPV63, preferably having the amino acid sequence of SEQ ID NO: 14, HPV69, preferably having the amino acid sequence of SEQ ID NO: 15, HPV88, preferably having the amino acid sequence of SEQ ID NO: 16, and HPV95, preferably having the amino acid sequence of SEQ ID NO: 17. The full-length L2 polypeptide is one of the two capsid proteins of papillomaviruses and is also referred to as minor capsid protein. Together with the major capsid protein, L1, the full-length L2 polypeptide forms viral capsids. The L2 N-terminal peptide, in the context of the present invention corresponds to amino acids 20 to 50, preferably amino acids 20 to 38 of the L2 polypeptide of an HPV L2 polypeptide. As will be understood by the skilled person, the L2 polypeptides of the various HPV genotypes are not necessarily exactly colinear due to sequence variations, although preferred immunogenic epitopes share a similar sequence. Thus, for amino acid numbering, reference is frequently made to amino acid positions corresponding to the positions of corresponding amino acids in the HPV16 L2 amino acid sequence. Thus, preferably, the L2 N-terminal peptide, in the context of the present invention, corresponds to amino acids 20 to 50, preferably amino acids 20 to 38 of the L2 polypeptide of HPV16. Preferred L2 N-terminal peptides corresponding to amino acids 20 to 50 of the L2 polypeptide of HPV16 are those derivable from the amino acid sequences of SEQ ID NOs: 1 to 17. Preferred L2 N-terminal peptides corresponding to amino acids 20 to 38 of the L2 polypeptide of HPV16 are those having the amino acid sequences of SEQ ID NOs: 18 to 34, i.e. those of HPV1a (SEQ ID NO: 18), HPV2a (SEQ ID NO: 19), HPV3 (SEQ ID NO: 20), HPV4 (SEQ ID NO: 21), HPV5 (SEQ ID NO: 22), HPV6 (SEQ ID NO: 23), HPV9 (SEQ ID NO: 24), HPV10 (SEQ ID NO: 25), HPV18 (SEQ ID NO: 26), HPV31 (SEQ ID NO: 27), HPV39 (SEQ ID NO: 28), HPV41 (SEQ ID NO: 29), HPV51 (SEQ ID NO: 30), HPV63 (SEQ ID NO: 31), HPV69 (SEQ ID NO: 32), HPV88 (SEQ ID NO: 33), and HPV95 (SEQ ID NO: 34).

Preferably, the term L2 N-terminal peptide includes variants of the specific N2-terminal peptides as specified herein above. More preferably, variants of the N2-terminal peptides are variants comprising at most two, preferably at most one amino acid deletion(s), insertion(s) and/or substitution(s) per HPV L2 N-terminal peptide. More preferably, variants of the N2-terminal peptides are variants comprising at most two, preferably at most one amino acid substitution(s), preferably conservative substitution(s), per HPV L2 N-terminal peptide.

The term "multitude of HPV L2 N-terminal peptides" relates to a number of at least 4, preferably at least 5, more preferably at least 6 HPV L2 N-terminal peptides. Preferably, said multitude is a number of from 5 to 20, preferably of from 6 to 19, most preferably of from 6 to 16 HPV L2 N-terminal peptides. Preferably, the immunogenic polypeptide comprises three copies, more preferably two copies, most preferably one copy of each of said HPV L2 N-terminal peptides. Preferably, at least two, more preferably at least five, even more preferably at least eight HPV L2 N-terminal peptides comprised in said immunogenic polypeptide are non-identical. Most preferably, the multitude of HPV L2

N-terminal peptides consists of non-identical HPV L2 N-terminal peptides, i.e., preferably, comprises HPV L2 N-terminal peptides which are all mutually different from each other. Thus, preferably, the HPV L2 N-terminal peptides in said immunogenic polypeptide are L2 N-terminal peptides from at least two, more preferably at least four, even more preferably at least five, most preferably at least six different HPV genotypes. Preferably, the HPV L2 N-terminal peptides in said immunogenic polypeptide comprise L2 N-terminal peptides selected from L2 N-terminal peptides from HPV genotypes 1a, 2a, 3, and 4 or variants thereof comprising at most two, preferably at most one amino acid substitution(s) per HPV L2 N-terminal peptide. More preferably, the HPV L2 N-terminal peptides in said immunogenic polypeptide comprise L2 N-terminal peptides selected from L2 N-terminal peptides from HPV genotypes 1a, 2a, 3, and 4. Still more preferably, the HPV L2 N-terminal peptides further comprise L2 N-terminal peptides of cutaneous HPV genotypes of at least one of HPV 5, 6, 9, 10, 41, 63, 69, 88, and 95 or variants thereof comprising at most two, preferably at most one amino acid substitution(s) per HPV L2 N-terminal peptide. Most preferably, the HPV L2 N-terminal peptides further comprise L2 N-terminal peptides of cutaneous HPV genotypes of at least one of HPV 5, 6, 9, 10, 41, 63, 69, 88, and 95. Preferably, the immunogenic polypeptide further comprises HPV L2 N-terminal peptides from at least one, preferably at least two, even more preferably at least three, most preferably at least four mucosal HPV genotypes. More preferably, in this case the mucosal HPV genotypes are selected from HPV 18, 31, 39, and 51.

Thus, preferably, the HPV L2 N-terminal peptides comprise L2 N-terminal peptides of (i) cutaneous HPV genotypes 1a, 2a, 3, 4, 10, and 63 or variants thereof comprising at most two, preferably at most one amino acid substitution(s) per HPV L2 N-terminal peptide; (ii) cutaneous HPV genotypes 1a, 2a, 3, 4, 10, 41, 63, 88, and 95 or variants thereof comprising at most two, preferably at most one amino acid substitution(s) per HPV L2 N-terminal peptide; (iii) cutaneous HPV genotypes 1a, 2a, 3, 4, 5, 6, 41, 88 or variants thereof comprising at most two, preferably at most one amino acid substitution(s) per HPV L2 N-terminal peptide; (iv) cutaneous HPV genotypes 1a, 2a, 3, 4, 5, 6, 9, 10, 41, 88 or variants thereof comprising at most two, preferably at most one amino acid substitution(s) per HPV L2 N-terminal peptide; (v) cutaneous HPV genotypes 1a, 2a, 3, 4, 5, 6, 9, 10, 41, 69, 88, and 95 or variants thereof comprising at most two, preferably at most one amino acid substitution(s) per HPV L2 N-terminal peptide; (vi) HPV genotypes 1a, 2a, 3, 4, 5, 6, 9, 10, 31, 41, 51, 69, 88, and 95 or variants thereof comprising at most two, preferably at most one amino acid substitution(s) per HPV L2 N-terminal peptide; or (vii) HPV genotypes 1a, 2a, 3, 4, 5, 6, 9, 10, 18, 31, 39, 41, 51, 69, 88, and 95 or variants thereof comprising at most two, preferably at most one amino acid substitution(s) per HPV L2 N-terminal peptide. More preferably, said HPV L2 N-terminal peptides comprise L2 N-terminal peptides of (i) cutaneous HPV genotypes 1a, 2a, 3, 4, 10, and 63; (ii) cutaneous HPV genotypes 1a, 2a, 3, 4, 10, 41, 63, 88, and 95; (iii) cutaneous HPV genotypes 1a, 2a, 3, 4, 5, 6, 41, 88; (iv) cutaneous HPV genotypes 1a, 2a, 3, 4, 5, 6, 9, 10, 41, 88; (v) cutaneous HPV genotypes 1a, 2a, 3, 4, 5, 6, 9, 10, 41, 69, 88, and 95; (vi) HPV genotypes 1a, 2a, 3, 4, 5, 6, 9, 10, 31, 41, 51, 69, 88, and 95; or (vii) HPV genotypes 1a, 2a, 3, 4, 5, 6, 9, 10, 18, 31, 39, 41, 51, 69, 88, and 95.

As will be understood, the aforesaid peptides may be combined in an essentially arbitrary fashion. Preferably, however, the immunogenic polypeptide comprises said HPV L2 N-terminal peptides in a sequence HPV 1a-2a-3-4-10-41; in a sequence HPV 1a-2a-3-4-10-41-63-88-95; in a sequence HPV 1a-2a-3-4-5-6-41-88; in a sequence HPV 1a-2a-3-4-5-6-9-10-41-88; in a sequence HPV 1a-2a-3-4-5-6-9-10-41-88-69-95; in a sequence HPV 1a-2a-3-4-5-6-9-10-41-88-69-95-31-51; and/or in a sequence HPV 1a-2a-3-4-5-6-9-10-41-88-69-95-31-51-18-39. As used herein, variant L2 N-terminal peptides preferably are numbered according to the N-terminal peptide they have the highest % identity to, i.e., preferably, they are most closely related to. Also preferably, in case the immunogenic polypeptide comprises more than one HPV L2 N-terminal peptide assigned to a particular type (e.g. HPV 1a), these more than one HPV L2 N-terminal peptides are preferably comprised in the immunogenic polypeptide in direct succession, optionally intervened by a linker. It is, however, also envisaged by the present invention that the immunogenic polypeptide comprises the aforesaid sequences in a concatenated form, e.g. HPV 1a-2a-3-4-10-41-1a-2a-3-4-10-41, wherein, preferably, the second sequence 1a-2a-3-4-10-41 may comprise variants of the specific sequences comprising at most two, preferably at most one amino acid substitution(s) per HPV L2 N-terminal peptide. Preferably, the immunogenic polypeptide comprises the amino acid sequence of one of SEQ ID NOs: 35 to 41.

Preferably, the HPV L2 N-terminal peptides are comprised in the immunogenic polypeptide in a directly contiguous sequence, i.e. not comprising intervening amino acids. More preferably, the HPV L2 N-terminal peptides in the immunogenic polypeptide are separated by one or more linker sequences, wherein said linker sequence(s) may be identical or may be different for the respective L2 N-terminal peptides intervened. Preferably, said linker has a length of 1 to 5 amino acids, more preferably, the linker consists of 5, 3, or 2 amino acids consisting of proline (P) and glycine (G) residues. The person skilled in the art knows how to select suitable linker peptides. Preferably, said 1 to 5 amino acids comprised by said linker peptide are selected from the group consisting of Glycine (G), Proline (P) or Serine (S). A particularly preferred linker peptide comprises the amino acid sequence GGP (SEQ ID NO: 57). However, also other linkers can be used such as GPGP (SEQ ID NO:58), GPGPG (SEQ ID NO: 59), or SGSG (SEQ ID NO: 60). Preferably, said linker peptide is positioned at the junction of a scaffold polypeptide, e.g., preferably, a thioredoxin polypeptide as described herein below, and the fragment of the L2 polypeptide and/or at the junction of two L2 fragments (or variants thereof). Thus, said linker peptide can be positioned either N-terminally or C-terminally from the L2 fragment (or variant thereof) or both.

Preferably, the multitude of HPV L2 N-terminal peptides comprises the amino acid sequence, more preferably the multitude of HPV L2 N-terminal peptides consists of the amino acid sequence of one of SEQ ID NOs: 35 to 41, or is a variant of said sequence comprising at most two, preferably at most one amino acid substitution(s) per HPV L2 N-terminal peptide. More preferably, the multitude HPV L2 N-terminal peptides comprises the amino acid sequence, more preferably the multitude HPV L2 N-terminal peptides consists of an amino acid sequence selected from SEQ ID NOs: 35 to 41. Thus, preferably, the immunogenic polypeptide comprises, preferably consists of the cHPVL2.6mer sequence (SEQ ID NO: 35), cHPVL2.9mer sequence (SEQ ID NO: 36), cHPVL2.8mer sequence (SEQ ID NO: 37), cHPVL2.10mer sequence (SEQ ID NO: 38), cHPVL2.12mer sequence (SEQ ID NO: 39), cHPVL2.14mer sequence (SEQ ID NO: 40), cHPVL2.16mer sequence (SEQ ID NO: 41), or is a variant of any of the aforesaid sequences. More preferably, the immunogenic polypeptide comprises, preferably consists of the cHPVL2.6mer sequence (SEQ ID NO: 35), cHPVL2.9mer sequence (SEQ ID NO: 36), cHPVL2.8mer sequence (SEQ ID NO: 37), cHPVL2.10mer sequence (SEQ ID NO: 38), cHPVL2.12mer sequence (SEQ ID NO: 39), cHPVL2.14mer sequence (SEQ ID NO: 40), cHPVL2.16mer sequence (SEQ ID NO: 41).

Preferably, the immunogenic polypeptide further comprises an oligomerization domain. The term "oligomerization domain" is used in its conventional meaning and relates to a polypeptide having the property that polypeptides comprising said domain have a propensity to aggregate. Preferably, the dissociation constant for the oligomerization domain as a separate molecule is at most $10^{-4}$ mol/l, more preferably at most $10^{-5}$ mol/l, most preferably at least $10^{-6}$ mol/l. As will be appreciated, the number of molecules aggregating will in particular depend on the type of oligomerization domain selected. Suitable oligomerization domains are known in the art. Preferably, the immunogenic polypeptide comprises at least one oligomerization domain of (i) an oligomerization domain of a C4-binding protein, preferably of a mammalian C4-binding protein, more preferably of a human or mouse C4-binding protein, most preferably of a mouse C4-binding protein; (ii) an encapsulin polypeptide, preferably an encapsulin polypeptide from a thermophilic archaebacterium, more preferably a *Pyrococcus furiosus* encapsulin polypeptide; (iii) a ferritin polypeptide, preferably a ferritin polypeptide from a thermophilic archaebacterium, more preferably a *Pyrococcus furiosus* ferritin polypeptide; and (iv) a hybrid polypeptide of two different chicken C4-binding proteins, preferably an IMX313 polypeptide or a variant thereof, in particular as described in WO 2007/062819 A2, most preferably an IMX313T polypeptide (SEQ ID NO: 55).

Also preferably, the immunogenic polypeptide further comprises an enhancer of immunogenicity, preferably at the N-terminus and/or at the C-terminus of said immunogenic polypeptide. Peptide sequences functioning as enhancers of immunogenicity are, in principle, known in the art. Preferably, the enhancer of immunogenicity is CD4+T-helper epitope, preferably an epitope comprising at least one of (i) p25 from the carboxyl region of *Plasmodium vivax* circumsporozoite protein; (ii) p2 peptide from tetanus toxin; (iii) p30 peptide from tetanus toxin; and (iv) a Pan HLA-DR reactive epitope (PADRE). More preferably, the enhancer of immunogenicity comprises, preferably consists of, a peptide comprising the amino acid sequence of SEQ ID NO: 56 (PADRE). Also preferably, the enhancer of immunogenicity is a peptide comprising the amino acid sequence RGD, known to be an integrin binding motif.

In a preferred embodiment, the multitude of L2 N-terminal peptides is comprised in a thioredoxin polypeptide. Thioredoxin polypeptides suitable for including L2 N-terminal peptides are known in the art from WO 2010/070052. Preferably, the thioredoxin is a mammalian, more preferably human, a bacterial, or an archaebacterial thioredoxin. More preferably, the thioredoxin is an archaebacterial thioredoxin, preferably from a thermophilic archaebacterium, preferably of *Pyrococcus furiosus* or of *Methanosaeta thermophila*. Thus, the thioredoxin preferably has the amino acid sequence of SEQ ID NO: 49 (*E. coli* thioredoxin), preferably encoded by the nucleic acid sequence of SEQ ID NO: 52, or is a variant thereof. More preferably, the thioredoxin has the amino acid sequence of SEQ ID NO: 51 (*P. furiosus* thioredoxin), preferably encoded by the nucleic acid sequence of SEQ ID NO: 54, or is a variant thereof; or has the amino acid sequence of SEQ ID NO: 50 (*M. thermophila* thioredoxin), preferably encoded by the nucleic acid sequence of SEQ ID NO: 53, or is a variant thereof. As will be understood by the skilled person, the thioredoxins of the present invention have the biological activity of being a scaffold for the L2 N-terminal peptides, whereas the redox-activity is not required. Accordingly, according to the present invention, variant thioredoxins with a sequence identity of at least 50% to one of the aforesaid thioredoxins are suitable for use in the immunogenic polypeptide. Preferably, the multitude of L2 N-terminal peptides is inserted into the display site of the thioredoxin, as described in detail in WO 2010/070052. Thus, preferably, the immunogenic polypeptide comprises, preferably consists of the Trx-cHPVL2.6mer sequence (SEQ ID NO: 42), Trx-cHPVL2.9mer sequence (SEQ ID NO: 43), Trx-cHPVL2.8mer sequence (SEQ ID NO: 44), Trx-cHPVL2.10mer sequence (SEQ ID NO: 45), Trx-cHPVL2.12mer sequence (SEQ ID NO: 46), Trx-cHPVL2.14mer sequence (SEQ ID NO: 47), Trx-cHPVL2.16mer sequence (SEQ ID NO: 48), or is a variant of any of the aforesaid sequences. More preferably, the immunogenic polypeptide comprises, preferably consists of the Trx-cHPVL2.6mer sequence (SEQ ID NO: 42), Trx-cHPVL2.9mer sequence (SEQ ID NO: 43), Trx-cHPVL2.8mer sequence (SEQ ID NO: 44), Trx-cHPVL2.10mer sequence (SEQ ID NO: 45), Trx-cHPVL2.12mer sequence (SEQ ID NO: 46), Trx-cHPVL2.14mer sequence (SEQ ID NO: 47), or Trx-cHPVL2.16mer sequence (SEQ ID NO: 48).

Preferably, the thioredoxin and/or the oligomerization domain and/or the enhancer of immunogenicity have less than 50%, more preferably less than 35%, even more preferably less than 25%, most preferably less than 20% amino acid sequence identity to a human polypeptide, preferably to any human polypeptide identified in assembly GRCh38.p7 of the human genome. More preferably, the thioredoxin and/or the oligomerization domain have less than 50%, more preferably less than 35%, even more preferably less than 25%, most preferably less than 20% amino acid sequence identity to a human polypeptide, preferably to any human polypeptide identified in assembly GRCh38.p7 of the human genome. Also preferably, the thioredoxin and/or the oligomerization domain and/or the enhancer of immunogenicity are polypeptides derived from archaebacterial polypeptides. More preferably, the thioredoxin and/or the oligomerization domain are polypeptides derived from archaebacterial polypeptides.

The term "subject", as used herein, relates to an animal, preferably a vertebrate, more preferably a mammal, in particular to livestock like cattle, horse, pig, sheep, and goat, or to a laboratory animal like a rat, mouse, and guinea pig. Most preferably, the subject is a human. Preferably, the subject is in need for a vaccination against PV, more preferably against cutaneous HPV. Preferably, the subject is at increased risk of developing squamous cell carcinoma and/or actinic keratosis, preferably of developing squamous cell carcinoma. More preferably, the subject is planned to be or is under immune suppression, preferably is planned to be immune suppression; thus, preferably, the subject is a subject under a treatment requiring immune suppression or is suffering from a disease causing immune suppression. Thus, preferably, the subject is a HIV patient. More preferably, the subject is a future organ transplant recipient. Thus, preferably, the subject is suffering or prognosticated to suffer from terminal renal failure, from terminal heart failure, and/or from terminal liver failure.

Advantageously, it was found in the work underlying the present invention that the immunogenic polypeptides of the present invention mediate immunity against cutaneous HPV types. Surprisingly, it was found that at the same time immunity against high-risk mucosal HPV types is mediated as well, e.g. against HPV 16 and 18. Moreover, it was very surprisingly found that cross-subgroup immunization can be achieved, since e.g. by vaccination against genotypes of subgroups mu, alpha, and gamma, cross-immunity against genotypes of the beta-subgroup can be induced.

The definitions made above apply mutatis mutandis to the following. Additional definitions and explanations made further below also apply for all embodiments described in this specification mutatis mutandis.

The present invention further relates to an immunogenic polypeptide according to the present invention for use in medicine, and for use in vaccination of a subject against cutaneous HPV infection and/or mucosal HPV infection.

The term "vaccination against HPV infection" as used herein, preferably, relates to administering the compounds as specified herein to elicit an immune response against various HPV genotypes. Thus, vaccination stimulates the immune system and establishes or improves immunity to infection with various HPV genotypes. Preferably, vaccination according to the present invention allows for establishing or improving immunity to infection with human papillomavirus genotypes. Preferably, the vaccination according to the present invention also allows for establishing or improving immunity to infection with at least the cutaneous human papillomavirus genotypes 3, 5, 10, 63, 76, 92, and 96, more preferably 1a, 2a, 3, 4, 5, 6, 9, 10, 41, 69, 88, or 95 and/or the mucosal human papillomavirus genotypes 16 and/or 18; more preferably HPV 11, 16, 18, 31, 35, 39, 51, 58, and 73. In a preferred embodiment, vaccination according to the present invention allows for establishing or improving immunity to infection with human papillomavirus genotypes 1a, 2a, 3, 4, 5, 6, 9, 10, 41, 69, 88, 95, 11, 16, 18, 31, 35, 39, 51, 58, and 73. It is to be understood that the vaccine according to the present invention may comprise further components, in particular as specified elsewhere herein. The skilled person will understand that vaccination may not elicit a significant immune response in all subjects vaccinated. Also, it is to be understood that vaccination may not be effective to prevent infection in all subjects vaccinated. However, the term requires that a, preferably statistically significant, portion of subjects of a cohort or population are effectively vaccinated, wherein effective vaccination, preferably, is prevention or reduction of the number of HPV-induced lesions, such as warts. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

Preferably, vaccination further comprises administration of an adjuvant, preferably simultaneously to administration of the immunogenic polypeptide. More preferably, the immunogenic polypeptide and the adjuvant are comprised in a common mixture at administration. Thus, preferably, the immunogenic polypeptide and the adjuvant are mixed before administration. Preferably, the adjuvant comprises (i) alum and a toll like receptor 4 (TLR4) antagonist, preferably synthetic monophosphoryl lipid A (MPLA), and/or (ii) a squalene-based oil-in-water nano-emulsion, preferably AddaVax™.

Preferably, vaccination against HPV infection of the present invention induces a humoral immune response in a subject, i.e., preferably induces the production of antibodies recognizing, preferably specifically recognizing, an HPV L2 polypeptide. The term "specifically recognizing" is understood by the skilled person as the property of a binding agent, e.g. an antibody, to specifically bind to a particular species of molecule, while other molecules from the same chemical class of molecules, e.g. proteins, are not recognized or are recognized to a much lesser extent. Preferably, the binding constant of an antibody specifically recognizing a HPV L2 polypeptide for a HPV L2 polypeptide is at least a factor 100, more preferably at least a factor of at least 1000, most preferably a factor of at least 10000 lower than for any non-HPV L2 polypeptide. Preferably, the antibodies specifically recognizing an HPV L2 polypeptide are antibodies specifically recognizing an HPV capsid. Preferably, the antibodies specifically recognizing an HPV L2 polypeptide are antibodies neutralizing an HPV capsid. Preferably, vaccination against HPV infection induces a humoral and a cellular immune response in a subject.

The present invention also relates to a polynucleotide encoding the immunogenic polypeptide according to the present invention.

As used herein, the term polynucleotide, preferably, includes variants of the specifically indicated polynucleotides. More preferably, the term polynucleotide relates to the specific polynucleotides indicated. It is to be understood, however, that a polypeptide having a specific amino acid sequence may be also encoded by a variety of polynucleotides, due to the degeneration of the genetic code. The skilled person knows how to select a polynucleotide encoding a polypeptide having a specific amino acid sequence and also knows how to optimize the codons used in the polynucleotide according to the codon usage of the organism used for expressing said polynucleotide; e.g. preferably, the sequences of SEQ ID NOs: 61 to 67 are sequences encoding multitudes of HPV L2 N-terminal peptides and are codon optimized for expression in $E.\ coli$. Thus, the term "polynucleotide variant", as used herein, relates to a variant of a polynucleotide related to herein comprising a nucleic acid sequence characterized in that the sequence can be derived from the aforementioned specific nucleic acid sequence by at least one nucleotide substitution, addition and/or deletion, wherein the polynucleotide variant shall have the activity as specified for the specific polynucleotide, i.e. shall encode an immunogenic polypeptide according to the present invention. Moreover, it is to be understood that a polynucleotide variant as referred to in accordance with the present invention shall have a nucleic acid sequence which differs due to at least one nucleotide substitution, deletion and/or addition. Preferably, said polynucleotide variant is an ortholog, a paralog or another homolog of the specific polynucleotide. Also preferably, said polynucleotide variant is a naturally occurring allele of the specific polynucleotide. Polynucleotide variants also encompass polynucleotides comprising a nucleic acid sequence which is capable of hybridizing to the aforementioned specific polynucleotides, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1× to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of a polypeptide of the present invention. Conserved domains of a polypeptide may be identified by a sequence comparison of the nucleic acid sequence of the polynucleotide or the amino acid sequence of the polypeptide of the present invention with sequences of other organisms. As a template, DNA or cDNA from bacteria, fungi, plants or, preferably, from animals may be used. Further, variants include polynucleotides comprising nucleic acid sequences which are at least 70%, at least 75%, at least 80%, at least 85%, at least 90%, at least 95%, at least 98% or at least 99% identical to the specifically indicated nucleic acid sequences. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences specifically indicated. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit [Needleman and Wunsch (J. Mol. Biol. 48; 443-453 (1970)) and Smith and Waterman (Adv. Appl. Math. 2; 482-489 (1981))], which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the specifically indicated nucleic acid sequences is also encompassed as a variant polynucleotide of the present invention. The fragment shall still encode an immunogenic polypeptide which still has the activity as specified. Accordingly, the immunogenic polypeptide encoded may comprise or consist of the domains of the immunogenic polypeptide of the present invention conferring the said biological activity. A fragment as meant herein, preferably, comprises at least 50, at least 100, at least 250 or at least 500 consecutive nucleotides of any one of the specific nucleic acid sequences or encodes an amino acid sequence comprising at least 20, at least 30, at least 50, at least 80, at least 100 or at least 150 consecutive amino acids of any one of the specific amino acid sequences.

The polynucleotides of the present invention either consist, essentially consist of, or comprise the aforementioned nucleic acid sequences. Thus, they may contain further nucleic acid sequences as well. Specifically, the polynucleotides of the present invention may encode fusion proteins wherein one partner of the fusion protein is an immunogenic polypeptide being encoded by a nucleic acid sequence recited above. Such fusion proteins may comprise as additional part polypeptides for monitoring expression (e.g., green, yellow, blue or red fluorescent proteins, alkaline phosphatase and the like), so called "tags" which may serve as a detectable marker or as an auxiliary measure for purification purposes, and/or scaffold polypeptides such as thioredoxin, as described herein above. Tags for the different purposes are well known in the art and are described elsewhere herein.

The polynucleotide of the present invention shall be provided, preferably, either as an isolated polynucleotide (i.e. isolated from its natural context) or in genetically modified form. The polynucleotide, preferably, is DNA, including cDNA, or is RNA. The term encompasses single as well as double stranded polynucleotides. Moreover, preferably, comprised are also chemically modified polynucleotides including naturally occurring modified polynucleotides such as glycosylated or methylated polynucleotides or artificial modified one such as biotinylated polynucleotides.

Furthermore, the present invention relates to a vector comprising the polynucleotide according to the present invention.

The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerenes. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. In a preferred embodiment, the vector is a bacterial vector, preferably having a p15A origin of replication and/or carrying a kanamycin resistance gene.

More preferably, in the vector of the invention the polynucleotide is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). In a preferred embodiment, the vector is a bacterial expression vector carrying the nucleic acid sequence encoding the immunogenic polypeptide under the control of an inducible promoter, preferably the tac promoter; also preferably, said the vector additionally carries a gene encoding an expressible gene encoding a functional lac inhibitor. Thus, in a preferred embodiment, the vector is a bacterial expression vector, preferably having a p15A origin of replication, carrying a kanamycin resistance gene, a gene encoding an expressible gene encoding a functional lac inhibitor, and encoding the immunogenic polypeptide under the control of the tac promoter.

The present invention also relates to a host cell comprising the polynucleotide according to the present invention and/or the vector according to the present invention.

As used herein, the term "host cell" relates to any cell capable of receiving and, preferably maintaining, the polynucleotide and/or the vector of the present invention. More preferably, the host cell is capable of expressing an immunogenic polypeptide of the present invention encoded on said polynucleotide and/or vector. Preferably, the cell is a bacterial cell, more preferably a cell of a common laboratory bacterial strain known in the art, most preferably an *Escherichia* strain, in particular an *E. coli* strain. Also preferably, the host cell is an eukaryotic cell, preferably a yeast cell, e.g. a cell of a strain of baker's yeast, or is an animal cell. More preferably, the host cell is an insect cell or a mammalian cell, in particular a mouse or rat cell. Most preferably, the host cell is a mammalian cell.

The present invention further relates to a pharmaceutical composition comprising the immunogenic polypeptide according to the present invention, the polynucleotide according the present invention, the vector according the present invention, and/or the host cell according to the present invention; and a pharmaceutically acceptable carrier.

The term "pharmaceutical composition", as used herein, relates to a composition comprising the compound or compounds of the present invention in a pharmaceutically acceptable form and a pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. Preferably, the pharmaceutical composition of the present invention is administered via a parenteral route, preferably subcutaneously, intramuscularly, or intraperitoneally. In case the subject is a human, administration preferably is intramuscularly. However, polynucleotide compounds may also be administered in a gene therapy approach by using viral vectors, viruses or liposomes, and may also be administered topically, e.g. as an ointment. Moreover, the compounds can be administered in combination with other drugs either in a common pharmaceutical composition or as separated pharmaceutical compositions wherein said separated pharmaceutical compositions may be provided in form of a kit of parts. In particular, co-administration of adjuvants is envisaged, as specified elsewhere herein. Preferably, the immunogenic polypeptide, the polynucleotide and the pharmaceutical composition are provided in lyophilized form.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like.

Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are preferably selected so as not to affect the biological activity of the immunogenic polypeptide, polynucleotide, vector, or host cell and potential further pharmaceutically active ingredients. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats a condition referred to herein. Therapeutic efficacy and toxicity of compounds can be determined by standard pharmaceutical procedures in cell culture or in experimental animals, e.g., by determining the ED50 (the dose therapeutically effective in 50% of the population) and/or the LD50 (the dose lethal to 50% of the population). The dose ratio between therapeutic and toxic effects is the therapeutic index, and it can be expressed as the ratio, LD50/ED50.

The dosage regimen will be determined by the attending physician, preferably taking into account relevant clinical factors and, preferably, in accordance with any one of the methods described elsewhere herein. As is well known in the medical arts, a dosage for any one patient may depend upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 µg to 10000 µg; however, doses below or above this exemplary range are envisioned, especially considering the aforementioned factors. Generally, the regimen comprises administration of 1 µg to 10 mg of an antigen as a primary immunization, followed by one or more than one boost administration of the same antigen, preferably in the same dosage. However, depending on the subject and the mode of administration, the quantity of substance administration may vary over a wide range to provide from about 0.01 mg per kg body mass to about 1 mg per kg body mass, preferably. The pharmaceutical compositions and formulations referred to herein are administered at least once in order to treat or prevent a disease or condition recited in this specification. However, the said pharmaceutical compositions may be administered more than one time, for example, preferably from one to four times, more preferably two or three times.

Specific pharmaceutical compositions are prepared in a manner well known in the pharmaceutical art and comprise at least an immunogenic polypeptide, polynucleotide, vector, or host cell as an active compound in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescriber or user instructions in order to anticipate dose adjustments depending on the considered recipient.

The present invention further relates to a kit comprising an immunogenic polypeptide according to the present invention, a polynucleotide according to the present invention, a vector according to the present invention, and/or a host cell according to the present invention comprised in a housing.

The term "kit", as used herein, refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention, preferably, is to be used for practicing the methods referred to herein above. It is, preferably, envisaged that all components are provided in a ready-to-use manner for practicing the methods referred to above. Further, the kit, preferably, contains instructions for carrying out said methods. The instructions can be provided by a user's manual in paper or electronic form. In addition, the manual may comprise instructions for administration and/or dosage instructions for carrying out the aforementioned methods using the kit of the present invention. As will be understood from the above, the description of the kit comprising polynucleotides, preferably, relates to a kit comprising corresponding vectors mutatis mutandis.

Preferably, the kit comprises the immunogenic polypeptide according to the present invention and an adjuvant. The term "adjuvant" is used herein in its usual meaning in the art. Preferably, the adjuvant comprises (i) alum and a toll like receptor 4 (TLR4) antagonist, preferably synthetic monophosphoryl lipid A (MPLA), and/or (ii) a squalene-based oil-in-water nano-emulsion, preferably AddaVax™. Also preferably, the kit comprises a diluent and/or a means of administration. Appropriate diluents are described herein above; Means of administration are all means suitable for administering the immunogenic polypeptide, the polynucleotide, the vector, and/or the host cell to a subject. The means of administration may include a delivery unit for the administration of the compound or composition and a storage unit for storing said compound or composition until administration. However, it is also contemplated that the means of the current invention may appear as separate devices in such an embodiment and are, preferably, packaged together in said kit. Preferred means for administration are those which can be applied without the particular knowledge of a specialized technician. In a preferred embodiment, the means for administration is a syringe, more preferably with a needle, comprising the compound or composition of the invention. In another preferred embodiment, the means for administration is an intravenous infusion (IV) equipment comprising the compound or composition. In still another preferred embodiment the means for administration is an inhaler comprising the compound of the present invention, wherein, more preferably, said compound is formulated for administration as an aerosol.

The present invention further relates to a method of vaccinating a subject against HPV infection comprising (a) contacting said subject with an immunogenic polypeptide according to the present invention, a polynucleotide according to the present invention, a vector according to the present invention, and/or a host cell according to the present invention, and (b) thereby, vaccinating said subject against HPV infection.

The method of vaccinating of the present invention, preferably, is an in vivo method. Moreover, it may comprise steps in addition to those explicitly mentioned above. For example, further steps may relate, e.g., to contacting said subject with an adjuvant as specified elsewhere herein, and/or repeating said contacting with a compound of the present invention to enhance immune response. In the method of vaccinating, the subject, preferably, is a mammal, more preferably is a human.

Moreover, the present invention relates to a method for producing antibodies against an HPV L2 polypeptide, comprising
(a) contacting a subject with an immunogenic polypeptide according to the present invention, a polynucleotide according to the present invention, a vector according to the present invention, and/or a host cell according to the present invention, and
(b) harvesting antibodies generated by said subject from a bodily fluid of said subject and/or harvesting cells producing said antibodies from said subject.

The method for producing antibodies of the present invention, preferably, is an in vivo method performed at least in part on a, preferably non-human, subject. Preferably, the non-human subject is sacrificed after the method is performed, preferably after the bodily fluid of step b) has been obtained. Moreover, the method may comprise steps in addition to those explicitly mentioned above. For example, further steps may relate, e.g., to purifying the antibodies harvested, or fusing the cells harvested to generate cell lines producing monoclonal antibodies according to well known methods. Also, one or more of the method steps may be performed by automated equipment.

Further, the present invention relates to an antibody produced or producible by the method according to the present invention for use in medicine, preferably for use in passive immunization of a subject against cutaneous HPV infection and/or mucosal HPV infection.

The present invention also relates to a method of passive immunization of a subject against HPV infection comprising
(a) contacting said subject with an antibody produced according to the method for producing antibodies of the present invention, and
(b) thereby, passively vaccinating said subject against HPV infection.

The term "passive immunization" is understood by the skilled person and relates to a method of preventing or treating disease by transferring compounds immune-active against an antigen, e.g. T-cells, B-cells, or antibodies, more preferably antibodies, into a subject lacking a sufficient immune response against said antigen. Thus, preferably, passive immunization is administering to a subject in need of immune enhancement against an antigen antibodies specifically recognizing said antigen. Methods for administering immune-active compounds to a subject are known in the art and include in particular administering an antiserum or partially or completely purified antibodies, preferably monoclonal antibodies, to said subject.

In view of the above, the following embodiments are particularly envisaged:
1. An immunogenic polypeptide comprising a multitude of papillomavirus (PV) L2 N-terminal peptides corresponding to amino acids 20 to 50 of the L2 polypeptide of HPV16, wherein said HPV L2 N-terminal peptides are L2 N-terminal peptides from at least four, preferably at least five, more preferably at least six, different cutaneous HPV genotypes.
2. The immunogenic polypeptide of embodiment 1, wherein said multitude is a number of from 5 to 20, preferably of from 6 to 19, most preferably of from 6 to 16 PV L2 N-terminal peptides.
3. The immunogenic polypeptide of embodiment 1 or 2, wherein said PV L2 N-terminal peptides are peptides corresponding to amino acids 20 to 38 of the L2 polypeptide of HPV16.
4. The immunogenic polypeptide of any one of embodiments 1 to 3, wherein said immunogenic polypeptide comprises three copies, more preferably two copies, most preferably one copy of each of said PV L2 N-terminal peptides.
5. The immunogenic polypeptide of any one of embodiments 1 to 4, wherein said PV L2 N-terminal peptides are from human papillomaviruses (HPVs).
6. The immunogenic polypeptide of any one of embodiments 1 to 5, wherein said PV L2 N-terminal peptides comprise L2 N-terminal peptides of cutaneous HPV genotypes 1a, 2a, 3, and/or 4 or variants thereof comprising at most two, preferably at most one amino acid substitution(s) per HPV L2 N-terminal peptide.
7. The immunogenic polypeptide of any one of embodiments 1 to 6, wherein said HPV L2 N-terminal peptides comprise L2 N-terminal peptides of cutaneous HPV genotypes 1a, 2a, 3, and 4, preferably having the amino acid sequences of SEQ ID NO: 18 (HPV1a), SEQ ID NO: 19 (HPV2a), SEQ ID NO: 20 (HPV3), and SEQ ID NO: 21 (HPV4).
8. The immunogenic polypeptide of any one of embodiments 1 to 7, wherein said HPV L2 N-terminal peptides further comprise L2 N-terminal peptides of cutaneous HPV genotypes of at least one of HPV 5, 6, 9, 10, 39, 41, 63, 69, 88, and 95 or variants thereof comprising at most two, preferably at most one amino acid substitution(s) per HPV L2 N-terminal peptide.
9. The immunogenic polypeptide of any one of embodiments 1 to 8, wherein said HPV L2 N-terminal peptides further comprise L2 N-terminal peptides of cutaneous HPV genotypes of at least one of HPV 5, 6, 9, 10, 39, 41, 63, 69, 88, and 95, preferably having the amino acid sequences of SEQ ID NO: 22 (HPV5), SEQ ID NO: 23 (HPV6),SEQ ID NO: 24 (HPV9), SEQ ID NO: 25 (HPV10),SEQ ID NO: 28 (HPV39), SEQ ID NO: 29 (HPV41), SEQ ID NO: 31 (HPV63), SEQ ID NO: 32 (HPV69), SEQ ID NO: 33 (HPV88), and SEQ ID NO: 34 (HPV95).
10. The immunogenic polypeptide of any one of embodiments 1 to 9, wherein said immunogenic polypeptide further comprises HPV L2 N-terminal peptides from at least one, preferably at least two, even more preferably at least three, most preferably at least four mucosal HPV genotypes.
11. The immunogenic polypeptide of embodiment 10, wherein said mucosal HPV genotypes are selected from HPV 18, 31, 39, and 51.
12. The immunogenic polypeptide of any one of embodiments 1 to 11, wherein said HPV L2 N-terminal peptides comprise L2 N-terminal peptides of
(i) cutaneous HPV genotypes 1a, 2a, 3, 4, 10, and 63 or variants thereof comprising at most two, preferably at most one amino acid substitution(s) per HPV L2 N-terminal peptide;
(ii) cutaneous HPV genotypes 1a, 2a, 3, 4, 10, 41, 63, 88, and 95 or variants thereof comprising at most two, preferably at most one amino acid substitution(s) per HPV L2 N-terminal peptide;
(iii) cutaneous HPV genotypes 1a, 2a, 3, 4, 5, 6, 41, 88 or variants thereof comprising at most two, preferably at most one amino acid substitution(s) per HPV L2 N-terminal peptide;

(iv) cutaneous HPV genotypes 1a, 2a, 3, 4, 5, 6, 9, 10, 41, 88 or variants thereof comprising at most two, preferably at most one amino acid substitution(s) per HPV L2 N-terminal peptide;
(v) cutaneous HPV genotypes 1a, 2a, 3, 4, 5, 6, 9, 10, 41, 69, 88, and 95 or variants thereof comprising at most two, preferably at most one amino acid substitution(s) per HPV L2 N-terminal peptide;
(vi) HPV genotypes 1a, 2a, 3, 4, 5, 6, 9, 10, 31, 41, 51, 69, 88, and 95 or variants thereof comprising at most two, preferably at most one amino acid substitution(s) per HPV L2 N-terminal peptide; or
(vii) HPV genotypes 1a, 2a, 3, 4, 5, 6, 9, 10, 18, 31, 39, 41, 51, 69, 88, and 95 or variants thereof comprising at most two, preferably at most one amino acid substitution(s) per HPV L2 N-terminal peptide.

13. The immunogenic polypeptide of any one of embodiments 1 to 12, wherein said HPV L2 N-terminal peptides comprise L2 N-terminal peptides of
(i) cutaneous HPV genotypes 1a, 2a, 3, 4, 10, and 63;
(ii) cutaneous HPV genotypes 1a, 2a, 3, 4, 10, 41, 63, 88, and 95;
(iii) cutaneous HPV genotypes 1a, 2a, 3, 4, 5, 6, 41, 88;
(iv) cutaneous HPV genotypes 1a, 2a, 3, 4, 5, 6, 9, 10, 41, 88;
(v) cutaneous HPV genotypes 1a, 2a, 3, 4, 5, 6, 9, 10, 41, 69, 88, and 95;
(vi) HPV genotypes 1a, 2a, 3, 4, 5, 6, 9, 10, 31, 41, 51, 69, 88, and 95; or
(vii) HPV genotypes 1a, 2a, 3, 4, 5, 6, 9, 10, 18, 31, 39, 41, 51, 69, 88, and 95.

14. The immunogenic polypeptide of any one of embodiments 1 to 13, wherein said immunogenic polypeptide comprises said HPV L2 N-terminal peptides in a sequence HPV 1a-2a-3-4-10-41.

15. The immunogenic polypeptide of any one of embodiments 1 to 13, wherein said immunogenic polypeptide comprises said HPV L2 N-terminal peptides in a sequence HPV 1a-2a-3-4-10-41-63-88-95.

16. The immunogenic polypeptide of any one of embodiments 1 to 13, wherein said immunogenic polypeptide comprises said HPV L2 N-terminal peptides in a sequence HPV 1a-2a-3-4-5-6-41-88.

17. The immunogenic polypeptide of any one of embodiments 1 to 13, wherein said immunogenic polypeptide comprises said HPV L2 N-terminal peptides in a sequence HPV 1a-2a-3-4-5-6-9-10-41-88.

18. The immunogenic polypeptide of any one of embodiments 1 to 13, wherein said immunogenic polypeptide comprises said HPV L2 N-terminal peptides in a sequence HPV 1a-2a-3-4-5-6-9-10-41-88-69-95

19. The immunogenic polypeptide of any one of embodiments 1 to 13, wherein said immunogenic polypeptide comprises said HPV L2 N-terminal peptides in a sequence HPV 1a-2a-3-4-5-6-9-10-41-88-69-95-31-51.

20. The immunogenic polypeptide of any one of embodiments 1 to 13, wherein said immunogenic polypeptide comprises said HPV L2 N-terminal peptides in a sequence HPV 1a-2a-3-4-5-6-9-10-41-88-69-95-31-51-18-39.

21. The immunogenic polypeptide of any one of embodiments 1 to 20, wherein said multitude HPV L2 N-terminal peptides comprises, preferably consists of SEQ ID NOs: 35 to 41 or is a variant of said immunogenic polypeptide comprising at most two, preferably at most one amino acid substitution(s) per HPV L2 N-terminal peptide.

22. The immunogenic polypeptide of any one of embodiments 1 to 21, wherein said multitude HPV L2 N-terminal peptides comprises, preferably consists of SEQ ID NOs: 35 to 41.

23. The immunogenic polypeptide of any one of embodiments 1 to 22 further comprising an oligomerization domain, preferably wherein said oligomerization domain is at least one of
(i) an oligomerization domain of a C4-binding protein, preferably of a mammalian C4-binding protein, more preferably of a human or mouse C4-binding protein, most preferably of a mouse C4-binding protein;
(ii) an encapsulin polypeptide, preferably an encapsulin polypeptide from a thermophilic archaebacterium, more preferably a *Pyrococcus furiosus* encapsulin polypeptide;
(iii) a ferritin polypeptide, preferably a ferritin polypeptide from a thermophilic archaebacterium, more preferably a *Pyrococcus furiosus* ferritin polypeptide; and
(iv) a hybrid polypeptide of two different chicken C4-binding proteins, preferably an IMX313T polypeptide.

24. The immunogenic polypeptide of any one of embodiments 1 to 23, wherein said oligomerization domain comprises, preferably consists of, SEQ ID NO: 55.

25. The immunogenic polypeptide of any one of embodiments 1 to 24, wherein said immunogenic polypeptide further comprises an enhancer of immunogenicity, preferably at the N-terminus and/or at the C-terminus of said immunogenic polypeptide.

26. The immunogenic polypeptide of embodiment 25, wherein said enhancer of immunogenicity is a CD4+T-helper epitope or is a peptide comprising the amino acid sequence RGD.

27. The immunogenic polypeptide of embodiment 26, wherein said CD4+T-helper epitope comprises at least one of
(i) p25 from the carboxyl region of *Plasmodium vivax* circumsporozoite protein;
(ii) p2 peptide from tetanus toxin;
(iii) p30 peptide from tetanus toxin; and
(iv) a Pan HLA-DR reactive epitope (PADRE).

28. The immunogenic polypeptide of any one of embodiments 26 or 27, wherein said CD4+T-helper epitope comprises, preferably consists of, SEQ ID NO: 56.

29. The immunogenic polypeptide of any one of embodiments 1 to 28, wherein said multitude of HPV L2 N-terminal peptides is comprised in a thioredoxin polypeptide.

30. The immunogenic polypeptide of embodiment 29, wherein said thioredoxin is a human, bacterial, or an archaebacterial thioredoxin.

31. The immunogenic polypeptide of embodiment 29 or 30, wherein said thioredoxin is a thioredoxin of a thermophilic archaebacterium, preferably of *Pyrococcus furiosus*, preferably having the sequence of SEQ ID NO: 51.

32. The immunogenic polypeptide of any one of embodiments 29 to 31, wherein said multitude of HPV L2 N-terminal peptides is comprised in the display site of said thioredoxin.

33. The immunogenic polypeptide of any one of embodiments 1 to 32, wherein said immunogenic polypeptide comprises
(i) the amino acid of one of SEQ ID NOs: 42 to 48;
(ii) an amino acid sequence at least 70% identical to an amino acid sequence of one of SEQ ID NOs: 42 to 48;
(iii) a polypeptide sequence encoded by one of SEQ ID NOs: 61 to 67; and/or
(iv) a polypeptide encoded by a polynucleotide sequence at least 70% identical to a sequence of SEQ ID NOs: 61 to 67.

34. An immunogenic polypeptide according to any one of embodiments 1 to 33 for use in medicine.

35. An immunogenic polypeptide according to any one of embodiments 1 to 33 for use in vaccination of a subject against cutaneous HPV infection and/or mucosal HPV infection.

36. The immunogenic polypeptide for use of embodiment 35, wherein said subject is planned to be or is under immune suppression, preferably is planned to be immune suppression.

37. The immunogenic polypeptide for use of embodiment 35 or 36, wherein said subject is a future organ transplant recipient.

38. The immunogenic polypeptide for use of any one of embodiments 35 to 37, wherein said subject is at increased risk of developing squamous cell carcinoma and/or actinic keratosis, preferably of developing squamous cell carcinoma.

39. The immunogenic polypeptide for use of any one of embodiments 35 to 38, wherein said vaccination is vaccination against at least HPV 3, 5, 10, 63, 76, 92, and 96.

40. The immunogenic polypeptide for use of any one of embodiments 35 to 39, wherein said vaccination is vaccination against at least HPV 3, 4, 5, 10, 63, 76, 92, 95, and 96.

41. The immunogenic polypeptide for use of any one of embodiments 35 to 40, wherein said vaccination comprises vaccination against at least HPV 16 and/or 18.

42. The immunogenic polypeptide for use of any one of embodiments 35 to 41, wherein said vaccination comprises vaccination against at least HPV 11, 16, 18, 35, 51, 58, and/or 73.

43. A polynucleotide encoding the immunogenic polypeptide according to any one of embodiments 1 to 33.

44. A vector comprising the polynucleotide according to embodiment 43.

45. A host cell comprising the polynucleotide according to embodiment 43 and/or the vector according to embodiment 44.

46. A pharmaceutical composition comprising the immunogenic polypeptide according to any one of embodiments 1 to 33, the polynucleotide according to embodiment 43, the vector according to embodiment 44, and/or the host cell according to embodiment 45; and a pharmaceutically acceptable carrier.

47. A kit comprising the immunogenic polypeptide according to any one of embodiments 1 to 33, the polynucleotide according to embodiment 43, the vector according to embodiment 44, and/or the host cell according to embodiment 45 comprised in a housing.

48. The kit of embodiment 47, wherein said kit comprises the immunogenic polypeptide according to any one of embodiments 1 to 33, and an adjuvant.

49. The kit of embodiment 48, wherein said adjuvant preferably comprises (i) alum and a toll like receptor 4 (TLR4) antagonist, preferably synthetic monophosphoryl lipid A (MPLA), and/or (ii) a squalene-based oil-in-water nanoemulsion, preferably AddaVax™ 50. The kit of any one of embodiments 47 to 49, wherein said kit further comprises a diluent and/or a means of administration.

51. A method of vaccinating a subject against HPV infection comprising
(a) contacting said subject with an immunogenic polypeptide according to any one of embodiments 1 to 33, the polynucleotide according to embodiment 43, the vector according to embodiment 44, and/or the host cell according to embodiment 45, and
(b) thereby, actively vaccinating said subject against HPV infection.

52. A method for producing antibodies against an HPV L2 polypeptide, comprising
(a) contacting a subject with an immunogenic polypeptide according to any one of embodiments 1 to 33, the polynucleotide according to embodiment 43, the vector according to embodiment 44, and/or the host cell according to embodiment 45, and
(b) harvesting antibodies generated by said subject from a bodily fluid of said subject and/or harvesting cells producing said antibodies from said subject.

53. An antibody produced or producible by the method according to embodiment 52 for use in medicine, preferably for use in passive immunization of a subject against cutaneous HPV infection and/or mucosal HPV infection.

54. A method of passive immunization of a subject against HPV infection comprising
(a) contacting said subject with an antibody produced according to the method according to embodiment 52, and
(b) thereby, passively vaccinating said subject against HPV infection.

All references cited in this specification are herewith incorporated by reference with respect to their entire disclosure content and the disclosure content specifically mentioned in this specification.

FIGURE LEGENDS

FIG. 1: Schematic representation of the constructs used in the examples; Trx: *Pyrococcus furiosus* Thioredoxin, Trx-N: N-terminal part of Thioredoxin, Trx-C: C-terminal part of Thioredoxin; numbers refer to HPV genotypes.

Figure 2:
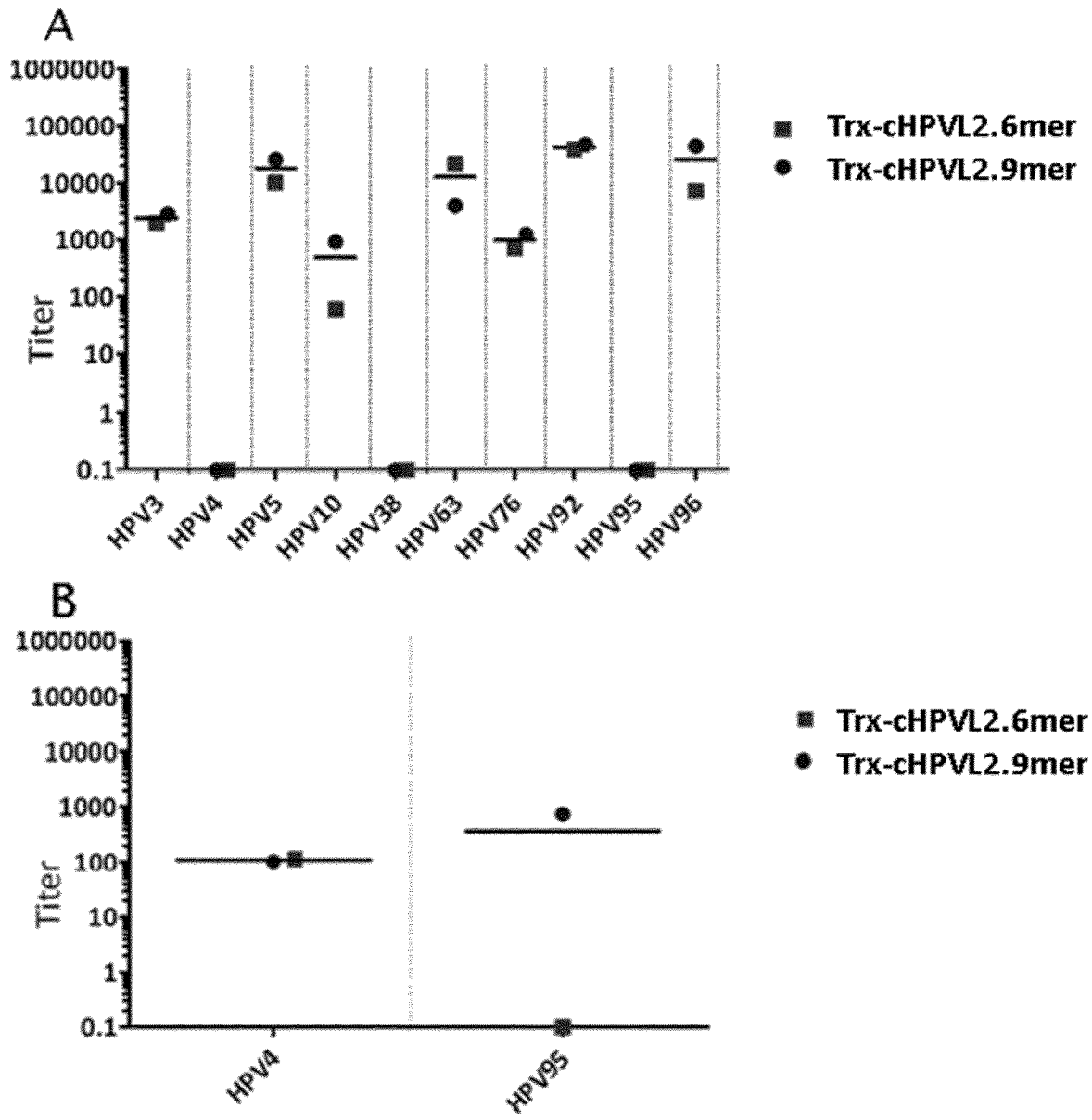
Figure 2:
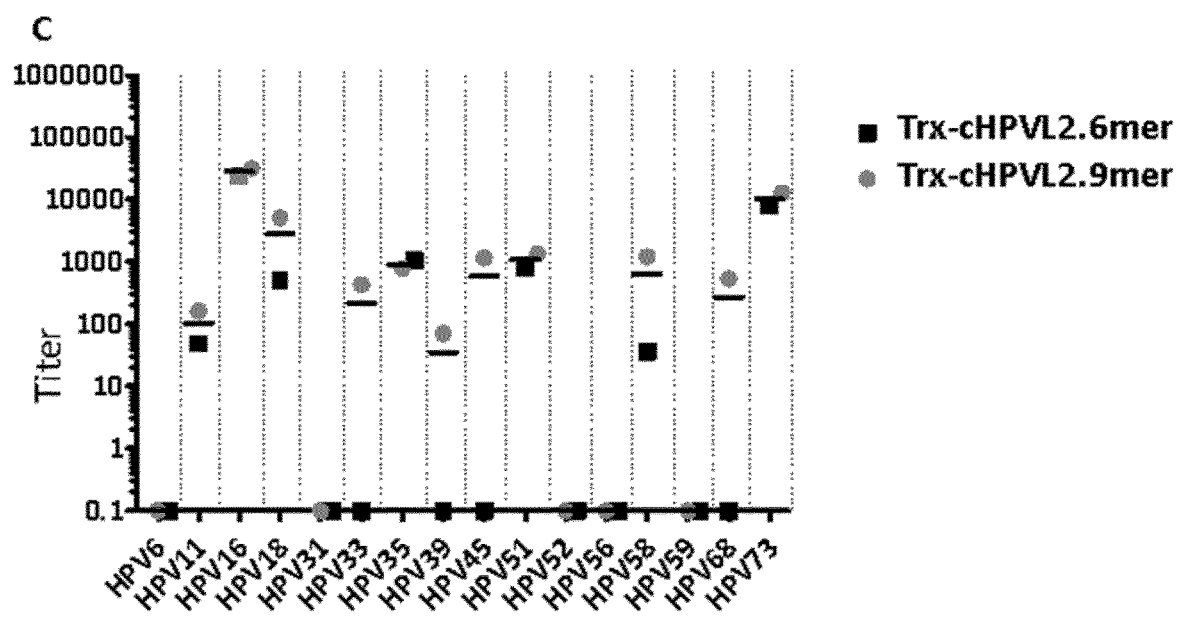

FIG. 2: PBNA assays with sera from guinea pigs immunized with immunogenic polypeptides as indicated. (A) L1-PBNA using cutaneous HPV genotypes as targets; (B) L2-PBNA using cutaneous HPV genotypes 4 and 95 as targets; (C) L1-PBNA using mucosal HPV genotypes as targets.

Figure 3:
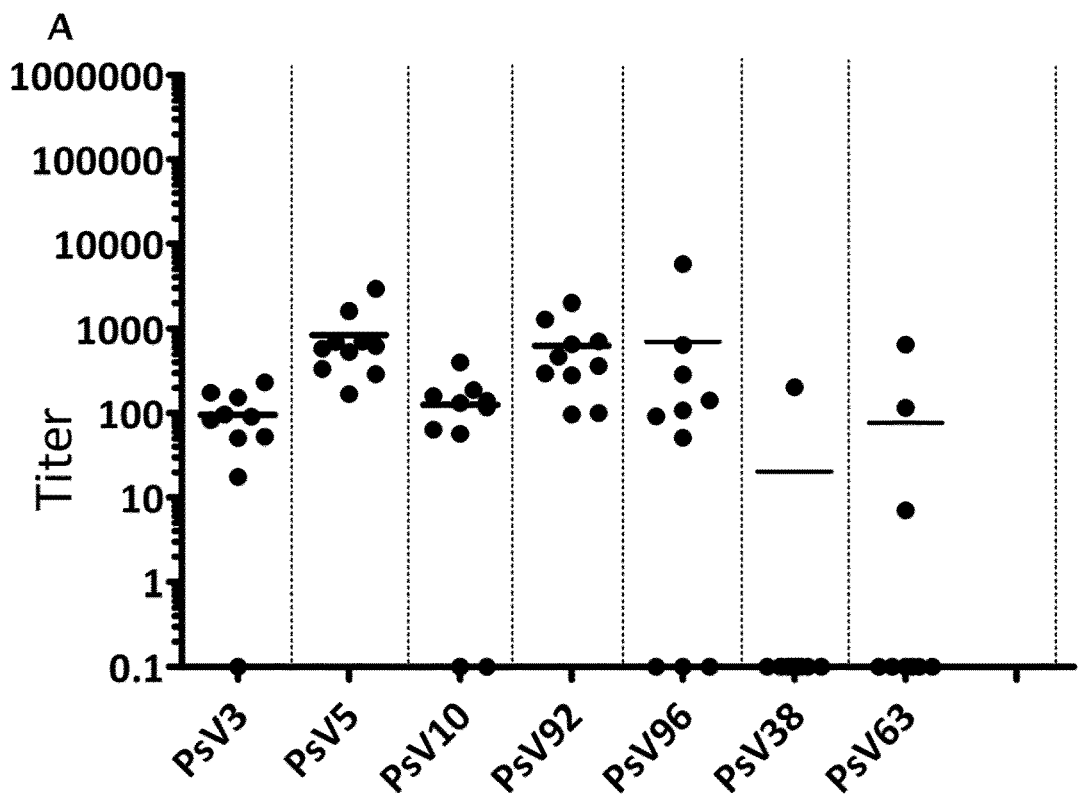
Figure 3:
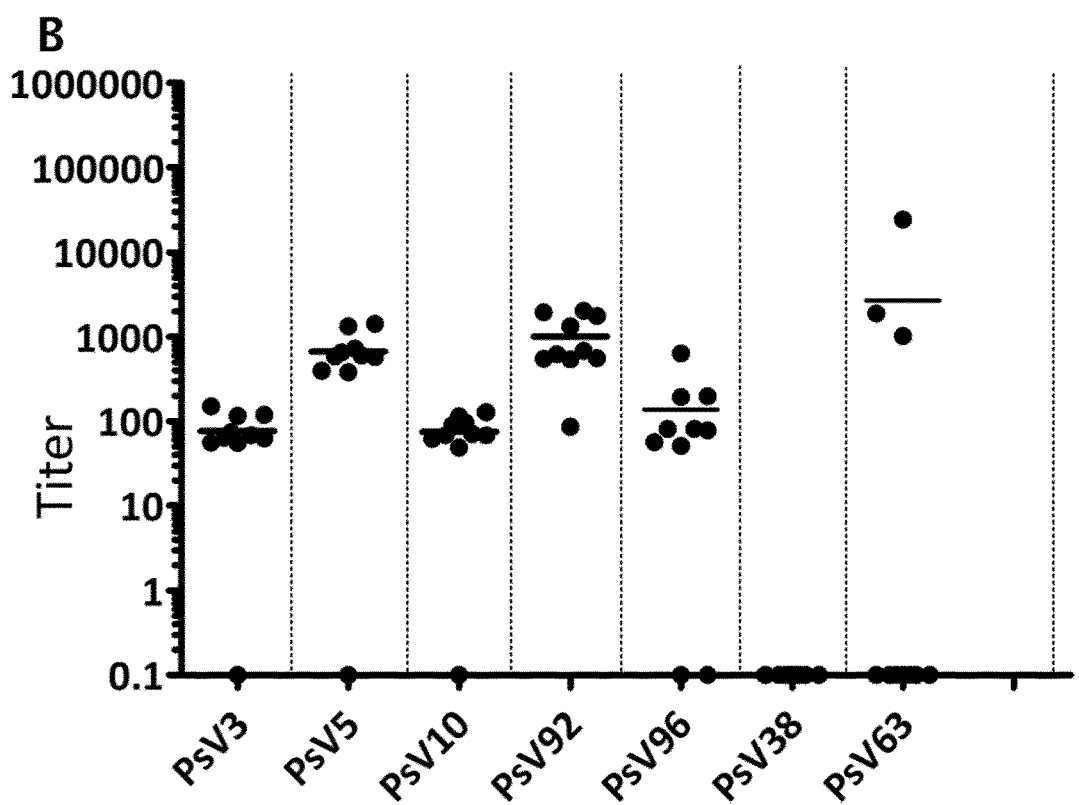

FIG. 3: L1-PBNA assays with sera from mice immunized with immunogenic polypeptides as indicated using cutaneous HPV genotypes as targets; for mouse immunization, constructs additionally comprising an IMX313T domain were used. (A) Sera after immunization with the timer construct; (B) Sera after immunization with the 9mer construct.

Figure 4:
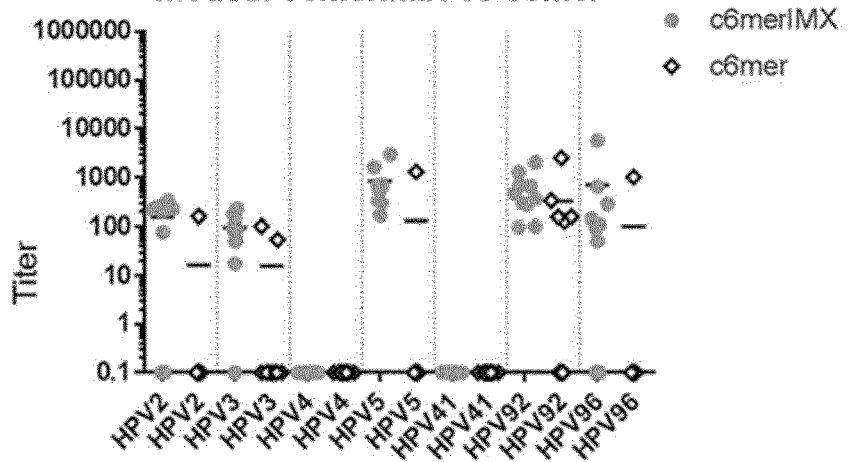
Figure 4:
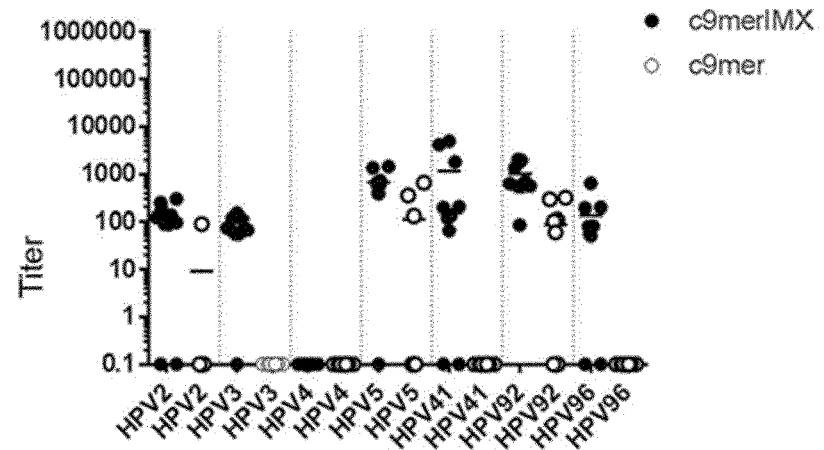
Figure 4:
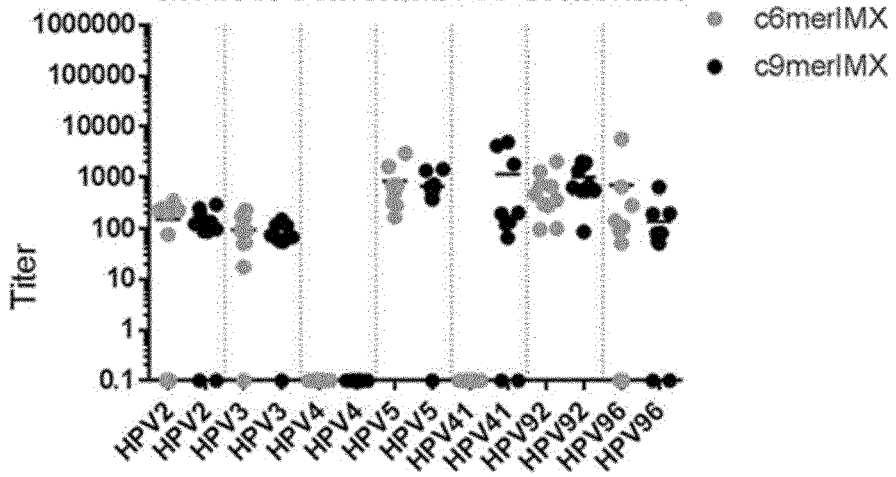

FIG. 4: Effect of the IMX domain in the immunogenicity of the cutaneous candidate vaccines. Neutralizing antibody titers were assessed from mice sera following immunization with c6mer, 9cmer, c6mer.IMX and c9mer.IMX. Each dot or rhombus represents a single mouse; geometric 520 means of the titers for each group (10 animals) are indicated by horizontal lines. The y-axis displays EC50 titers. Results are shown for absence or presence of an IMX heptamerization domain for the c6mer (A) and c9mer (B) polytopes, a comparison of c6mer.IMX and c9mer.IMX is provided in (C).

Figure 5:
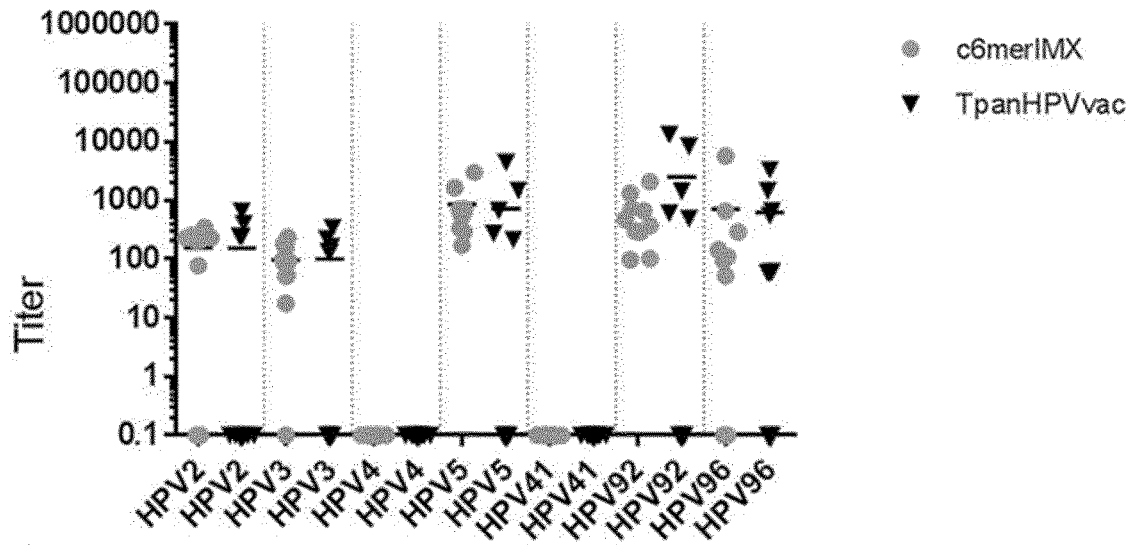
Figure 5:
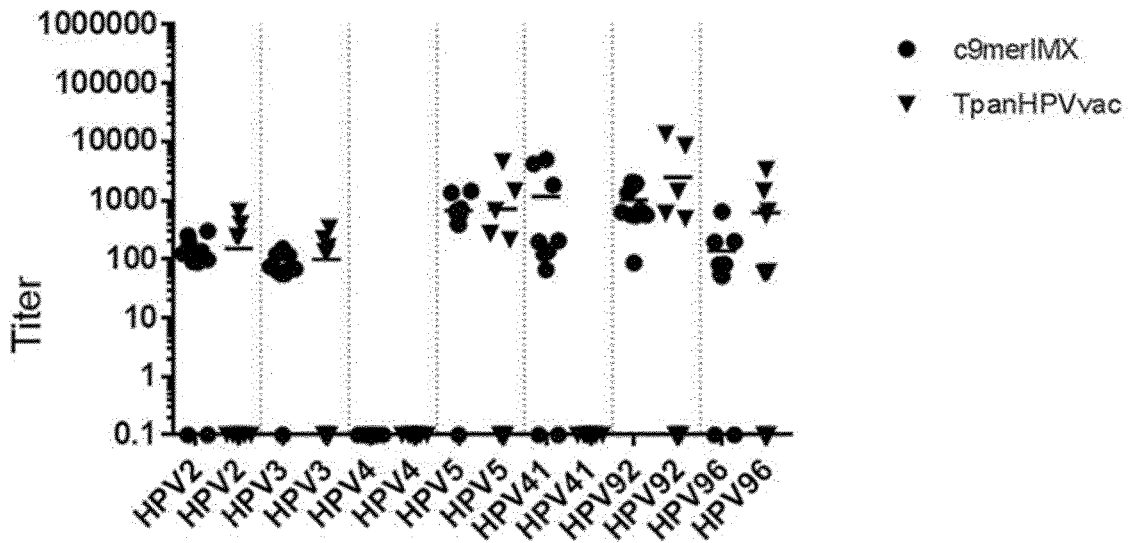

FIG. 5: The candidates c6mer.IMX and c9mer.IMX induce a robuster neutralizing protection against cutaneous HPVs than the TpanHPVvac vaccine. Each dot or triangle represents a single mouse; geometric 520 means of the titers for each group (10 animals) are indicated by horizontal lines. The y-axis displays EC50 titers. Shown is a comparison of the titers induced by c6mer.IMX (A) and c9mer.IMX (B) with the ones obtained with TpanHPVvac.

Figure 6:
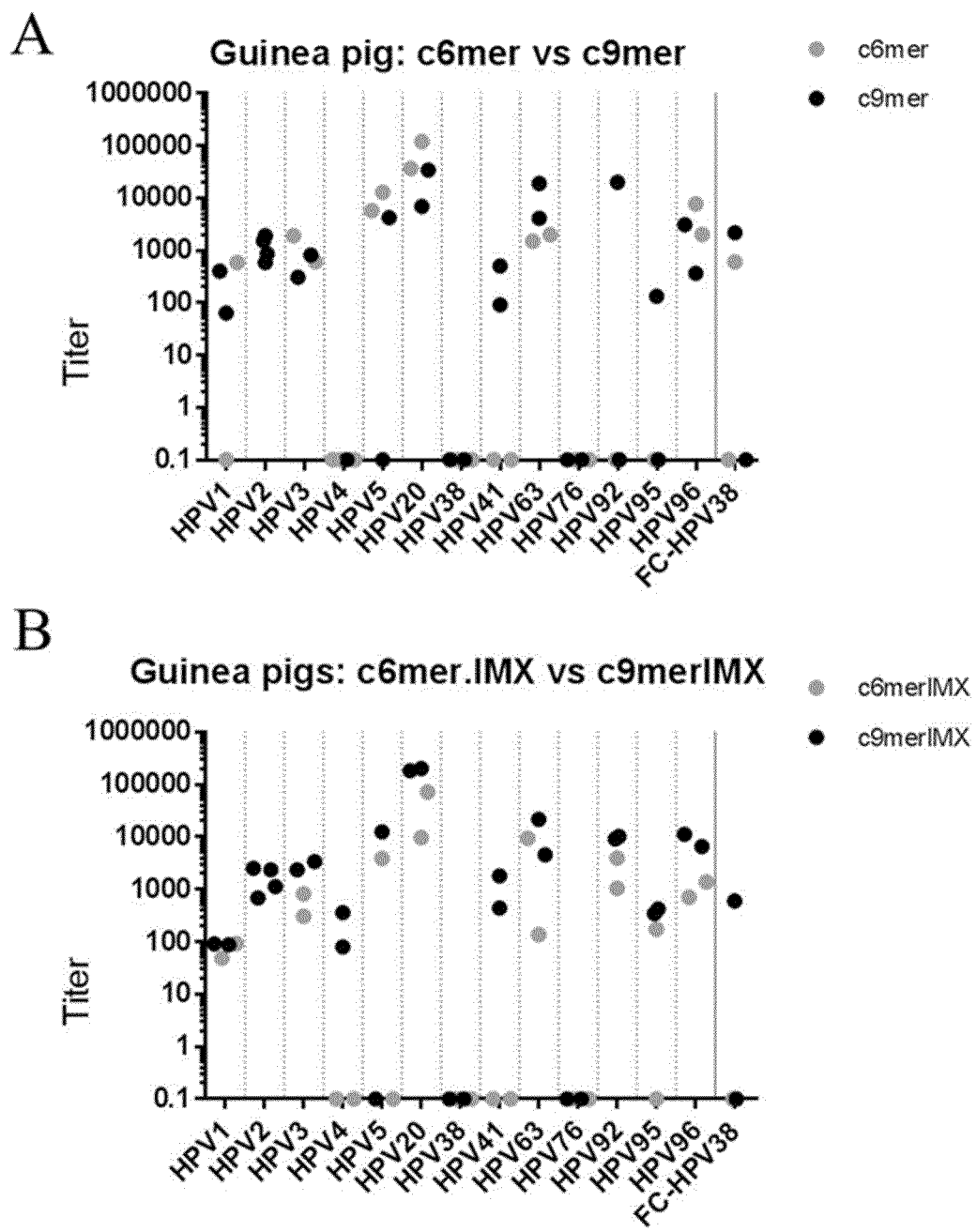

FIG. 6: A broad neutralization pattern was achieved for both candidate vaccines in guinea pigs, independently of the IMX domain. Each dot represents a single guinea pig for each group (2 animals). The y-axis displays EC50 titers. Shown are titers in the absence (A) and presence (B) of the IMX heptamerization domain.

The following Examples shall merely illustrate the invention. They shall not be construed, whatsoever, to limit the scope of the invention.

Example 1: Generation of Immunogens and Immunization

Constructs as indicated were obtained by standard recombinant DNA techniques and molecular cloning according to methods known from textbooks, followed by production in *E. coli* and purification as described herein below. Immunogenic polypeptides were obtained essentially as described earlier (WO 2010/070052), and as described herein below.

Immunization was performed in the two animal models, mice and guinea pigs. Animals were divided into two groups, each containing 10 BALB/c mice and 1 guinea pig. One group was immunized with the c6mer antigen, the other one with c9mer antigen. In both species, 50% Addavax were used as adjuvant. Mice were immunized with 20 μg antigen in a final volume of 50 μl intramuscularly, whereas guinea pig immunization was performed by using 30 μg antigen in a final volume of 200 μl subcutaneously. Immunization schedule was: Primary imunization at time=0, followed by boosts at weeks 2, 4, and 6, and collecting blood at week 10. Blood samples were collected by heart puncture. The samples were centrifuged twice for 15 minutes each in order to get rid of blood cells and the serum was transferred to a new tube. Longterm storage was done at −80° C., short-term storage at 4° C.

Example 2: Pseudovirion-Based Neutralization Assays

Pseudovirion-based neutralization assays (PBNAs) were performed essentially as described in WO 2011/151335. Briefly, 50 μl of diluted serum was combined with 50 μl of diluted pseudovirion and incubated at room temperature for 20 min. Next, 50 μl of HeLa T cells ($2.5 \times 10^5$ cells/ml) was added to the pseudovirion-antibody mixture and incubated for 48 h at 37° C. humidified incubator. The amount of secreted *Gaussia* luciferase was determined in 10 μl of cell culture medium using the *Gaussia* glow juice kit (PJK, Germany) according to the manufacturer's instructions. The light emissions of samples were measured 15 minutes after substrate addition. Results of L1 PBNAs are shown in FIGS. 2A and C (guinea pig), and in FIG. 3 (mice).

For the L2-enhanced pseudovirion-based neutralization assay (L2-PBNA), which has essentially the same sensitivity for anti-L1 antibodies, but a strongly increased sensitivity to anti-L2 antibodies, the PBNA was modified essentially as described in Day et al. (2012), Clinical and Vaccine Immunology 19(7):1075. Briefly, in the L2-PBNA, HPV pseudovirions are bound to extracellular matrix and treated with furin, which causes better exposure of L2. Only after this treatment, the actual PBNA is performed. Results of the L2-PBNA with guinea pig sera are shown in FIG. 2B.

Example 4: Experiments Relating to FIGS. 4 to 6

Protein expression and purification: Synthetic genes encoding the PfTrx-cHPVL2.c6mer, PfTrx-cHPVL2.c9mer, PfTrx-cHPVL2.c6mer.IMX and PfTrx-cHPVL2.c9mer.IMX (respectively referred as c6mer, c9mer, c6mer.IMX and c9mer.IMX) candidate vaccines were purchased from GenScript Cia, cloned into pET26 plasmid and further employed for expression in *Escherichia coli* BL21 cells. Purification of the c6mer and c9mer candidates was performed by using a one-step thermal purification protocol (Canali et al., 2014), whereas c6mer.IMX and c9merIMX were subjected to an ion exchange chromatography due to an arginine-rich motif at the C-terminus of the IMX heptamerization domain (OligoDOM technology). Concentration and quality of the proteins were monitored by SDS-PAGE/Coomassie-blue staining. Prior to immunization, both proteins were detoxified twice by the Triton X-114 method so that endotoxin levels were lower than 8 IU/ml. A detailed description of the purification method was recently reported by Spagnoli et al. (2017).

Mouse and guinea pig immunization: Four groups of 6-8 weeks old female Balbc mice (10 animals per group) were purchased from Charles River Laboratories and kept under specific pathogen-free conditions (animal permit G248/16). The candidate vaccines were adjuvated with 50% (v/v) Addavax (Invivogen) and administered intra-muscularly as reported by Pouyanfard et al. (2017). A fifth group of mice was immunized with the TpanHPVvac vaccine (Pouyanfard et al., 2017) currently undergoing clinical trial, following the same immunization protocol already mentioned. Four groups of outbred Hartley (Crl:HA) 150-200 g female guinea pigs (2 animals per group) also obtained from Charles River Laboratories (animal permit A2/17) were immunized with the candidate vaccines as reported by Pouyanfard et al. (2017). In all cases, the final blood samples were collected four weeks after the last immunization by heart puncture and the sera were obtained following centrifugation of clotted blood at 3500 rpm for 15 minutes at 4° C.

Pseudovirion (PsV) preparation: The different PsV preparations employed here were produced by co-transfecting human fibroblast cell line 293TT with plasmids carrying humanized HPV L1 and L2 coding sequences plus a reporter plasmid encoding the *Gaussia*-luciferase protein (GLuc). PsV particles were further purified by iodixanol gradient ultracentrifugation and therefore characterized by a transduction assay in HeLaT cells as reported previously Seitz et al. (2013).

In vitro standard Pseudovirion-based Neutralization Assay (PBNA): Except for HPV38, the neutralizing titers in the animal sera were characterized by the standard PBNA only. Briefly, a 96-well tissue culture polystyrene plate (Falcon, Germany) was prepared with 50 μl of diluted serum (in Dulbecco modified Eagle medium [DMEM] from Sigma-Aldrich, Germany), in a starting dilution of 1:50 in the plate and then titrated out in 5 steps, 3× dilution each) combined with 50 μl of diluted PsV (in DMEM) and incubated at room temperature for 20 min. Next, 50 μl of HeLaT cells ($2.5 \times 10^5$ cells/ml) was added to the PsV-antibody mixture and incubated for 48 h at 37° C. in a humidified incubator. The amount of secreted GLuc was determined in 10 μl of cell culture medium using the *Gaussia* Glow Juice kit according to the manufacturer's instructions (PJK GmbH, Germany), in a 96-weel F-bottom LUMITRAC microplate (Greiner Bio-One, Germany). The light emissions of samples were measured in a microplate luminometer (Victor3Perkin Elmer) 15 min after substrate addition. The neutralizing antibody titers described here represent the IC50 and were calculated on the GraphPad Prism 7 software.

In vitro modified Neutralization Assay (FC-PBNA): Specifically for HPV38, the detection of neutralizing antibodies was also assessed by the furin-cleaved pseudovirions neutralization assay (FC-PBNA), which employs basically the same protocol already described but using PsV particles produced in a furin-overexpressing fibroblast cell line (293TT.F). In order to ensure that the furin-cleaved PsVs (fc-PsVs) were successfully produced in regard to the protease processing, these particles were then characterized by a transduction assay in furin-deficient cell line LoVoT (in addition to the HeLaT) previously to the FC-PBNA. A detailed workflow regarding the FC-PBNA was reported by Wang et al. (2015).

As shown in FIG. 4, coupling the c6mer (FIG. 4A) and c9mer (FIG. 4B) polytopes to the IMX heptamerization domain increases immunogenicity of candidate vaccines in mouse model. As shown in FIG. 4C, neutralizing titers induced by both candidate vaccines (coupled to the IMX domain) against each HPV type are compared pairwise and were found to be similar overall, but the c9mer polytope configuration additionally induced cross-neutralizing antibodies against HPV41.

As shown in FIG. 5, although no expressive difference is observed when comparing the titers induced by c6mer.IMX (FIG. 5A) and c9mer.IMX (FIG. 5B) with the ones obtained with TpanHPVvac, a vaccine developed for immunization against high-risk HPVs, the number of animals successfully immunized with the cutaneous candidate vaccines which reacts against HPV2, HPV3, HPV5 and HPV41 is consistently higher than those observed for TpanHPVvac (FIG. 5B).

As shown in FIG. 6, even in the absence of the IMX heptamerization domain (FIG. 6A), the neutralizing titers induced by both candidate vaccines in guinea pigs are much higher than those detected in mouse model. Coupling the candidate vaccines to the IMX domain (FIG. 6B) does not expressively enhance the immunogenicity of the candidates, but seems to favor a better performance for the c9mer configuration polytope.

NON-STANDARD LITERATURE CITED

Bernard et al., Virology 401, 70-79 (2010)
Canali et al. (2014), Scientific Reports 4, Art. No 4729:1
van Doorslaer et al., Trends Microbiol 19, 49-50; author reply 50-41 (2011);
Egawa & Doorbar (2017), Virus Res 231: 119
Giroglou et al., (2001), Vaccine, 19: 1783-1793
Hausen, J Natl Cancer Inst 93, 252-253 (2001).
Howley et al., Virology 479-480, 290-296 (2015).
Moretto et al. (2007), J Biol Chem, 282, 11436-11445
Munoz et al., Int J Cancer 111, 278-285 (2004)
Pfister, J Natl Cancer Inst Monogr, 52-56 (2003)
Pouyanfard et al. (2018), J Virol. 2018; 92:e01930
Roden et al., (2006), Nat Rev Cancer, 6: 753-763
Schmiedeskamp et al, (2006), Ann Pharmacother, 40: 1344-1352
Seitz et al. (2013), Clin Vaccine Immunol 20:1061-1069
Spagnoli et al. (2017), Scientific Reports 7:18000
Wieland et al., Curr Probl Dermatol 45, 154-165 (2014)
Wang et al. (2015), Curr Protoc Microbiol. 38: 14B.5.1-14B.5.26
WO 2007/062819 A2
WO 2010/070052
WO 2011/151335

The invention claimed is:

1. An immunogenic polypeptide comprising a multitude of papillomavirus (PV) L2 N-terminal peptides consisting of amino acid sequences corresponding to amino acids 20 to 50 or amino acids 20 to 38 of the L2 polypeptide of HPV16 based on optimized sequence alignment,
   wherein the PV L2 N-terminal peptides are L2 N-terminal peptides from at least six different cutaneous HPV genotypes,
   wherein the PV L2 N-terminal peptides comprise L2 N-terminal peptides of cutaneous HPV genotypes 1a, 2a, 3, and 4 or variants thereof comprising at most two amino acid substitutions per PV L2 N-terminal peptide,
   wherein the PV L2 N-terminal peptides further comprise L2 N-terminal peptides of cutaneous HPV genotypes of at least two of HPV 5, 6, 9, 10, 39, 41, 63, 69, 88, and 95 or variants thereof comprising at most two amino acid substitutions per PV L2 N-terminal peptide, and
   wherein the multitude of PV L2 N-terminal peptides comprises an amino acid sequence comprising amino acids 1 to 85 of SEQ ID NO: 35 or a sequence at least 90% identical thereto.

2. The immunogenic polypeptide of claim 1, wherein the PV L2 N-terminal peptides are from human papillomaviruses (HPVs).

3. The immunogenic polypeptide of claim 1, wherein the PV L2 N-terminal peptides comprise L2 N-terminal peptides of
   (i) cutaneous HPV genotypes 1a, 2a, 3, 4, 10, and 63;
   (ii) cutaneous HPV genotypes 1a, 2a, 3, 4, 10, 41, 63, 88, and 95;
   (iii) cutaneous HPV genotypes 1a, 2a, 3, 4, 5, 6, 41, 88;
   (iv) cutaneous HPV genotypes 1a, 2a, 3, 4, 5, 6, 9, 10, 41, 88;
   (v) cutaneous HPV genotypes 1a, 2a, 3, 4, 5, 6, 9, 10, 41, 69, 88, and 95;
   (vi) HPV genotypes 1a, 2a, 3, 4, 5, 6, 9, 10, 31, 41, 51, 69, 88, and 95; or
   (vii) HPV genotypes 1a, 2a, 3, 4, 5, 6, 9, 10, 18, 31, 39, 41, 51, 69, 88, and 95.

4. The immunogenic polypeptide of claim 1, wherein the multitude of PV L2 N-terminal peptides comprises any one of SEQ ID NOs: 35 to 41 or is a variant of said immunogenic polypeptide comprising at most two amino acid substitutions per PV L2 N-terminal peptide.

5. The immunogenic polypeptide of claim 1, further comprising an oligomerization domain.

6. The immunogenic polypeptide of claim 1, wherein the multitude of PV L2 N-terminal peptides is comprised in a thioredoxin polypeptide.

7. A method of vaccinating a subject against HPV infection comprising:
   (a) contacting the subject with the immunogenic polypeptide of claim 1, a polynucleotide encoding the immunogenic polypeptide of claim 1, a vector comprising a polynucleotide encoding the immunogenic polypeptide of claim 1, and/or a host cell comprising the immunogenic polypeptide of claim 1, a polynucleotide encoding the immunogenic polypeptide of claim 1, or a vector comprising a polynucleotide encoding the immunogenic polypeptide of claim 1, and
   (b) thereby, vaccinating the subject against HPV infection.

8. The method of claim 7, wherein the subject is planned to be or is under immune suppression.

9. A polynucleotide encoding the immunogenic polypeptide according to claim 1.

10. A method for producing antibodies against a PV L2 polypeptide, comprising:
    (a) contacting a subject with an immunogenic polypeptide according to claim 1, and
    (b) harvesting antibodies generated by the subject from a bodily fluid of the subject and/or harvesting cells producing the antibodies from the subject.

11. The immunogenic polypeptide of claim 1, wherein the L2 N-terminal peptides of cutaneous HPV genotypes 1a, 2a, 3, and 4 or variants thereof comprise at most one amino acid substitution per PV L2 N-terminal peptide.

12. The immunogenic polypeptide of claim 1, wherein the L2 N-terminal peptides of cutaneous HPV genotypes of at least two of HPV 5, 6, 9, 10, 39, 41, 63, 69, 88, and 95 or variants thereof comprise at most one amino acid substitution per PV L2 N-terminal peptide.

13. The immunogenic polypeptide of claim 4, wherein the variant of said immunogenic polypeptide comprises at most one amino acid substitution per PV L2 N-terminal peptide.

14. The immunogenic polypeptide of claim 5, wherein the oligomerization domain comprises at least one of:
   (i) an oligomerization domain of a C4-binding protein;
   (ii) an encapsulin polypeptide;
   (iii) a ferritin polypeptide; and
   (iv) a hybrid polypeptide of two different chicken C4-binding proteins.

15. The immunogenic polypeptide of claim 6, wherein the multitude of PV L2 N-terminal peptides is comprised in a thioredoxin polypeptide of *Pyrococcus furiosus*.

16. The method of claim 8, wherein the subject is a future organ transplant recipient.

17. The immunogenic polypeptide of claim 14, wherein the oligomerization domain comprises an oligomerization domain of a mammalian C4-binding protein.

18. The immunogenic polypeptide of claim 14, wherein the oligomerization domain comprises an oligomerization domain of a human or mouse C4-binding protein.

19. The immunogenic polypeptide of claim 14, wherein the oligomerization domain comprises an encapsulin polypeptide from a *thermophilicarchae bacterium*.

20. The immunogenic polypeptide of claim 14, wherein the oligomerization domain comprises a *Pyrococcus furiosus* encapsulin polypeptide.

21. The immunogenic polypeptide of claim 14, wherein the oligomerization domain comprises a ferritin polypeptide from a thermophilic archaebacterium.

22. The immunogenic polypeptide of claim 14, wherein the oligomerization domain comprises a *Pyrococcus furiosus* ferritin polypeptide.

23. The immunogenic polypeptide of claim 14, wherein the oligomerization domain comprises an IMX313T polypeptide.

24. The immunogenic polypeptide of claim 1, wherein the multitude of PV L2 N-terminal peptides comprises an amino acid sequence comprising amino acids 1 to 85 of SEQ ID NO: 35.

25. The immunogenic polypeptide of claim 1, wherein the PV L2 N-terminal peptides further comprise L2 N-terminal peptides of cutaneous HPV genotypes of at least two of HPV 41, 88, and 95 or variants thereof comprising at most two amino acid substitutions per PV L2 N-terminal peptide.

26. The immunogenic polypeptide of claim 1, wherein the PV L2 N-terminal peptides are L2 N-terminal peptides from at least twelve different cutaneous HPV genotypes.

27. The immunogenic polypeptide of claim 5, wherein the oligomerization domain comprises an amino acid sequence as set forth in SEQ ID NO: 55.

28. The immunogenic polypeptide of claim 6, wherein the thioredoxin polypeptide comprises an *archaebacterial thioredoxin* polypeptide from a thermophilic archaebacterium.

29. The immunogenic polypeptide of claim 6, wherein the thioredoxin polypeptide comprises a thioredoxin polypeptide of *Pyrococcus furiosus* or of *Methanosaeta thermophila*.

* * * * *

SEQUENCE LISTING

<160> NUMBER OF SEQ ID NOS: 67

<210> SEQ ID NO 1
<211> LENGTH: 507
<212> TYPE: PRT
<213> ORGANISM: Human papillomavirus type 1a

<400> SEQUENCE: 1

Met Tyr Arg Leu Arg Arg Lys Arg Ala Ala Pro Lys Asp Ile Tyr Pro
1               5                   10                  15

Ser Cys Lys Ile Ser Asn Thr Cys Pro Pro Asp Ile Gln Asn Lys Ile
            20                  25                  30

Glu His Thr Thr Ile Ala Asp Lys Ile Leu Gln Tyr Gly Ser Leu Gly
        35                  40                  45

Val Phe Leu Gly Gly Leu Gly Ile Gly Thr Ala Arg Gly Ser Gly Gly
    50                  55                  60

Arg Ile Gly Tyr Thr Pro Leu Gly Glu Gly Gly Gly Val Arg Val Ala
65                  70                  75                  80

Thr Arg Pro Thr Pro Val Arg Pro Thr Ile Pro Val Glu Thr Val Gly
                85                  90                  95

Pro Ser Glu Ile Phe Pro Ile Asp Val Val Asp Pro Thr Gly Pro Ala
            100                 105                 110

Val Ile Pro Leu Gln Asp Leu Gly Arg Asp Phe Pro Ile Pro Thr Val
        115                 120                 125

Gln Val Ile Ala Glu Ile His Pro Ile Ser Asp Ile Pro Asn Ile Val
    130                 135                 140

Ala Ser Ser Thr Asn Glu Gly Glu Ser Ala Ile Leu Asp Val Leu Gln

```
            145                 150                 155                 160
        Gly Ser Ala Thr Ile Arg Thr Val Ser Arg Thr Gln Tyr Asn Asn Pro
                        165                 170                 175

Ser Phe Thr Val Ala Ser Thr Asn Ile Ser Ala Gly Glu Ala Ser
                        180                 185                 190

Thr Ser Asp Ile Val Phe Val Ser Asn Gly Ser Gly Asp Arg Val Val
                        195                 200                 205

Gly Glu Asp Ile Pro Leu Val Glu Leu Asn Leu Gly Leu Glu Thr Asp
                        210                 215                 220

Thr Ser Ser Val Val Gln Glu Thr Ala Phe Ser Ser Ser Thr Pro Ile
        225                 230                 235                 240

Ala Glu Arg Pro Ser Phe Arg Pro Ser Arg Phe Tyr Asn Arg Leu
                        245                 250                 255

Tyr Glu Gln Val Gln Val Gln Asp Pro Arg Phe Val Glu Gln Pro Gln
                        260                 265                 270

Ser Met Val Thr Phe Asp Asn Pro Ala Phe Glu Pro Glu Leu Asp Glu
                        275                 280                 285

Val Ser Ile Ile Phe Gln Arg Asp Leu Asp Ala Leu Ala Gln Thr Pro
                        290                 295                 300

Val Pro Glu Phe Arg Asp Val Val Tyr Leu Ser Lys Pro Thr Phe Ser
        305                 310                 315                 320

Arg Glu Pro Gly Gly Arg Leu Arg Val Ser Arg Leu Gly Lys Ser Ser
                        325                 330                 335

Thr Ile Arg Thr Arg Leu Gly Thr Ala Ile Gly Ala Arg Thr His Phe
                        340                 345                 350

Phe Tyr Asp Leu Ser Ser Ile Ala Pro Glu Asp Ser Ile Glu Leu Leu
                        355                 360                 365

Pro Leu Gly Glu His Ser Gln Thr Thr Val Ile Ser Ser Asn Leu Gly
                        370                 375                 380

Asp Thr Ala Phe Ile Gln Gly Glu Thr Ala Glu Asp Leu Glu Val
        385                 390                 395                 400

Ile Ser Leu Glu Thr Pro Gln Leu Tyr Ser Glu Glu Leu Leu Asp
                        405                 410                 415

Thr Asn Glu Ser Val Gly Glu Asn Leu Gln Leu Thr Ile Thr Asn Ser
                        420                 425                 430

Glu Gly Glu Val Ser Ile Leu Asp Leu Thr Gln Ser Arg Val Arg Pro
                        435                 440                 445

Pro Phe Gly Thr Glu Asp Thr Ser Leu His Val Tyr Tyr Pro Asn Ser
                        450                 455                 460

Ser Lys Gly Thr Pro Ile Ile Asn Pro Glu Glu Ser Phe Thr Pro Leu
        465                 470                 475                 480

Val Ile Ile Ala Leu Asn Asn Ser Thr Gly Asp Phe Glu Leu His Pro
                        485                 490                 495

Ser Leu Arg Lys Arg Arg Lys Arg Ala Tyr Val
                        500                 505

<210> SEQ ID NO 2
<211> LENGTH: 524
<212> TYPE: PRT
<213> ORGANISM: Human papillomavirus type 2a

<400> SEQUENCE: 2

Met Ser Val Gly Asp Ser Tyr Pro Asn Arg Leu Phe Ile Val Asp Val
1               5                   10                  15
```

```
Leu Cys Pro Phe Val Lys Pro His Leu Thr Pro Pro Leu Phe Tyr Ile
             20                  25                  30
Val Leu Ile His Phe His Phe Asp Thr Phe Val Phe Leu Tyr Leu
         35                  40                  45
Leu Arg Phe Asn Lys Arg Ala Thr Met Ser Ile Arg Ala Lys Arg Arg
 50                  55                  60
Lys Arg Ala Ser Pro Thr Asp Leu Tyr Arg Thr Cys Lys Gln Ala Gly
 65                  70                  75                  80
Thr Cys Pro Pro Asp Ile Ile Pro Arg Val Glu Gln Asn Thr Leu Ala
             85                  90                  95
Asp Lys Ile Leu Lys Trp Gly Ser Leu Gly Val Phe Phe Gly Gly Leu
            100                 105                 110
Gly Ile Gly Thr Gly Ser Gly Thr Gly Gly Arg Thr Gly Tyr Ile Pro
            115                 120                 125
Val Gly Ser Arg Pro Thr Thr Val Asp Ile Gly Pro Thr Pro Arg
            130                 135                 140
Pro Pro Val Ile Ile Glu Pro Val Gly Ala Ser Glu Pro Ser Ile Val
145                 150                 155                 160
Thr Leu Val Glu Asp Ser Ser Ile Ile Asn Ala Gly Ala Ser His Pro
                165                 170                 175
Thr Phe Thr Gly Thr Gly Gly Phe Glu Val Thr Thr Ser Thr Val Thr
                180                 185                 190
Asp Pro Ala Val Leu Asp Ile Thr Pro Ser Gly Thr Ser Val Gln Val
            195                 200                 205
Ser Ser Ser Ser Phe Leu Asn Pro Leu Tyr Thr Glu Pro Ala Ile Val
210                 215                 220
Glu Ala Pro Gln Thr Gly Glu Val Ser Gly His Val Leu Val Ser Thr
225                 230                 235                 240
Ala Thr Ser Gly Ser His Gly Tyr Glu Glu Ile Pro Met Gln Thr Phe
                245                 250                 255
Ala Thr Ser Gly Gly Ser Gly Thr Glu Pro Ile Ser Ser Thr Pro Leu
            260                 265                 270
Pro Gly Val Arg Arg Val Ala Gly Pro Arg Leu Tyr Ser Arg Ala Asn
            275                 280                 285
Gln Gln Val Gln Val Arg Asp Pro Ala Phe Leu Ala Arg Pro Ala Asp
290                 295                 300
Leu Val Thr Phe Asp Asn Pro Val Tyr Asp Pro Glu Glu Thr Ile Ile
305                 310                 315                 320
Phe Gln His Pro Asp Leu His Glu Pro Pro Asp Pro Asp Phe Leu Asp
                325                 330                 335
Ile Val Ala Leu His Arg Pro Ala Leu Thr Ser Arg Arg Gly Thr Val
                340                 345                 350
Arg Phe Ser Arg Leu Gly Arg Arg Ala Thr Leu Arg Thr Arg Ser Gly
            355                 360                 365
Lys Gln Ile Gly Ala Arg Val His Phe Tyr His Asp Ile Ser Pro Ile
            370                 375                 380
Gly Thr Glu Glu Leu Glu Met Glu Pro Leu Leu Pro Pro Ala Ser Thr
385                 390                 395                 400
Asp Asn Thr Asp Met Leu Tyr Asp Val Tyr Ala Asp Ser Asp Val Leu
                405                 410                 415
Gln Pro Leu Leu Asp Glu Leu Pro Ala Ala Pro Arg Gly Ser Leu Ser
            420                 425                 430
Leu Ala Asp Thr Ala Val Ser Ala Thr Ser Ala Ser Thr Leu Arg Gly
```

|     | 435 |     |     |     | 440 |     |     |     | 445 |     |     |
|-----|-----|-----|-----|-----|-----|-----|-----|-----|-----|-----|-----|

Ser Thr Thr Val Pro Leu Ser Ser Gly Ile Asp Val Pro Val Tyr Thr
            450                 455                 460

Gly Pro Asp Ile Glu Pro Pro Asn Val Pro Gly Met Gly Pro Leu Ile
465                 470                 475                 480

Pro Val Ala Pro Ser Leu Pro Ser Ser Val Tyr Ile Phe Gly Gly Asp
                485                 490                 495

Tyr Tyr Leu Met Pro Ser Tyr Val Leu Trp Pro Lys Arg Arg Lys Arg
            500                 505                 510

Val His Tyr Phe Phe Ala Asp Gly Phe Val Ala Ala
            515                 520

<210> SEQ ID NO 3
<211> LENGTH: 473
<212> TYPE: PRT
<213> ORGANISM: Human papillomavirus type 3

<400> SEQUENCE: 3

Met Val Ala His Arg Ala Arg Arg Arg Lys Arg Ala Ser Ala Thr Gln
1               5                   10                  15

Leu Tyr Arg Thr Cys Lys Ala Ala Gly Thr Cys Pro Pro Asp Val Ile
            20                  25                  30

Pro Lys Val Glu Gly Thr Thr Leu Ala Asp Arg Ile Leu Gln Trp Gly
        35                  40                  45

Ser Leu Gly Val Tyr Leu Gly Gly Leu Gly Ile Gly Thr Gly Ser Gly
    50                  55                  60

Thr Gly Gly Arg Thr Gly Tyr Ala Pro Ile Ser Thr Arg Pro Gly Thr
65                  70                  75                  80

Val Val Asp Val Ser Val Pro Ala Lys Pro Pro Val Val Ile Glu Pro
                85                  90                  95

Val Gly Pro Ser Asp Pro Ser Ile Val Asn Leu Leu Glu Asp Ser Ser
            100                 105                 110

Ile Ile Asn Ser Gly Ser Thr Ile Pro Thr Phe Thr Gly Thr Asp Gly
        115                 120                 125

Phe Glu Val Ile Ser Ser Ala Thr Thr Thr Pro Ala Val Leu Asp Ile
    130                 135                 140

Thr Pro Ala Ser Asp Asn Val Val Val Ser Ser Thr Asn Phe Ser Asn
145                 150                 155                 160

Pro Ala Phe Thr Glu Pro Ser Leu Leu Glu Val Pro Gln Asn Gly Glu
                165                 170                 175

Val Ser Gly His Ile Leu Ile Ser Thr Pro Thr Ser Gly Thr His Gly
            180                 185                 190

Tyr Glu Glu Ile Pro Met Glu Thr Phe Ala Ser Pro Gly Thr Gly Thr
        195                 200                 205

Glu Pro Ile Ser Ser Thr Pro Val Pro Gly Val Ser Arg Ile Ala Gly
    210                 215                 220

Pro Arg Leu Tyr Ser Lys Ala Val Thr Gln Val Lys Val Thr Asp Pro
225                 230                 235                 240

Ala Phe Leu Thr Arg Pro Arg Ser Leu Met Thr Phe Asp Asn Pro Val
                245                 250                 255

Phe Glu Pro Glu Asp Glu Thr Ile Ile Phe Glu Arg Pro Tyr Ser Pro
            260                 265                 270

Ser Gln Val Pro Asp Ser Asp Phe Leu Asp Ile Leu Arg Leu His Arg
        275                 280                 285

```
Pro Ala Leu Thr Ser Arg Arg Gly Thr Val Arg Tyr Ser Arg Val Gly
    290                 295                 300

Gln Lys Leu Ser Met Arg Thr Arg Ser Gly Lys Gly Leu Gly Ala Arg
305                 310                 315                 320

Val His Tyr Tyr Gln Asp Leu Ser Pro Ile Gly Pro Thr Glu Asp Ile
                325                 330                 335

Glu Met Glu Pro Leu Ile Ala Pro Ala Ser Ala Ser Ala Tyr Asp Ser
            340                 345                 350

Leu Tyr Asp Val Tyr Ala Asp Val Asp Ala Asp Ile Gly Phe Thr
        355                 360                 365

Ser Gly Gly Arg Ser Asp Thr Leu Ser Arg Gly Arg Ala Thr Val Ser
    370                 375                 380

Pro Leu Ser Ser Thr Leu Ser Thr Lys Tyr Gly Asn Val Thr Ile Pro
385                 390                 395                 400

Phe Val Ser Pro Val Asp Val Pro Leu Gln Pro Gly Pro Asp Ile Leu
                405                 410                 415

Leu Pro Ala Ser Ala Gln Trp Pro Phe Val Pro Leu Ser Pro Val Asp
            420                 425                 430

Thr Thr His Tyr Val Tyr Ile Asp Gly Gly Asp Phe Tyr Leu Trp Pro
        435                 440                 445

Val Thr Phe Phe Leu Pro Arg Arg Arg Arg Lys Arg Val Ser Tyr
    450                 455                 460

Phe Leu Ala Asp Gly Thr Val Ala Leu
465                 470

<210> SEQ ID NO 4
<211> LENGTH: 521
<212> TYPE: PRT
<213> ORGANISM: Human papillomavirus type 4

<400> SEQUENCE: 4

Met Gln Ser Leu Ser Arg Arg Lys Arg Asp Ser Val Pro Asn Leu Tyr
1               5                   10                  15

Ala Lys Cys Gln Leu Ser Gly Asn Cys Leu Pro Asp Val Lys Asn Lys
            20                  25                  30

Val Glu Ala Asp Thr Leu Ala Asp Arg Leu Leu Arg Trp Leu Gly Ser
        35                  40                  45

Val Ile Tyr Leu Gly Gly Leu Gly Ile Gly Thr Gly Arg Gly Ser Gly
    50                  55                  60

Gly Ser Thr Gly Tyr Asn Pro Ile Gly Ala Pro Ser Arg Val Thr Pro
65                  70                  75                  80

Ser Gly Thr Leu Val Arg Pro Thr Val Pro Val Glu Ser Leu Gly Pro
                85                  90                  95

Ser Glu Ile Ile Pro Ile Asp Ala Ile Asp Pro Thr Thr Ser Ser Val
            100                 105                 110

Val Pro Leu Glu Asp Leu Thr Ile Pro Asp Val Thr Val Asp Ser Gly
        115                 120                 125

Asp Thr Arg Gly Ile Gly Glu Thr Thr Leu Gln Pro Ala Gln Val Asp
    130                 135                 140

Ile Ser Thr Ser His Asp Pro Ile Ser Asp Val Thr Gly Ala Ser Ser
145                 150                 155                 160

His Pro Thr Ile Ile Ser Gly Glu Asp Asn Ala Ile Ala Val Leu Asp
                165                 170                 175

Val Ser Pro Ile Glu Pro Pro Thr Lys Arg Ile Ala Leu Ala Thr Arg
            180                 185                 190
```

```
Gly Ala Ser Ala Thr Pro His Val Ser Val Ile Ser Gly Thr Thr Glu
            195                 200                 205

Phe Gly Gln Ser Ser Asp Leu Asn Val Phe Val Asn Ala Thr Phe Ser
        210                 215                 220

Gly Asp Ser Ile Gly Tyr Thr Glu Ile Pro Leu Glu Pro Leu Asn
225                 230                 235                 240

Pro Phe Gln Glu Phe Glu Ile Glu Ser Pro Lys Thr Ser Thr Pro
                245                 250                 255

Arg Asp Val Leu Asn Arg Ala Ile Gly Arg Ala Arg Asp Leu Tyr Asn
                260                 265                 270

Arg Arg Val Gln Gln Ile Pro Thr Arg Asn Pro Ala Leu Leu Thr Gln
            275                 280                 285

Pro Ser Arg Ala Ile Val Phe Gly Phe Glu Asn Pro Ala Phe Asp Ala
        290                 295                 300

Asp Ile Thr Gln Thr Phe Glu Arg Asp Leu Glu Gln Val Ala Ala Ala
305                 310                 315                 320

Pro Asp Ala Asp Phe Ala Asp Ile Val Thr Ile Gly Arg Pro Arg Phe
                325                 330                 335

Ser Glu Thr Asp Ala Gly Gln Ile Arg Val Ser Arg Leu Gly Arg Arg
            340                 345                 350

Gly Thr Ile Lys Thr Arg Ser Gly Val Gln Ile Gly Gln Ala Val His
        355                 360                 365

Phe Tyr Tyr Asp Leu Ser Thr Ile Asp Thr Ala Asp Ala Ile Glu Leu
    370                 375                 380

Ser Thr Leu Gly Gln His Ser Gly Glu Gln Ser Ile Val Asp Ala Met
385                 390                 395                 400

Ile Glu Ser Ser Leu Ile Asp Pro Phe Glu Met Pro Asp Pro Thr Phe
                405                 410                 415

Thr Glu Glu Gln Gln Leu Leu Asp Pro Leu Thr Glu Asp Phe Ser Gln
            420                 425                 430

Ser His Leu Val Leu Thr Ser Arg Arg Gly Thr Ser Phe Thr Ile
        435                 440                 445

Pro Thr Ile Pro Pro Gly Leu Gly Leu Arg Ile Tyr Val Asp Asp Val
    450                 455                 460

Gly Ser Asp Leu Phe Val Ser Tyr Pro Glu Ser Arg Val Ile Pro Ala
465                 470                 475                 480

Gly Gly Leu Pro Thr Glu Pro Phe Val Pro Leu Glu Pro Ala Leu Leu
                485                 490                 495

Ser Asp Ile Phe Ser Thr Asp Phe Val Tyr Arg Pro Ser Leu Tyr Arg
            500                 505                 510

Lys Lys Arg Lys Arg Leu Glu Met Phe
        515                 520

<210> SEQ ID NO 5
<211> LENGTH: 518
<212> TYPE: PRT
<213> ORGANISM: Human papillomavirus type 5

<400> SEQUENCE: 5

Met Ala Arg Ala Lys Arg Val Lys Arg Asp Ser Val Thr His Ile Tyr
1               5                   10                  15

Gln Thr Cys Lys Gln Ala Gly Thr Cys Pro Pro Asp Val Ile Asn Lys
            20                  25                  30

Val Glu Gln Thr Thr Val Ala Asp Asn Ile Leu Lys Tyr Gly Ser Ala
```

```
                35                  40                  45
Gly Val Phe Phe Gly Gly Leu Gly Ile Ser Thr Gly Arg Gly Thr Gly
         50                  55                  60
Gly Ala Thr Gly Tyr Val Pro Leu Gly Glu Gly Pro Gly Val Arg Val
 65                  70                  75                  80
Gly Gly Thr Pro Thr Val Arg Pro Ser Leu Val Pro Glu Thr Ile
                 85                  90                  95
Gly Pro Val Asp Ile Leu Pro Ile Asp Thr Val Asn Pro Val Glu Pro
                100                 105                 110
Thr Ala Ser Ser Val Val Pro Leu Thr Glu Ser Thr Gly Ala Asp Leu
                115                 120                 125
Leu Pro Gly Glu Val Glu Thr Ile Ala Glu Ile His Pro Val Pro Glu
                130                 135                 140
Gly Pro Ser Val Asp Thr Pro Val Val Thr Thr Ser Thr Gly Ser Ser
145                 150                 155                 160
Ala Val Leu Glu Val Ala Pro Glu Pro Ile Pro Pro Thr Arg Val Arg
                165                 170                 175
Val Ser Arg Thr Gln Tyr His Asn Pro Ser Phe Gln Ile Ile Thr Glu
                180                 185                 190
Ser Thr Pro Ala Gln Gly Glu Ser Ser Leu Ala Asp His Val Leu Val
                195                 200                 205
Thr Ser Gly Ser Gly Gly Gln Arg Ile Gly Gly Asp Ile Thr Asp Ile
                210                 215                 220
Ile Glu Leu Glu Glu Ile Pro Ser Arg Tyr Thr Phe Glu Ile Glu Glu
225                 230                 235                 240
Pro Thr Pro Pro Arg Arg Ser Ser Thr Pro Leu Pro Arg Asn Gln Ser
                245                 250                 255
Val Gly Arg Arg Arg Gly Phe Ser Leu Thr Asn Arg Arg Leu Val Gln
                260                 265                 270
Gln Val Gln Val Asp Asn Pro Leu Phe Leu Thr Gln Pro Ser Lys Leu
                275                 280                 285
Val Arg Phe Ala Phe Asp Asn Pro Val Phe Glu Glu Glu Val Thr Asn
                290                 295                 300
Ile Phe Glu Asn Asp Leu Asp Val Phe Glu Glu Pro Pro Asp Arg Asp
305                 310                 315                 320
Phe Leu Asp Val Arg Glu Leu Gly Arg Pro Gln Tyr Ser Thr Thr Pro
                325                 330                 335
Ala Gly Tyr Val Arg Val Ser Arg Leu Gly Thr Arg Ala Thr Ile Arg
                340                 345                 350
Thr Arg Ser Gly Ala Gln Ile Gly Ser Gln Val His Phe Tyr Arg Asp
                355                 360                 365
Leu Ser Ser Ile Asn Thr Glu Asp Pro Ile Glu Leu Gln Leu Leu Gly
                370                 375                 380
Gln His Ser Gly Asp Ala Thr Ile Val His Gly Pro Val Glu Ser Thr
385                 390                 395                 400
Phe Ile Asp Met Asp Ile Ser Glu Asn Pro Leu Ser Glu Ser Ile Glu
                405                 410                 415
Ala Tyr Ser His Asp Leu Leu Leu Asp Glu Thr Val Glu Asp Phe Ser
                420                 425                 430
Gly Ser Gln Leu Val Ile Gly Asn Arg Arg Ser Thr Asn Ser Tyr Thr
                435                 440                 445
Val Pro Arg Phe Glu Thr Thr Arg Asn Gly Ser Tyr Tyr Thr Gln Asp
                450                 455                 460
```

```
Thr Lys Gly Tyr Tyr Val Ala Tyr Pro Glu Ser Arg Asn Asn Ala Glu
465                 470                 475                 480

Ile Ile Tyr Pro Thr Pro Asp Ile Pro Val Ile Ile His Pro His
            485                 490                 495

Asp Ser Thr Gly Asp Phe Tyr Leu His Pro Ser Leu His Arg Arg Lys
            500                 505                 510

Arg Lys Arg Lys Tyr Leu
        515

<210> SEQ ID NO 6
<211> LENGTH: 459
<212> TYPE: PRT
<213> ORGANISM: Human papillomavirus type 6

<400> SEQUENCE: 6

Met Ala His Ser Arg Ala Arg Arg Lys Arg Ala Ser Ala Thr Gln
1               5                   10                  15

Leu Tyr Gln Thr Cys Lys Leu Thr Gly Thr Cys Pro Pro Asp Val Ile
                20                  25                  30

Pro Lys Val Glu His Asn Thr Ile Ala Asp Gln Ile Leu Lys Trp Gly
            35                  40                  45

Ser Leu Gly Val Phe Phe Gly Gly Leu Gly Ile Gly Thr Gly Ser Gly
50                  55                  60

Thr Gly Gly Arg Thr Gly Tyr Val Pro Leu Gln Thr Ser Ala Lys Pro
65                  70                  75                  80

Ser Ile Thr Ser Gly Pro Met Ala Arg Pro Pro Val Val Val Glu Pro
                85                  90                  95

Val Ala Pro Ser Asp Pro Ser Ile Val Ser Leu Ile Glu Glu Ser Ala
            100                 105                 110

Ile Ile Asn Ala Gly Ala Pro Glu Ile Val Pro Pro Ala His Gly Gly
        115                 120                 125

Phe Thr Ile Thr Ser Ser Glu Thr Thr Thr Pro Ala Ile Leu Asp Val
    130                 135                 140

Ser Val Thr Ser His Thr Thr Thr Ser Ile Phe Arg Asn Pro Val Phe
145                 150                 155                 160

Thr Glu Pro Ser Val Thr Gln Pro Gln Pro Pro Val Glu Ala Asn Gly
                165                 170                 175

His Ile Leu Ile Ser Ala Pro Thr Val Thr Ser His Pro Ile Glu Glu
            180                 185                 190

Ile Pro Leu Asp Thr Phe Val Val Ser Ser Ser Asp Ser Gly Pro Thr
        195                 200                 205

Ser Ser Thr Pro Val Pro Gly Thr Ala Pro Arg Pro Arg Val Gly Leu
    210                 215                 220

Tyr Ser Arg Ala Leu His Gln Val Gln Val Thr Asp Pro Ala Phe Leu
225                 230                 235                 240

Ser Thr Pro Gln Arg Leu Ile Thr Tyr Asp Asn Pro Val Tyr Glu Gly
                245                 250                 255

Glu Asp Val Ser Val Gln Phe Ser His Asp Ser Ile His Asn Ala Pro
            260                 265                 270

Asp Glu Ala Phe Met Asp Ile Ile Arg Leu His Arg Pro Ala Ile Ala
        275                 280                 285

Ser Arg Arg Gly Leu Val Arg Tyr Ser Arg Ile Gly Gln Arg Gly Ser
    290                 295                 300

Met His Thr Arg Ser Gly Lys His Ile Gly Ala Arg Ile His Tyr Phe
```

-continued

```
                305                 310                 315                 320
        Tyr Asp Ile Ser Pro Ile Ala Gln Ala Ala Glu Glu Ile Glu Met His
                        325                 330                 335

Pro Leu Val Ala Ala Gln Asp Asp Thr Phe Asp Ile Tyr Ala Glu Ser
                        340                 345                 350

Phe Glu Pro Gly Ile Asn Pro Thr Gln His Pro Val Thr Asn Ile Ser
                        355                 360                 365

Asp Thr Tyr Leu Thr Ser Thr Pro Asn Thr Val Thr Gln Pro Trp Gly
                        370                 375                 380

Asn Thr Thr Val Pro Leu Ser Leu Pro Asn Asp Leu Phe Leu Gln Ser
        385                 390                 395                 400

Gly Pro Asp Ile Thr Phe Pro Thr Ala Pro Met Gly Thr Pro Phe Ser
                        405                 410                 415

Pro Val Thr Pro Ala Leu Pro Thr Gly Pro Val Phe Ile Thr Gly Ser
                        420                 425                 430

Gly Phe Tyr Leu His Pro Ala Trp Tyr Phe Ala Arg Lys Arg Arg Lys
                        435                 440                 445

Arg Ile Pro Leu Phe Phe Ser Asp Val Ala Ala
                        450                 455

<210> SEQ ID NO 7
<211> LENGTH: 533
<212> TYPE: PRT
<213> ORGANISM: Human papillomavirus type 9

<400> SEQUENCE: 7

Met Val Arg Ala Lys Arg Thr Lys Arg Ala Ser Val Thr Asp Ile Tyr
        1               5                   10                  15

Arg Gly Cys Lys Ala Ala Gly Thr Cys Pro Pro Asp Val Ile Asn Lys
                        20                  25                  30

Val Glu His Thr Thr Ile Ala Asp Lys Ile Leu Gln Tyr Gly Ser Ala
                        35                  40                  45

Gly Val Phe Phe Gly Gly Leu Gly Ile Ser Thr Gly Arg Gly Thr Gly
                50                  55                  60

Gly Ala Thr Gly Tyr Val Pro Leu Gly Glu Gly Pro Gly Val Arg Val
        65                  70                  75                  80

Gly Gly Thr Pro Thr Ile Val Arg Pro Gly Val Ile Pro Glu Ile Ile
                        85                  90                  95

Gly Pro Thr Asp Leu Ile Pro Leu Asp Thr Val Arg Pro Ile Asp Pro
                        100                 105                 110

Thr Ala Pro Ser Ile Val Thr Gly Thr Asp Ser Thr Val Asp Leu Leu
                        115                 120                 125

Pro Gly Glu Ile Glu Ser Ile Ala Glu Ile His Pro Val Pro Val Asp
                        130                 135                 140

Asn Ala Val Val Asp Thr Pro Val Val Thr Glu Gly Arg Arg Gly Ser
        145                 150                 155                 160

Ser Ala Ile Leu Glu Val Ala Asp Pro Ser Pro Met Arg Thr Arg
                        165                 170                 175

Val Ala Arg Thr Gln Tyr His Asn Pro Ala Phe Gln Ile Ile Ser Glu
                        180                 185                 190

Ser Thr Pro Met Ser Gly Glu Ser Ser Leu Ala Asp His Ile Ile Val
                        195                 200                 205

Phe Glu Gly Ser Gly Gly Gln Leu Val Gly Gly Pro Arg Glu Ser Tyr
                        210                 215                 220
```

```
Thr Ala Ser Ser Glu Asn Ile Glu Leu Gln Glu Phe Pro Ser Arg Tyr
225                 230                 235                 240

Ser Phe Glu Ile Asp Glu Gly Thr Pro Pro Arg Thr Ser Thr Pro Val
            245                 250                 255

Gln Arg Ala Val Gln Ser Leu Ser Ser Leu Arg Arg Ala Leu Tyr Asn
        260                 265                 270

Arg Arg Leu Thr Glu Gln Val Ala Val Thr Asp Pro Leu Phe Leu Ser
    275                 280                 285

Arg Pro Ser Arg Leu Val Gln Phe Gln Phe Asp Asn Pro Ala Phe Glu
290                 295                 300

Asp Glu Val Thr Gln Ile Phe Glu Arg Asp Leu Ser Thr Val Glu Glu
305                 310                 315                 320

Pro Pro Asp Arg Gln Phe Leu Asp Val Gln Arg Leu Ser Arg Pro Leu
            325                 330                 335

Tyr Thr Glu Thr Pro Gln Gly Tyr Val Arg Val Ser Arg Leu Gly Arg
        340                 345                 350

Arg Ala Thr Ile Arg Thr Arg Ser Gly Ala Gln Val Gly Ala Gln Val
    355                 360                 365

His Phe Tyr Arg Asp Leu Ser Thr Ile Asn Thr Glu Glu Pro Ile Glu
370                 375                 380

Met Gln Leu Leu Gly Glu His Ser Gly Asp Ser Thr Ile Val Gln Gly
385                 390                 395                 400

Pro Val Glu Ser Ser Ile Val Asp Val Asn Ile Asp Glu Pro Asp Gly
            405                 410                 415

Leu Glu Val Gly Arg Gln Glu Thr Pro Ser Val Glu Asp Val Asp Phe
        420                 425                 430

Asn Ser Glu Asp Leu Leu Leu Asp Glu Gly Val Glu Asp Phe Ser Gly
    435                 440                 445

Ser Gln Leu Val Val Gly Thr Arg Ser Thr Asn Thr Leu Thr Val
450                 455                 460

Pro Arg Phe Glu Thr Pro Arg Asp Thr Ser Phe Tyr Ile Gln Asp Ile
465                 470                 475                 480

Gln Gly Tyr Thr Val Ser Tyr Pro Glu Ser Arg Gln Thr Thr Asp Ile
            485                 490                 495

Ile Phe Pro His Pro Asp Thr Pro Thr Val Val Ile His Ile Asn Asp
        500                 505                 510

Thr Ser Gly Asp Tyr Tyr Leu His Pro Ser Leu Gln Arg Lys Lys Arg
    515                 520                 525

Lys Arg Lys Tyr Leu
530

<210> SEQ ID NO 8
<211> LENGTH: 470
<212> TYPE: PRT
<213> ORGANISM: Human papillomavirus type 10

<400> SEQUENCE: 8

Met Val Ala Gln Arg Ala Arg Arg Lys Arg Ala Ser Ala Thr Gln
1               5                   10                  15

Leu Tyr Arg Thr Cys Lys Ala Ser Gly Thr Cys Pro Pro Asp Val Ile
            20                  25                  30

Pro Lys Val Glu Gly Thr Thr Leu Ala Asp Arg Ile Leu Gln Trp Gly
        35                  40                  45

Ser Leu Gly Val Tyr Leu Gly Gly Leu Gly Ile Gly Thr Gly Ser Gly
    50                  55                  60
```

```
Thr Gly Gly Arg Thr Gly Tyr Val Pro Ile Ser Thr Arg Pro Gly Thr
 65                  70                  75                  80

Val Val Asp Val Ser Val Pro Ala Arg Pro Val Val Ile Glu Pro
                 85                  90                  95

Val Gly Pro Ser Asp Pro Ser Ile Val Asn Leu Leu Glu Asp Ser Ser
                100                 105                 110

Ile Ile Asn Ser Gly Ser Thr Ile Pro Thr Phe Ser Gly Thr Ser Gly
            115                 120                 125

Phe Glu Val Thr Ser Ser Ala Thr Thr Thr Pro Ala Val Leu Asp Ile
        130                 135                 140

Thr Pro Ala Ser Glu Asn Val Val Ile Ser Ser Thr Asn Phe Thr Asn
145                 150                 155                 160

Pro Ala Phe Thr Glu Pro Ser Leu Val Glu Val Pro Gln Ser Gly Glu
                165                 170                 175

Val Ser Gly His Ile Leu Ile Ser Thr Pro Thr Ala Gly Thr His Gly
                180                 185                 190

Tyr Glu Glu Ile Pro Met Asp Thr Phe Ala Ser Ser Gly Thr Gly Thr
            195                 200                 205

Glu Pro Ile Ser Ser Thr Pro Val Pro Gly Val Ser Arg Ile Ala Gly
        210                 215                 220

Pro Arg Leu Tyr Ser Arg Ala Asn Thr Gln Val Lys Val Ser Asp Pro
225                 230                 235                 240

Ala Phe Leu Ser Arg Pro Ser Ser Leu Leu Thr Phe Asp Asn Pro Val
                245                 250                 255

Phe Glu Pro Glu Asp Glu Thr Ile Ile Phe Glu Arg Pro Tyr Ser Pro
                260                 265                 270

Ser Arg Val Pro Asp Pro Asp Phe Leu Asp Ile Val Arg Leu His Arg
            275                 280                 285

Pro Ala Leu Thr Ser Arg Arg Gly Thr Val Arg Phe Ser Arg Leu Gly
        290                 295                 300

Gln Lys Phe Ser Met Arg Thr Arg Ser Gly Lys Gly Ile Gly Ala Arg
305                 310                 315                 320

Val His Tyr Tyr Gln Asp Leu Ser Pro Ile Ala Pro Ile Glu Asp Ile
                325                 330                 335

Glu Met Glu Pro Leu Leu Ala Pro Ala Ala Ser Asp Thr Ile Tyr Asp
                340                 345                 350

Ile Phe Ala Asp Val Asp Asp Gly Asp Val Ala Phe Thr Glu Gly Tyr
            355                 360                 365

Arg Ser Thr Thr Gln Ser Arg Gly Tyr Asn Thr Thr Ser Pro Leu Ser
        370                 375                 380

Ser Thr Leu Ser Thr Lys Tyr Gly Asn Val Thr Ile Pro Phe Val Ser
385                 390                 395                 400

Pro Val Asp Val Thr Leu His Thr Gly Pro Asp Ile Val Leu Pro Thr
                405                 410                 415

Ser Ala Gln Trp Pro Tyr Val Pro Leu Ser Pro Ala Asp Thr Thr His
                420                 425                 430

Tyr Val Tyr Ile Asp Gly Gly Asp Phe Tyr Leu Trp Pro Val Thr Phe
            435                 440                 445

His Phe Ser Arg His Arg Arg Lys Arg Val Ser Tyr Phe Phe Ala
        450                 455                 460

Asp Gly Thr Leu Ala Leu
465                 470
```

<210> SEQ ID NO 9
<211> LENGTH: 462
<212> TYPE: PRT
<213> ORGANISM: Human papillomavirus type 18

<400> SEQUENCE: 9

```
Met Val Ser His Arg Ala Ala Arg Arg Lys Arg Ala Ser Val Thr Asp
1               5                   10                  15

Leu Tyr Lys Thr Cys Lys Gln Ser Gly Thr Cys Pro Pro Asp Val Val
            20                  25                  30

Pro Lys Val Glu Gly Thr Thr Leu Ala Asp Lys Ile Leu Gln Trp Ser
        35                  40                  45

Ser Leu Gly Ile Phe Leu Gly Gly Leu Gly Ile Gly Thr Gly Ser Gly
    50                  55                  60

Thr Gly Gly Arg Thr Gly Tyr Ile Pro Leu Gly Gly Arg Ser Asn Thr
65                  70                  75                  80

Val Val Asp Val Gly Pro Thr Arg Pro Pro Val Val Ile Glu Pro Val
                85                  90                  95

Gly Pro Thr Asp Pro Ser Ile Val Thr Leu Ile Glu Asp Ser Ser Val
            100                 105                 110

Val Thr Ser Gly Ala Pro Arg Pro Thr Phe Thr Gly Thr Ser Gly Phe
        115                 120                 125

Asp Ile Thr Ser Ala Gly Thr Thr Thr Pro Ala Val Leu Asp Ile Thr
    130                 135                 140

Pro Ser Ser Thr Ser Val Ser Ile Ser Thr Thr Asn Phe Thr Asn Pro
145                 150                 155                 160

Ala Phe Ser Asp Pro Ser Ile Ile Glu Val Pro Gln Thr Gly Glu Val
                165                 170                 175

Ala Gly Asn Val Phe Val Gly Thr Pro Thr Ser Gly Thr His Gly Tyr
            180                 185                 190

Glu Glu Ile Pro Leu Gln Thr Phe Ala Ser Ser Gly Thr Gly Glu Glu
        195                 200                 205

Pro Ile Ser Ser Thr Pro Leu Pro Thr Val Arg Arg Val Ala Gly Pro
    210                 215                 220

Arg Leu Tyr Ser Arg Ala Tyr Gln Gln Val Ser Val Ala Asn Pro Glu
225                 230                 235                 240

Phe Leu Thr Arg Pro Ser Ser Leu Ile Thr Tyr Asp Asn Pro Ala Phe
                245                 250                 255

Glu Pro Val Asp Thr Thr Leu Thr Phe Asp Pro Arg Ser Asp Val Pro
            260                 265                 270

Asp Ser Asp Phe Met Asp Ile Ile Arg Leu His Arg Pro Ala Leu Thr
        275                 280                 285

Ser Arg Arg Gly Thr Val Arg Phe Ser Arg Leu Gly Gln Arg Ala Thr
    290                 295                 300

Met Phe Thr Arg Ser Gly Thr Gln Ile Gly Ala Arg Val His Phe Tyr
305                 310                 315                 320

His Asp Ile Ser Pro Ile Ala Pro Ser Pro Glu Tyr Ile Glu Leu Gln
                325                 330                 335

Pro Leu Val Ser Ala Thr Glu Asp Asn Asp Leu Phe Asp Ile Tyr Ala
            340                 345                 350

Asp Asp Met Asp Pro Ala Val Pro Val Pro Ser Arg Ser Thr Thr Ser
        355                 360                 365

Phe Ala Phe Phe Lys Tyr Ser Pro Thr Ile Ser Ser Ala Ser Ser Tyr
    370                 375                 380
```

```
Ser Asn Val Thr Val Pro Leu Thr Ser Ser Trp Asp Val Pro Val Tyr
385                 390                 395                 400

Thr Gly Pro Asp Ile Thr Leu Pro Ser Thr Thr Ser Val Trp Pro Ile
            405                 410                 415

Val Ser Pro Thr Ala Pro Ala Ser Thr Gln Tyr Ile Gly Ile His Gly
            420                 425                 430

Thr His Tyr Tyr Leu Trp Pro Leu Tyr Tyr Phe Ile Pro Lys Lys Arg
            435                 440                 445

Lys Arg Val Pro Tyr Phe Phe Ala Asp Gly Phe Val Ala Ala
450                 455                 460

<210> SEQ ID NO 10
<211> LENGTH: 466
<212> TYPE: PRT
<213> ORGANISM: Human papillomavirus type 31

<400> SEQUENCE: 10

Met Arg Ser Lys Arg Ser Thr Lys Arg Thr Lys Arg Ala Ser Ala Thr
1               5                   10                  15

Gln Leu Tyr Gln Thr Cys Lys Ala Ala Gly Thr Cys Pro Ser Asp Val
            20                  25                  30

Ile Pro Lys Ile Glu His Thr Thr Ile Ala Asp Gln Ile Leu Arg Tyr
            35                  40                  45

Gly Ser Met Gly Val Phe Phe Gly Gly Leu Gly Ile Gly Ser Gly Ser
            50                  55                  60

Gly Thr Gly Gly Arg Thr Gly Tyr Val Pro Leu Ser Thr Arg Pro Ser
65              70                  75                  80

Thr Val Ser Glu Ala Ser Ile Pro Ile Arg Pro Pro Val Ser Ile Asp
            85                  90                  95

Pro Val Gly Pro Leu Asp Pro Ser Ile Val Ser Leu Val Glu Glu Ser
            100                 105                 110

Gly Ile Val Asp Val Gly Ala Pro Ala Pro Ile Pro His Pro Pro Thr
            115                 120                 125

Thr Ser Gly Phe Asp Ile Ala Thr Thr Ala Asp Thr Thr Pro Ala Ile
            130                 135                 140

Leu Asp Val Thr Ser Val Ser Thr His Glu Asn Pro Thr Phe Thr Asp
145                 150                 155                 160

Pro Ser Val Leu Gln Pro Pro Thr Pro Ala Glu Thr Ser Gly His Leu
            165                 170                 175

Leu Leu Ser Ser Ser Ser Ile Ser Thr His Asn Tyr Glu Glu Ile Pro
            180                 185                 190

Met Asp Thr Phe Ile Val Ser Thr Asn Asn Glu Asn Ile Thr Ser Ser
            195                 200                 205

Thr Pro Ile Pro Gly Val Arg Arg Pro Ala Arg Leu Gly Leu Tyr Ser
            210                 215                 220

Lys Ala Thr Gln Gln Val Lys Val Ile Asp Pro Thr Phe Leu Ser Ala
225                 230                 235                 240

Pro Lys Gln Leu Ile Thr Tyr Glu Asn Pro Ala Tyr Glu Thr Val Asn
            245                 250                 255

Ala Glu Glu Ser Leu Tyr Phe Ser Asn Thr Ser His Asn Ile Ala Pro
            260                 265                 270

Asp Pro Asp Phe Leu Asp Ile Ile Ala Leu His Arg Pro Ala Leu Thr
            275                 280                 285

Ser Arg Arg Asn Thr Val Arg Tyr Ser Arg Leu Gly Asn Lys Gln Thr
```

```
            290                 295                 300
Leu Arg Thr Arg Ser Gly Ala Thr Ile Gly Ala Arg Val His Tyr Tyr
305                 310                 315                 320

Tyr Asp Ile Ser Ser Ile Asn Pro Ala Gly Glu Ser Ile Glu Met Gln
                325                 330                 335

Pro Leu Gly Ala Ser Ala Thr Thr Ser Thr Leu Asn Asp Gly Leu
                340                 345                 350

Tyr Asp Ile Tyr Ala Asp Thr Asp Phe Thr Val Asp Thr Pro Ala Thr
                355                 360                 365

His Asn Val Ser Pro Ser Thr Ala Val Gln Ser Thr Ser Ala Val Ser
                370                 375                 380

Ala Tyr Val Pro Thr Asn Thr Thr Val Pro Leu Ser Thr Gly Phe Asp
385                 390                 395                 400

Ile Pro Ile Phe Ser Gly Pro Asp Val Pro Ile Glu His Ala Pro Thr
                405                 410                 415

Gln Val Phe Pro Phe Pro Leu Ala Pro Thr Thr Pro Gln Val Ser Ile
                420                 425                 430

Phe Val Asp Gly Gly Asp Phe Tyr Leu His Pro Ser Tyr Tyr Met Leu
                435                 440                 445

Lys Arg Arg Lys Arg Val Ser Tyr Phe Phe Thr Asp Val Ser Val
                450                 455                 460

Ala Ala
465

<210> SEQ ID NO 11
<211> LENGTH: 470
<212> TYPE: PRT
<213> ORGANISM: Human papillomavirus type 39

<400> SEQUENCE: 11

Met Val Ser His Arg Ala Ala Arg Arg Lys Arg Ala Ser Ala Thr Asp
1               5                   10                  15

Leu Tyr Arg Thr Cys Lys Gln Ser Gly Thr Cys Pro Pro Asp Val Val
                20                  25                  30

Asp Lys Val Glu Gly Thr Thr Leu Ala Asp Lys Ile Leu Gln Trp Thr
            35                  40                  45

Ser Leu Gly Ile Phe Leu Gly Gly Leu Gly Ile Gly Thr Gly Thr Gly
50                  55                  60

Thr Gly Gly Arg Thr Gly Tyr Ile Pro Leu Gly Gly Arg Pro Asn Thr
65                  70                  75                  80

Val Val Asp Val Ser Pro Ala Arg Pro Pro Val Val Ile Glu Pro Val
                85                  90                  95

Gly Pro Ser Glu Pro Ser Ile Val Gln Leu Val Glu Asp Ser Ser Val
                100                 105                 110

Ile Thr Ser Gly Thr Pro Val Pro Thr Phe Thr Gly Thr Ser Gly Phe
            115                 120                 125

Glu Ile Thr Ser Ser Ser Thr Thr Pro Ala Val Leu Asp Ile Thr
            130                 135                 140

Pro Ser Ser Gly Ser Val Gln Ile Thr Ser Thr Ser Tyr Thr Asn Pro
145                 150                 155                 160

Ala Phe Thr Asp Pro Ser Leu Ile Glu Val Pro Gln Thr Gly Glu Thr
                165                 170                 175

Ser Gly Asn Ile Phe Val Ser Thr Pro Thr Ser Gly Thr His Gly Tyr
                180                 185                 190
```

```
Glu Glu Ile Pro Met Glu Val Phe Ala Thr His Gly Thr Gly Thr Glu
            195                 200                 205

Pro Ile Ser Ser Thr Pro Thr Pro Gly Ile Ser Arg Val Ala Gly Pro
        210                 215                 220

Arg Leu Tyr Ser Arg Ala His Gln Gln Val Arg Val Ser Asn Phe Asp
225                 230                 235                 240

Phe Val Thr His Pro Ser Ser Phe Val Thr Phe Asp Asn Pro Ala Phe
            245                 250                 255

Glu Pro Val Asp Thr Thr Leu Thr Tyr Glu Ala Ala Asp Ile Ala Pro
        260                 265                 270

Asp Pro Asp Phe Leu Asp Ile Val Arg Leu His Arg Pro Ala Leu Thr
            275                 280                 285

Ser Arg Lys Gly Thr Val Arg Phe Ser Arg Leu Gly Lys Lys Ala Thr
290                 295                 300

Met Val Thr Arg Arg Gly Thr Gln Ile Gly Ala Gln Val His Tyr Tyr
305                 310                 315                 320

His Asp Ile Ser Ser Ile Ala Pro Ala Glu Ser Ile Glu Leu Gln Pro
                325                 330                 335

Leu Val His Ala Glu Pro Ser Asp Ala Ser Asp Ala Leu Phe Asp Ile
            340                 345                 350

Tyr Ala Asp Val Asp Asn Asn Thr Tyr Leu Asp Thr Ala Phe Asn Asn
        355                 360                 365

Thr Arg Asp Ser Gly Thr Thr Tyr Asn Thr Gly Ser Leu Pro Ser Val
    370                 375                 380

Ala Ser Ser Ala Ser Thr Lys Tyr Ala Asn Thr Thr Ile Pro Phe Ser
385                 390                 395                 400

Thr Ser Trp Asn Met Pro Val Asn Thr Gly Pro Asp Ile Ala Leu Pro
                405                 410                 415

Ser Thr Thr Pro Gln Leu Pro Leu Val Pro Ser Gly Pro Ile Asp Thr
            420                 425                 430

Thr Tyr Ala Ile Thr Ile Gln Gly Ser Asn Tyr Tyr Leu Leu Pro Leu
        435                 440                 445

Leu Tyr Phe Phe Leu Lys Lys Arg Lys Arg Ile Pro Tyr Phe Phe Ser
450                 455                 460

Asp Gly Tyr Val Ala Val
465                 470

<210> SEQ ID NO 12
<211> LENGTH: 554
<212> TYPE: PRT
<213> ORGANISM: Human papillomavirus type 41

<400> SEQUENCE: 12

Met Leu Ala Arg Gln Arg Val Lys Arg Ala Asn Pro Glu Gln Leu Tyr
1               5                   10                  15

Lys Thr Cys Lys Ala Thr Gly Gly Asp Cys Pro Pro Asp Val Ile Lys
            20                  25                  30

Arg Tyr Glu Gln Thr Thr Pro Ala Asp Ser Ile Leu Lys Tyr Gly Ser
        35                  40                  45

Val Gly Val Phe Gly Gly Leu Gly Ile Gly Thr Gly Arg Gly Gly
    50                  55                  60

Gly Gly Thr Val Leu Gly Ala Gly Ala Val Gly Gly Arg Pro Ser Ile
65                  70                  75                  80

Ser Ser Gly Ala Ile Gly Pro Arg Asp Ile Leu Pro Ile Glu Ser Gly
                85                  90                  95
```

```
Gly Pro Ser Leu Ala Glu Glu Ile Pro Leu Pro Met Ala Pro Arg
            100                 105                 110

Val Pro Arg Pro Thr Asp Pro Phe Arg Pro Ser Val Leu Glu Glu Pro
            115                 120                 125

Phe Ile Ile Arg Pro Pro Glu Arg Pro Asn Ile Leu His Glu Gln Arg
            130                 135                 140

Phe Pro Thr Asp Ala Ala Pro Phe Asp Asn Gly Asn Thr Glu Ile Thr
145                 150                 155                 160

Thr Ile Pro Ser Gln Tyr Asp Val Ser Gly Gly Val Asp Ile Gln
            165                 170                 175

Ile Ile Glu Leu Pro Ser Val Asn Asp Pro Gly Pro Ser Val Val Thr
            180                 185                 190

Arg Thr Gln Tyr Asn Asn Pro Thr Phe Glu Val Glu Val Ser Thr Asp
            195                 200                 205

Ile Ser Gly Glu Thr Ser Ser Thr Asp Asn Ile Ile Val Gly Ala Glu
            210                 215                 220

Ser Gly Gly Thr Ser Val Gly Asp Asn Ala Glu Leu Ile Pro Leu Leu
225                 230                 235                 240

Asp Ile Ser Arg Gly Asp Thr Ile Asp Thr Thr Ile Leu Ala Pro Gly
            245                 250                 255

Glu Glu Glu Thr Ala Phe Val Thr Ser Thr Pro Glu Arg Val Pro Ile
            260                 265                 270

Gln Glu Arg Leu Pro Ile Arg Pro Tyr Gly Arg Gln Tyr Gln Gln Val
            275                 280                 285

Arg Val Thr Asp Pro Glu Phe Leu Asp Ser Ala Ala Val Leu Val Ser
            290                 295                 300

Leu Glu Asn Pro Val Phe Asp Ala Asp Ile Thr Leu Thr Phe Glu Asp
305                 310                 315                 320

Asp Leu Gln Gln Ala Leu Arg Ser Asp Thr Asp Leu Arg Asp Val Arg
            325                 330                 335

Arg Leu Ser Arg Pro Tyr Tyr Gln Arg Arg Thr Thr Gly Leu Arg Val
            340                 345                 350

Ser Arg Leu Gly Gln Arg Gly Thr Ile Ser Thr Arg Ser Gly Val
            355                 360                 365

Gln Val Gly Ser Ala Ala His Phe Phe Gln Asp Ile Ser Pro Ile Gly
            370                 375                 380

Gln Ala Ile Glu Pro Ile Asp Ala Ile Glu Leu Asp Val Leu Gly Glu
385                 390                 395                 400

Gln Ser Gly Glu Gly Thr Ile Val Arg Gly Asp Pro Thr Pro Ser Ile
            405                 410                 415

Glu Gln Asp Ile Gly Leu Thr Ala Leu Gly Asp Asn Ile Glu Asn Glu
            420                 425                 430

Leu Gln Glu Ile Asp Leu Leu Thr Ala Asp Gly Glu Glu Asp Gln Glu
            435                 440                 445

Gly Arg Asp Leu Gln Leu Val Phe Ser Thr Gly Asn Asp Glu Val Val
            450                 455                 460

Asp Ile Met Thr Ile Pro Ile Arg Ala Gly Gly Asp Asp Arg Pro Ser
465                 470                 475                 480

Val Phe Ile Phe Ser Asp Asp Gly Thr His Ile Val Tyr Pro Thr Ser
            485                 490                 495

Thr Thr Ala Thr Thr Pro Leu Val Pro Ala Gln Pro Ser Asp Val Pro
            500                 505                 510
```

```
Tyr Ile Val Val Asp Leu Tyr Ser Gly Ser Met Asp Tyr Asp Ile His
                515                 520                 525

Pro Ser Leu Leu Arg Arg Lys Arg Lys Arg Lys Arg Val Tyr Phe
530                 535                 540

Ser Asp Gly Arg Val Ala Ser Arg Pro Lys
545                 550

<210> SEQ ID NO 13
<211> LENGTH: 468
<212> TYPE: PRT
<213> ORGANISM: Human papillomavirus type 51

<400> SEQUENCE: 13

Met Val Ala Thr Arg Ala Arg Arg Lys Arg Ala Ser Val Thr Gln
1               5                   10                  15

Leu Tyr Ser Thr Cys Lys Ala Ala Gly Thr Cys Pro Pro Asp Val Val
                20                  25                  30

Asn Lys Val Glu Gly Thr Thr Leu Ala Asp Lys Ile Leu Gln Trp Ser
            35                  40                  45

Gly Leu Gly Ile Phe Leu Gly Gly Leu Gly Ile Gly Thr Gly Ser Gly
        50                  55                  60

Ser Gly Gly Arg Thr Gly Tyr Ile Pro Leu Gly Gly Gly Arg Pro
65                  70                  75                  80

Gly Val Val Asp Ile Ala Pro Ala Arg Pro Pro Ile Ile Ile Asp Leu
                85                  90                  95

Trp His His Thr Glu Pro Ser Ile Val Asn Leu Val Glu Asp Ser Ser
                100                 105                 110

Ile Ile Gln Ser Gly Ser Pro Ile Pro Thr Phe Thr Gly Thr Asp Gly
            115                 120                 125

Phe Glu Ile Thr Ser Ser Ser Thr Thr Thr Pro Ala Val Leu Asp Ile
        130                 135                 140

Thr Pro Ser Ala Gly Thr Val His Val Ser Ser Thr Asn Ile Glu Asn
145                 150                 155                 160

Pro Leu Tyr Ile Glu Pro Pro Ser Ile Glu Ala Pro Gln Ser Gly Glu
                165                 170                 175

Val Ser Asp Ile Tyr Leu Leu Val His Tyr Ser Gly Thr His Gly Tyr
                180                 185                 190

Glu Glu Ile Pro Met Glu Val Phe Ala Ser Asn Val Ser Thr Gly Thr
            195                 200                 205

Glu Pro Ile Ser Ser Thr Pro Thr Pro Gly Val Ser Arg Ile Ala Ala
        210                 215                 220

Pro Arg Leu Tyr Ser Lys Ser Tyr Thr Gln Val Lys Val Thr Asn Pro
225                 230                 235                 240

Asp Phe Ile Ser Lys Pro Ser Thr Phe Val Thr Phe Asn Asn Pro Ala
                245                 250                 255

Phe Glu Pro Ile Asp Thr Ser Ile Thr Phe Glu Glu Pro Asp Ala Val
                260                 265                 270

Ala Pro Asp Pro Asp Phe Leu Asp Ile Ile Thr Leu His Arg Pro Ala
            275                 280                 285

Leu Thr Ser Arg Arg Gly Thr Val Arg Phe Ser Arg Leu Gly Gln Lys
        290                 295                 300

Ala Thr Met Arg Thr Arg Ser Gly Lys Gln Ile Gly Ala Arg Val His
305                 310                 315                 320

Tyr Tyr His Asp Ile Ser Arg Ile Ala Pro Ala Asp Glu Leu Glu Met
                325                 330                 335
```

```
Gln Pro Leu Leu Ser Pro Ser Asn Asn Tyr Ser Tyr Asp Ile Tyr Ala
                340                 345                 350

Asp Leu Asp Glu Ala Glu Thr Gly Phe Ile Gln Pro Thr His Thr Thr
            355                 360                 365

Pro Met Ser His Ser Ser Leu Ser Arg Gln Leu Pro Ser Leu Ser Ser
        370                 375                 380

Ser Met Ser Ser Ser Tyr Ala Asn Val Thr Ile Pro Phe Ser Thr Thr
385                 390                 395                 400

Tyr Ser Val Pro Ile His Thr Gly Pro Asp Val Val Leu Pro Thr Ser
                405                 410                 415

Pro Thr Val Trp Pro Tyr Val Pro His Thr Ser Ile Asp Thr Lys His
            420                 425                 430

Ser Ile Val Ile Leu Gly Gly Asp Tyr Tyr Leu Trp Pro Tyr Thr His
        435                 440                 445

Leu Leu Arg Lys Arg Lys Arg Ile Pro Tyr Phe Phe Thr Asp Gly
    450                 455                 460

Ile Val Ala His
465

<210> SEQ ID NO 14
<211> LENGTH: 504
<212> TYPE: PRT
<213> ORGANISM: Human papillomavirus type 63

<400> SEQUENCE: 14

Met Leu Arg Val Arg Lys Arg Ala Ala Pro Gln Asp Ile Tyr Pro
1               5                   10                  15

Ala Cys Lys Val Ala Asn Asn Cys Pro Pro Asp Ile Gln Asn Lys Ile
                20                  25                  30

Glu Gln Thr Thr Val Ala Asp Lys Ile Leu Gln Tyr Gly Ser Leu Gly
            35                  40                  45

Ile Phe Leu Gly Gly Leu Gly Ile Gly Thr Gly Lys Gly Gly Gly Gly
    50                  55                  60

Arg Tyr Gly Tyr Thr Pro Leu Gly Asp Ser Gly Ala Val Arg Val Gly
65              70                  75                  80

Gly Arg Ser Thr Pro Val Arg Pro Thr Val Pro Val Glu Thr Val Gly
                85                  90                  95

Pro Arg Asp Ile Leu Pro Ile Asp Ser Leu Asp Pro Leu Gly Pro Ser
                100                 105                 110

Val Ile Glu Leu Glu Asp Ile Pro Ala Thr Thr Val Glu Val Val Ala
            115                 120                 125

Glu Val His Pro Ile Ser Asp Thr Pro Gln Ile Pro Ala Pro Thr Thr
        130                 135                 140

Asp Glu Ser Ser Ser Ala Val Leu His Ile Pro Gln Glu Ser Pro Ala
145                 150                 155                 160

Ala Arg Thr Ile Thr Arg Ser Gln Tyr Asn Asn Pro Leu Phe Arg Ile
                165                 170                 175

Thr Ala Ser Ala Asp Ile Ala Ser Gly Glu Ala Ser Ala Ser Asp Asn
            180                 185                 190

Ile Phe Ile Asp Val Asp Thr Pro Gly Gln Ile Val Gly Gln Glu Ile
        195                 200                 205

Pro Leu Val Asn Phe Asp Met Gly Pro Ile Ser Thr Glu Gly Glu Leu
    210                 215                 220

Glu Thr Glu Phe Thr Thr Ser Thr Pro Arg Thr Thr Gln Val Gln Glu
```

```
                    225                 230                 235                 240
Arg Pro Thr Arg Phe Tyr Asn Arg Arg Tyr Tyr Glu Gln Val Pro Val
                245                 250                 255

Thr Ala Pro Glu Phe Ile Thr Arg Pro Ala Ser Leu Val Thr Phe Glu
                260                 265                 270

Asn Pro Ala Phe Glu Arg Ser Val Ser Leu Ile Phe Glu Gln Asp Leu
                275                 280                 285

Glu Asp Ile Leu Asn Ala Pro Asp Gln Asp Phe Arg Asp Ile Val Tyr
        290                 295                 300

Leu Ser Arg Pro Thr Tyr Ser Arg Ala Pro Asp Gly Arg Met Arg Leu
305                 310                 315                 320

Ser Arg Leu Gly Arg Arg Ala Thr Ile Ser Thr Arg Ser Gly Val Thr
                325                 330                 335

Ile Gly Ala Gln Ser His Phe Tyr Met Asp Ile Ser Ser Ile Ser Ser
                340                 345                 350

Asn Asp Gly Ile Glu Leu Gln Thr Leu Gly Glu Ala Ser Gly Glu Thr
            355                 360                 365

Val Val Gln Ser Ser Leu Ala Ala Ser Asp Pro Ile Glu Ala Glu His
    370                 375                 380

Ser Phe Ile Glu Pro Ala Pro Ser Ile Asp Ser Tyr Asp Ile Val Ser
385                 390                 395                 400

Leu Gln Ser Glu Thr Tyr Ser Asp Glu His Leu Leu Asp Met Tyr Glu
                405                 410                 415

Pro Val Gly Ser Ser Leu Gln Leu Gln Ile Ser Asp Val Arg Gly Arg
                420                 425                 430

Pro Thr Val Ile Asp Ile Pro Phe Arg Pro Arg Arg Pro Pro Leu Gly
            435                 440                 445

Pro Ile Asn Ala Gly Val Asp Ile Tyr Ser Pro Thr Ala Ser Val Gly
        450                 455                 460

Ser Pro Thr Ile Asn Pro Thr Asp Leu Asp Ile Pro Leu Ile Ile Ile
465                 470                 475                 480

His Leu Asp Asn Ser Thr Gly Asp Tyr Asp Leu His Pro Ser Leu Arg
                485                 490                 495

Lys Arg Arg Lys Leu Val His Ile
                500

<210> SEQ ID NO 15
<211> LENGTH: 467
<212> TYPE: PRT
<213> ORGANISM: Human papillomavirus type 69

<400> SEQUENCE: 15

Met Val Ala Val Arg Ala Ser Arg Arg Lys Arg Ala Ser Ala Thr Asp
1               5                   10                  15

Leu Tyr Lys Thr Cys Lys Ala Ala Gly Thr Cys Pro Pro Asp Val Ile
                20                  25                  30

Pro Lys Ile Glu Gly Ser Thr Leu Ala Asp Lys Ile Leu Gln Trp Ser
            35                  40                  45

Gly Leu Gly Ile Phe Leu Gly Gly Leu Gly Ile Gly Thr Gly Thr Gly
        50                  55                  60

Thr Gly Gly Arg Thr Gly Tyr Ile Pro Leu Gly Gly Gly Arg Pro
65                  70                  75                  80

Ser Val Val Asp Ile Gly Pro Thr Arg Pro Pro Ile Ile Ile Glu Pro
                85                  90                  95
```

Val Gly Pro Thr Glu Pro Ser Ile Val Thr Leu Val Glu Glu Ser Ser
            100                 105                 110

Ile Ile Gln Ser Gly Ser Pro Phe Pro Asn Phe Ser Gly Gly Asp Gly
        115                 120                 125

Phe Glu Val Thr Thr Ser Ser Thr Thr Thr Pro Ala Val Leu Asp Ile
    130                 135                 140

Thr Pro Ser Pro Gly Thr Val His Val Thr Ser Thr Asn Ile Gln Asn
145                 150                 155                 160

Pro Leu Tyr Ile Glu Pro Val Asp Ile Pro Gln Ser Gly Glu Ala
                165                 170                 175

Leu Gly His Ile Phe Thr Ser Thr Ser Thr Ala Gly Thr His Ser Tyr
            180                 185                 190

Glu Glu Ile Pro Met Glu Val Phe Ala Ser Asn Thr Ser Ser Gly Ser
        195                 200                 205

Lys Pro Ile Ser Ser Thr Pro Ile Pro Gly Ile Arg Arg Val Ala Ala
    210                 215                 220

Pro Arg Leu Tyr Ser Lys Ala Tyr Gln Gln Val Lys Val Thr Asp Pro
225                 230                 235                 240

Asn Phe Ile Ser Lys Pro Ser Thr Phe Ile Thr Phe Asp Asn Pro Ala
                245                 250                 255

Tyr Glu Pro Met Asp Thr Thr Leu Thr Phe Ser Ala Asp Ser His Val
            260                 265                 270

Ala Pro Asp Pro Asp Phe Leu Asp Ile Ile Ala Leu His Arg Pro Ala
        275                 280                 285

Leu Thr Ser Arg Arg Gly Thr Val Arg Phe Ser Arg Leu Gly Gln Lys
290                 295                 300

Ala Thr Leu Lys Thr Arg Ser Gly Lys Gln Ile Gly Ala Lys Val His
305                 310                 315                 320

Tyr Tyr His Asp Ile Ser Pro Ile His Ala Thr Glu Glu Ala Ile Glu
                325                 330                 335

Leu Gln Pro Leu Ile Thr Ser Glu Gln His Ser Thr Pro Leu Phe Asp
            340                 345                 350

Val Tyr Ala Asp Ala Asp Pro Ala Pro Thr Phe Thr Phe Pro Ser Thr
        355                 360                 365

Thr Pro Thr Thr Ile Pro Arg Phe Ser Ser Thr Ile Phe Ser Thr Thr
370                 375                 380

Ser Ser Ala Pro Leu Asn Val Thr Ile Pro Leu Ser Thr Ser Phe Asp
385                 390                 395                 400

Ile Pro Ile Tyr Asn Gly Pro Asp Ile Tyr Ala Pro Val Pro Ser Ser
                405                 410                 415

Thr Trp Pro Tyr Ile Pro Pro Pro Thr Thr Met Ser His Ser Val
            420                 425                 430

Val Ala Gln Gly Gly Asn Tyr Tyr Leu Trp Pro Tyr Ile Tyr Leu Ile
        435                 440                 445

His Lys Arg Arg Arg Lys Arg Val Pro Cys Phe Phe Ser Asp Gly Leu
450                 455                 460

Ala Ala Tyr
465

<210> SEQ ID NO 16
<211> LENGTH: 521
<212> TYPE: PRT
<213> ORGANISM: Human papillomavirus type 88

<400> SEQUENCE: 16

```
Met Tyr Lys Thr Arg Ser Lys Arg Asp Thr Ala Glu Asn Leu Tyr Arg
1               5                   10                  15

His Cys Lys Ala Thr Gly Asn Cys Pro Pro Asp Val Glu Asn Lys Ile
                20                  25                  30

Glu Gly Asn Thr Leu Ala Asp Arg Leu Leu Arg Ile Phe Gly Ser Val
            35                  40                  45

Ile Tyr Leu Gly Gly Leu Gly Leu Gly Thr Gly Glu Gly Thr Thr Gly
    50                  55                  60

Ile Arg Pro Ile Glu Ala Pro Val Glu Thr Val Arg Pro Asp Ile Thr
65                  70                  75                  80

Val Glu Arg Pro Thr Val Arg Pro Arg Pro Gln Arg Pro Thr Thr Phe
                85                  90                  95

Gly Thr Pro Ile Asp Arg Ile Gly Ser Ala Asp Ile Thr Pro Asn Val
            100                 105                 110

Val Lys Pro Thr Glu Ser Ser Ile Val Pro Leu Asn Glu Ser Gly Ile
            115                 120                 125

Pro Asp Pro Thr Ile Ile Asp Ser Ala Thr Gly Gly Gly Glu Gly Leu
    130                 135                 140

Gly Glu Tyr Asp Ile Leu Thr Thr Val Asp Pro Asn Glu Thr Leu Gly
145                 150                 155                 160

Ala Thr Gly Gly His Pro Thr Thr Ser Gly Thr Leu Asn Asn Glu Thr
                165                 170                 175

Ala Ile Leu Asp Ile Ser Pro Tyr Glu Pro Pro Lys Arg Phe Ala
            180                 185                 190

Leu Ala Pro Ser Val His Ala Glu Ala Asp Ile Thr Ile Ile Glu Ser
        195                 200                 205

Ser Leu Pro Thr Glu Ser Asn Ile Asn Val Phe Val Asp Ala Asn Ile
    210                 215                 220

Thr Gly Glu Ile Val Gly Glu Glu Ile Pro Leu Glu Pro Ile Asn Ser
225                 230                 235                 240

Ile Glu Glu Phe Glu Ile Glu Ala Gly Arg Gln Thr Ser Thr Pro Arg
                245                 250                 255

Glu Ala Val Glu Arg Phe Leu Gly Arg Ala Arg Ser Leu Tyr Asn Arg
            260                 265                 270

Tyr Ile Gln Gln Ile Arg Thr Asp Asn Val Asp Phe Leu Thr Arg Pro
    275                 280                 285

Ser Arg Ala Val Gln Phe Glu Phe Glu Asn Pro Ala Phe Thr Gly Asp
    290                 295                 300

Val Ser Leu Glu Phe Ala Arg Asp Val Ala Glu Ile Thr Ala Ala Pro
305                 310                 315                 320

Asp Pro Asp Phe Ala Asp Ile Ile Arg Leu Gly Arg Pro Ile Phe Ser
                325                 330                 335

Glu Thr Pro Gly Gly Thr Val Arg Val Ser Arg Leu Gly Thr Lys Gly
            340                 345                 350

Ala Ile Ser Thr Arg Ser Gly Thr Ile Ile Gly Pro Arg Val His Tyr
    355                 360                 365

Tyr Phe Asp Leu Ser Ala Ile Glu Pro Ile Glu Pro Asp Val Ile Glu
    370                 375                 380

Leu Ser Asn Leu Gly Glu Phe Ser Gly Glu Ser Thr Ile Val Asp Ser
385                 390                 395                 400

Ile Leu Ser Gly His Thr Val Asp Pro Ile Ala Pro Phe Glu Ser Thr
                405                 410                 415
```

```
Phe Ser Ile Ala Asp Leu Glu Asp Pro Leu Leu Glu Asp Phe Ser Asn
            420                 425                 430

Ser His Leu Phe Val His Phe Glu Glu Glu Asp Glu Leu Ile Ser Val
            435                 440                 445

Pro Thr Leu Pro Pro Gly Ala Ala Ile Lys Ala Phe Val Asp Asp Tyr
450                 455                 460

Ala Asp Ile Ile Val Ser Tyr Pro Glu Met Val Asn Val Asn Lys Ile
465                 470                 475                 480

Glu Ile Pro Ala Thr Thr Leu Val Pro Ser Pro Asp Ile Arg Leu
                485                 490                 495

Asp Trp Phe Ser Pro Asp Tyr Asp Leu His Pro Ser Leu Leu Arg Arg
            500                 505                 510

Arg Arg Lys Arg Lys Arg Asn Met Phe
            515                 520

<210> SEQ ID NO 17
<211> LENGTH: 524
<212> TYPE: PRT
<213> ORGANISM: Human papillomavirus type 95

<400> SEQUENCE: 17

Met Asn Ser Ala Arg Val Lys Arg Asp Ser Val Pro Asn Leu Tyr
1               5                   10                  15

Ala Lys Cys Gln Leu Ser Gly Asp Cys Leu Pro Asp Val Lys Asn Lys
            20                  25                  30

Val Glu Ala Asn Thr Ile Ala Asp Arg Leu Leu Arg Trp Leu Gly Ser
            35                  40                  45

Ile Ile Tyr Leu Gly Gly Leu Gly Ile Gly Thr Gly Arg Gly Ser Gly
50                  55                  60

Gly Ser Ser Gly Tyr Asn Pro Leu Ala Thr Pro Ser Arg Val Thr Pro
65                  70                  75                  80

Ser Gly Thr Leu Val Arg Pro Thr Val Pro Val Glu Gly Leu Gly Pro
            85                  90                  95

Val Glu Ile Val Pro Val Asp Ala Val Asp Pro Ala Gly Ser Ser Ile
            100                 105                 110

Val Pro Leu Thr Asp Val Ser Val Pro Glu Val Val Asp Gly Glu
            115                 120                 125

Gly Gly Ala Ile Asp Leu Gly Pro Pro Glu Asp Thr Gly Val Thr Ser
            130                 135                 140

Arg Pro Pro Glu Ile Leu Thr Thr Pro Asp Pro Val Ser Asp Val Ser
145                 150                 155                 160

Gly Thr Asn Ser His Pro Thr Ile Ile Ser Gly Glu Asp Asn Thr Ile
                165                 170                 175

Ala Val Leu Asp Ile Ser Pro Ile Glu Pro Pro Thr Lys Arg Ile Ala
            180                 185                 190

Leu Gly Thr Arg Gly Gln Ser Ser Thr Pro His Ile Ser Val Ile Ser
            195                 200                 205

Gly Ser Thr Asp Ile Gly Gln Ser Ser Asp Ile Asn Val Phe Val Asp
            210                 215                 220

Ala Gln Phe Ser Gly Asp Ser Ile Gly Tyr Thr Glu Glu Ile Pro Leu
225                 230                 235                 240

Gln Asp Leu Asn Thr Ile Gln Glu Phe Glu Ile Glu Thr Pro Pro Lys
            245                 250                 255

Thr Ser Thr Pro Arg Asp Thr Ile Ala Arg Ala Ile Gly Arg Ala Arg
            260                 265                 270
```

-continued

```
Glu Leu Tyr Asn Arg Arg Val Gln Gln Ile Gln Thr Arg Asn Pro Ala
        275                 280                 285
Leu Leu Ala Gln Pro Ser Arg Ala Ile Val Phe Gly Phe Glu Asn Pro
    290                 295                 300
Ala Phe Asp Ala Asp Ile Thr Gln Val Phe Gln Gln Asp Leu Ala Gln
305                 310                 315                 320
Val Ala Ala Ala Pro Asp Pro Asp Phe Ala Asp Ile Val Thr Ile Gly
                325                 330                 335
Arg Pro Gln Phe Ser Glu Thr Glu Ser Gly Gln Ile Arg Val Ser Arg
            340                 345                 350
Leu Gly Arg Arg Gly Thr Ile Gln Thr Arg Ser Gly Ile Gln Ile Gly
        355                 360                 365
Gln Ala Val His Phe Tyr Tyr Asp Leu Ser Thr Ile Asp Thr Ala Asp
    370                 375                 380
Ala Ile Glu Leu Ser Thr Leu Gly Gln His Ser Gly Asp Gln Ser Ile
385                 390                 395                 400
Val Asp Ala Met Ala Glu Ser Ser Leu Ile Asp Pro Phe Ala Thr Pro
                405                 410                 415
Asp Thr Thr Val Ala Glu Glu Gln Leu Leu Asp Pro Gln Thr Glu
            420                 425                 430
Asp Phe Ser Asn Ser His Leu Val Leu Thr Thr Ser Asn Arg Gly Ser
        435                 440                 445
Thr Leu Thr Ile Pro Thr Ile Pro Pro Gly Ile Gly Leu Arg Ile Tyr
    450                 455                 460
Val Asp Asp Ile Gly Ser Asp Leu Phe Val Ser Tyr Pro Glu Ser Ser
465                 470                 475                 480
Leu Ile Pro Pro Gly Gly Leu Pro Thr Glu Pro Phe Phe Pro Leu Lys
                485                 490                 495
Pro Ala Leu Leu Thr Asp Phe Tyr Ser Asp Phe Thr Tyr Tyr Pro Ser
            500                 505                 510
Leu Tyr Arg Lys Lys Arg Lys Arg Ser Asp Leu Phe
        515                 520

<210> SEQ ID NO 18
<211> LENGTH: 19
<212> TYPE: PRT
<213> ORGANISM: Human papillomavirus type 1a

<400> SEQUENCE: 18

Pro Ser Cys Lys Ile Ser Asn Thr Cys Pro Pro Asp Ile Gln Asn Lys
1               5                   10                  15

Ile Glu His

<210> SEQ ID NO 19
<211> LENGTH: 19
<212> TYPE: PRT
<213> ORGANISM: Human papillomavirus type 2a

<400> SEQUENCE: 19

Arg Thr Cys Lys Gln Ala Gly Thr Cys Pro Pro Asp Ile Ile Pro Arg
1               5                   10                  15

Val Glu Gln

<210> SEQ ID NO 20
<211> LENGTH: 19
<212> TYPE: PRT
```

<210> SEQ ID NO 20
<211> LENGTH: 19
<212> TYPE: PRT
<213> ORGANISM: Human papillomavirus type 3

<400> SEQUENCE: 20

Arg Thr Cys Lys Ala Ala Gly Thr Cys Pro Pro Asp Val Ile Pro Lys
1               5                   10                  15

Val Glu Gly

<210> SEQ ID NO 21
<211> LENGTH: 19
<212> TYPE: PRT
<213> ORGANISM: Human papillomavirus type 4

<400> SEQUENCE: 21

Ala Lys Cys Gln Leu Ser Gly Asn Cys Leu Pro Asp Val Lys Asn Lys
1               5                   10                  15

Val Glu Ala

<210> SEQ ID NO 22
<211> LENGTH: 19
<212> TYPE: PRT
<213> ORGANISM: Human papillomavirus type 5

<400> SEQUENCE: 22

Gln Thr Cys Lys Gln Ala Gly Thr Cys Pro Pro Asp Val Ile Asn Lys
1               5                   10                  15

Val Glu Gln

<210> SEQ ID NO 23
<211> LENGTH: 19
<212> TYPE: PRT
<213> ORGANISM: Human papillomavirus type 6

<400> SEQUENCE: 23

Gln Thr Cys Lys Leu Thr Gly Thr Cys Pro Pro Asp Val Ile Pro Lys
1               5                   10                  15

Val Glu His

<210> SEQ ID NO 24
<211> LENGTH: 19
<212> TYPE: PRT
<213> ORGANISM: Human papillomavirus type 9

<400> SEQUENCE: 24

Arg Gly Cys Lys Ala Ala Gly Thr Cys Pro Pro Asp Val Ile Asn Lys
1               5                   10                  15

Val Glu His

<210> SEQ ID NO 25
<211> LENGTH: 19
<212> TYPE: PRT
<213> ORGANISM: Human papillomavirus type 10

<400> SEQUENCE: 25

Arg Thr Cys Lys Ala Ser Gly Thr Cys Pro Pro Asp Val Ile Pro Lys
1               5                   10                  15

Val Glu Gly

<210> SEQ ID NO 26
<211> LENGTH: 19
<212> TYPE: PRT
<213> ORGANISM: Human papillomavirus type 18

<400> SEQUENCE: 26

Lys Thr Cys Lys Gln Ser Gly Thr Cys Pro Pro Asp Val Val Pro Lys
1               5                   10                  15

Val Glu Gly

<210> SEQ ID NO 27
<211> LENGTH: 19
<212> TYPE: PRT
<213> ORGANISM: Human papillomavirus type 31

<400> SEQUENCE: 27

Gln Thr Cys Lys Ala Ala Gly Thr Cys Pro Ser Asp Val Ile Pro Lys
1               5                   10                  15

Ile Glu His

<210> SEQ ID NO 28
<211> LENGTH: 19
<212> TYPE: PRT
<213> ORGANISM: Human papillomavirus type 39

<400> SEQUENCE: 28

Arg Thr Cys Lys Gln Ser Gly Thr Cys Pro Pro Asp Val Val Asp Lys
1               5                   10                  15

Val Glu Gly

<210> SEQ ID NO 29
<211> LENGTH: 20
<212> TYPE: PRT
<213> ORGANISM: Human papillomavirus type 41

<400> SEQUENCE: 29

Lys Thr Cys Lys Ala Thr Gly Gly Asp Cys Pro Pro Asp Val Ile Lys
1               5                   10                  15

Arg Tyr Glu Gln
            20

<210> SEQ ID NO 30
<211> LENGTH: 19
<212> TYPE: PRT
<213> ORGANISM: Human papillomavirus type 51

<400> SEQUENCE: 30

Ser Thr Cys Lys Ala Ala Gly Thr Cys Pro Pro Asp Val Val Asn Lys
1               5                   10                  15

Val Glu Gly

<210> SEQ ID NO 31
<211> LENGTH: 19
<212> TYPE: PRT
<213> ORGANISM: Human papillomavirus type 63

<400> SEQUENCE: 31

Pro Ala Cys Lys Val Ala Asn Asn Cys Pro Pro Asp Ile Gln Asn Lys
1               5                   10                  15

Ile Glu Gln

<210> SEQ ID NO 32
<211> LENGTH: 19
<212> TYPE: PRT
<213> ORGANISM: Human papillomavirus type 69

```
<400> SEQUENCE: 32

Lys Thr Cys Lys Ala Ala Gly Thr Cys Pro Pro Asp Val Ile Pro Lys
1               5                   10                  15

Ile Glu Gly

<210> SEQ ID NO 33
<211> LENGTH: 19
<212> TYPE: PRT
<213> ORGANISM: Human papillomavirus type 88

<400> SEQUENCE: 33

Arg His Cys Lys Ala Thr Gly Asn Cys Pro Pro Asp Val Glu Asn Lys
1               5                   10                  15

Ile Glu Gly

<210> SEQ ID NO 34
<211> LENGTH: 19
<212> TYPE: PRT
<213> ORGANISM: Human papillomavirus type 95

<400> SEQUENCE: 34

Ala Lys Cys Gln Leu Ser Gly Asp Cys Leu Pro Asp Val Lys Asn Lys
1               5                   10                  15

Val Glu Ala

<210> SEQ ID NO 35
<211> LENGTH: 129
<212> TYPE: PRT
<213> ORGANISM: Artificial
<220> FEATURE:
<223> OTHER INFORMATION: L2 N-terminal peptides from cutaneous HPV
      genotypes 1a, 2a, 3, 4, 10, and 63

<400> SEQUENCE: 35

Pro Ser Cys Lys Ile Ser Asn Thr Cys Pro Pro Asp Ile Gln Asn Lys
1               5                   10                  15

Ile Glu His Gly Gly Pro Arg Thr Cys Lys Gln Ala Gly Thr Cys Pro
            20                  25                  30

Pro Asp Ile Ile Pro Arg Val Glu Gln Gly Gly Pro Arg Thr Cys Lys
        35                  40                  45

Ala Ala Gly Thr Cys Pro Pro Asp Val Ile Pro Lys Val Glu Gly Gly
    50                  55                  60

Gly Pro Ala Lys Cys Gln Leu Ser Gly Asn Cys Leu Pro Asp Val Lys
65                  70                  75                  80

Asn Lys Val Glu Ala Gly Gly Pro Arg Thr Cys Lys Ala Ser Gly Thr
                85                  90                  95

Cys Pro Pro Asp Val Ile Pro Lys Val Glu Gly Gly Pro Pro Ala
            100                 105                 110

Cys Lys Val Ala Asn Asn Cys Pro Pro Asp Ile Gln Asn Lys Ile Glu
        115                 120                 125

Gln

<210> SEQ ID NO 36
<211> LENGTH: 196
<212> TYPE: PRT
<213> ORGANISM: Artificial
<220> FEATURE:
<223> OTHER INFORMATION: L2 N-terminal peptides from cutaneous HPV
      genotypes 1a, 2a, 3, 4, 10, 41, 63, 88, and 95
```

<400> SEQUENCE: 36

```
Pro Ser Cys Lys Ile Ser Asn Thr Cys Pro Pro Asp Ile Gln Asn Lys
1               5                   10                  15

Ile Glu His Gly Gly Pro Arg Thr Cys Lys Gln Ala Gly Thr Cys Pro
            20                  25                  30

Pro Asp Ile Ile Pro Arg Val Glu Gln Gly Gly Pro Arg Thr Cys Lys
        35                  40                  45

Ala Ala Gly Thr Cys Pro Pro Asp Val Ile Pro Lys Val Glu Gly Gly
    50                  55                  60

Gly Pro Ala Lys Cys Gln Leu Ser Gly Asn Cys Leu Pro Asp Val Lys
65                  70                  75                  80

Asn Lys Val Glu Ala Gly Gly Pro Arg Thr Cys Lys Ala Ser Gly Thr
                85                  90                  95

Cys Pro Pro Asp Val Ile Pro Lys Val Glu Gly Gly Pro Lys Thr
                100                 105                 110

Cys Lys Ala Thr Gly Gly Asp Cys Pro Pro Asp Val Ile Lys Arg Tyr
            115                 120                 125

Glu Gln Gly Gly Pro Ala Cys Lys Val Ala Asn Asn Cys Pro Pro
130                 135                 140

Asp Ile Gln Asn Lys Ile Glu Gln Gly Gly Pro Arg His Cys Lys Ala
145                 150                 155                 160

Thr Gly Asn Cys Pro Pro Asp Val Glu Asn Lys Ile Glu Gly Gly Gly
                165                 170                 175

Pro Ala Lys Cys Gln Leu Ser Gly Asp Cys Leu Pro Asp Val Lys Asn
                180                 185                 190

Lys Val Glu Ala
            195
```

<210> SEQ ID NO 37
<211> LENGTH: 174
<212> TYPE: PRT
<213> ORGANISM: Artificial
<220> FEATURE:
<223> OTHER INFORMATION: L2 N-terminal peptides from cutaneous HPV genotypes 1a, 2a, 3, 4, 5, 6, 41, 88

<400> SEQUENCE: 37

```
Pro Ser Cys Lys Ile Ser Asn Thr Cys Pro Pro Asp Ile Gln Asn Lys
1               5                   10                  15

Ile Glu His Gly Gly Pro Arg Thr Cys Lys Gln Ala Gly Thr Cys Pro
            20                  25                  30

Pro Asp Ile Ile Pro Arg Val Glu Gln Gly Gly Pro Arg Thr Cys Lys
        35                  40                  45

Ala Ala Gly Thr Cys Pro Pro Asp Val Ile Pro Lys Val Glu Gly Gly
    50                  55                  60

Gly Pro Ala Lys Cys Gln Leu Ser Gly Asn Cys Leu Pro Asp Val Lys
65                  70                  75                  80

Asn Lys Val Glu Ala Gly Gly Pro Gln Thr Cys Lys Gln Ala Gly Thr
                85                  90                  95

Cys Pro Pro Asp Val Ile Asn Lys Val Glu Gln Gly Gly Pro Gln Thr
                100                 105                 110

Cys Lys Leu Thr Gly Thr Cys Pro Pro Asp Val Ile Pro Lys Val Glu
            115                 120                 125

His Gly Gly Pro Lys Thr Cys Lys Ala Thr Gly Gly Asp Cys Pro Pro
            130                 135                 140
```

Asp Val Ile Lys Arg Tyr Glu Gln Gly Gly Pro Arg His Cys Lys Ala
145                 150                 155                 160

Thr Gly Asn Cys Pro Pro Asp Val Glu Asn Lys Ile Glu Gly
            165                 170

<210> SEQ ID NO 38
<211> LENGTH: 218
<212> TYPE: PRT
<213> ORGANISM: Artificial
<220> FEATURE:
<223> OTHER INFORMATION: L2 N-terminal peptides from cutaneous HPV
      genotypes 1a,  2a,  3, 4, 5, 6, 9, 10, 41, 88

<400> SEQUENCE: 38

Pro Ser Cys Lys Ile Ser Asn Thr Cys Pro Asp Ile Gln Asn Lys
1               5                   10                  15

Ile Glu His Gly Gly Pro Arg Thr Cys Lys Gln Ala Gly Thr Cys Pro
            20                  25                  30

Pro Asp Ile Ile Pro Arg Val Glu Gln Gly Gly Pro Arg Thr Cys Lys
        35                  40                  45

Ala Ala Gly Thr Cys Pro Pro Asp Val Ile Pro Lys Val Glu Gly Gly
 50                  55                  60

Gly Pro Ala Lys Cys Gln Leu Ser Gly Asn Cys Leu Pro Asp Val Lys
65                  70                  75                  80

Asn Lys Val Glu Ala Gly Gly Pro Gln Thr Cys Lys Gln Ala Gly Thr
                85                  90                  95

Cys Pro Pro Asp Val Ile Asn Lys Val Glu Gln Gly Gly Pro Gln Thr
            100                 105                 110

Cys Lys Leu Thr Gly Thr Cys Pro Pro Asp Val Ile Pro Lys Val Glu
            115                 120                 125

His Gly Gly Pro Arg Gly Cys Lys Ala Ala Gly Thr Cys Pro Pro Asp
        130                 135                 140

Val Ile Asn Lys Val Glu His Gly Gly Pro Arg Thr Cys Lys Ala Ser
145                 150                 155                 160

Gly Thr Cys Pro Pro Asp Val Ile Pro Lys Val Glu Gly Gly Gly Pro
            165                 170                 175

Lys Thr Cys Lys Ala Thr Gly Gly Asp Cys Pro Pro Asp Val Ile Lys
        180                 185                 190

Arg Tyr Glu Gln Gly Gly Pro Arg His Cys Lys Ala Thr Gly Asn Cys
    195                 200                 205

Pro Pro Asp Val Glu Asn Lys Ile Glu Gly
    210                 215

<210> SEQ ID NO 39
<211> LENGTH: 262
<212> TYPE: PRT
<213> ORGANISM: Artificial
<220> FEATURE:
<223> OTHER INFORMATION: L2 N-terminal peptides from cutaneous HPV
      genotypes 1a,  2a,  3, 4, 5, 6, 9, 10, 41, 69,  88, and 95

<400> SEQUENCE: 39

Pro Ser Cys Lys Ile Ser Asn Thr Cys Pro Pro Asp Ile Gln Asn Lys
1               5                   10                  15

Ile Glu His Gly Gly Pro Arg Thr Cys Lys Gln Ala Gly Thr Cys Pro
            20                  25                  30

Pro Asp Ile Ile Pro Arg Val Glu Gln Gly Gly Pro Arg Thr Cys Lys
        35                  40                  45

Ala Ala Gly Thr Cys Pro Pro Asp Val Ile Pro Lys Val Glu Gly Gly
            50                  55                  60

Gly Pro Ala Lys Cys Gln Leu Ser Gly Asn Cys Leu Pro Asp Val Lys
65                  70                  75                  80

Asn Lys Val Glu Ala Gly Gly Pro Gln Thr Cys Lys Gln Ala Gly Thr
                85                  90                  95

Cys Pro Pro Asp Val Ile Asn Lys Val Glu Gln Gly Gly Pro Gln Thr
                100                 105                 110

Cys Lys Leu Thr Gly Thr Cys Pro Pro Asp Val Ile Pro Lys Val Glu
            115                 120                 125

His Gly Gly Pro Arg Gly Cys Lys Ala Ala Gly Thr Cys Pro Pro Asp
        130                 135                 140

Val Ile Asn Lys Val Glu His Gly Gly Pro Arg Thr Cys Lys Ala Ser
145                 150                 155                 160

Gly Thr Cys Pro Pro Asp Val Ile Pro Lys Val Glu Gly Gly Gly Pro
                165                 170                 175

Lys Thr Cys Lys Ala Thr Gly Gly Asp Cys Pro Pro Asp Val Ile Lys
            180                 185                 190

Arg Tyr Glu Gln Gly Gly Pro Arg His Cys Lys Ala Thr Gly Asn Cys
            195                 200                 205

Pro Pro Asp Val Glu Asn Lys Ile Glu Gly Gly Pro Lys Thr Cys
    210                 215                 220

Lys Ala Ala Gly Thr Cys Pro Pro Asp Val Ile Pro Lys Ile Glu Gly
225                 230                 235                 240

Gly Gly Pro Ala Lys Cys Gln Leu Ser Gly Asp Cys Leu Pro Asp Val
                245                 250                 255

Lys Asn Lys Val Glu Ala
            260

<210> SEQ ID NO 40
<211> LENGTH: 306
<212> TYPE: PRT
<213> ORGANISM: Artificial
<220> FEATURE:
<223> OTHER INFORMATION: L2 N-terminal peptides from HPV genotypes 1a,
    2a, 3, 4, 5, 6, 9, 10, 31, 41, 51, 69, 88, and 95

<400> SEQUENCE: 40

Pro Ser Cys Lys Ile Ser Asn Thr Cys Pro Pro Asp Ile Gln Asn Lys
1               5                   10                  15

Ile Glu His Gly Gly Pro Arg Thr Cys Lys Gln Ala Gly Thr Cys Pro
                20                  25                  30

Pro Asp Ile Ile Pro Arg Val Glu Gln Gly Gly Pro Arg Thr Cys Lys
            35                  40                  45

Ala Ala Gly Thr Cys Pro Pro Asp Val Ile Pro Lys Val Glu Gly Gly
            50                  55                  60

Gly Pro Ala Lys Cys Gln Leu Ser Gly Asn Cys Leu Pro Asp Val Lys
65                  70                  75                  80

Asn Lys Val Glu Ala Gly Gly Pro Gln Thr Cys Lys Gln Ala Gly Thr
                85                  90                  95

Cys Pro Pro Asp Val Ile Asn Lys Val Glu Gln Gly Gly Pro Gln Thr
                100                 105                 110

Cys Lys Leu Thr Gly Thr Cys Pro Pro Asp Val Ile Pro Lys Val Glu
            115                 120                 125

His Gly Gly Pro Arg Gly Cys Lys Ala Ala Gly Thr Cys Pro Pro Asp

```
                130                 135                 140
Val Ile Asn Lys Val Glu His Gly Gly Pro Arg Thr Cys Lys Ala Ser
145                 150                 155                 160

Gly Thr Cys Pro Pro Asp Val Ile Pro Lys Val Glu Gly Gly Gly Pro
                165                 170                 175

Lys Thr Cys Lys Ala Thr Gly Gly Asp Cys Pro Pro Asp Val Ile Lys
                180                 185                 190

Arg Tyr Glu Gln Gly Gly Pro Arg His Cys Lys Ala Thr Gly Asn Cys
                195                 200                 205

Pro Pro Asp Val Glu Asn Lys Ile Glu Gly Gly Pro Lys Thr Cys
                210                 215                 220

Lys Ala Ala Gly Thr Cys Pro Pro Asp Val Ile Pro Lys Ile Glu Gly
225                 230                 235                 240

Gly Gly Pro Ala Lys Cys Gln Leu Ser Gly Asp Cys Leu Pro Asp Val
                245                 250                 255

Lys Asn Lys Val Glu Ala Gly Gly Pro Gln Thr Cys Lys Ala Ala Gly
                260                 265                 270

Thr Cys Pro Ser Asp Val Ile Pro Lys Ile Glu His Gly Gly Pro Ser
                275                 280                 285

Thr Cys Lys Ala Ala Gly Thr Cys Pro Pro Asp Val Val Asn Lys Val
                290                 295                 300

Glu Gly
305

<210> SEQ ID NO 41
<211> LENGTH: 350
<212> TYPE: PRT
<213> ORGANISM: Artificial
<220> FEATURE:
<223> OTHER INFORMATION: L2 N-terminal peptides from  HPV genotypes 1a,
      2a,  3, 4,5, 6, 9, 10, 18, 31, 39, 41, 51, 69, 88, and 95

<400> SEQUENCE: 41

Pro Ser Cys Lys Ile Ser Asn Thr Cys Pro Pro Asp Ile Gln Asn Lys
1                 5                  10                 15

Ile Glu His Gly Gly Pro Arg Thr Cys Lys Gln Ala Gly Thr Cys Pro
                20                  25                 30

Pro Asp Ile Ile Pro Arg Val Glu Gln Gly Gly Pro Arg Thr Cys Lys
                35                  40                 45

Ala Ala Gly Thr Cys Pro Pro Asp Val Ile Pro Lys Val Glu Gly Gly
                50                  55                 60

Gly Pro Ala Lys Cys Gln Leu Ser Gly Asn Cys Leu Pro Asp Val Lys
65                 70                  75                 80

Asn Lys Val Glu Ala Gly Gly Pro Gln Thr Cys Lys Gln Ala Gly Thr
                85                  90                 95

Cys Pro Pro Asp Val Ile Asn Lys Val Glu Gln Gly Gly Pro Gln Thr
                100                 105                110

Cys Lys Leu Thr Gly Thr Cys Pro Pro Asp Val Ile Pro Lys Val Glu
                115                 120                125

His Gly Gly Pro Arg Gly Cys Lys Ala Ala Gly Thr Cys Pro Pro Asp
                130                 135                140

Val Ile Asn Lys Val Glu His Gly Gly Pro Arg Thr Cys Lys Ala Ser
145                 150                 155                160

Gly Thr Cys Pro Pro Asp Val Ile Pro Lys Val Glu Gly Gly Gly Pro
                165                 170                175
```

-continued

```
Lys Thr Cys Lys Ala Thr Gly Gly Asp Cys Pro Pro Asp Val Ile Lys
                180                 185                 190

Arg Tyr Glu Gln Gly Gly Pro Arg His Cys Lys Ala Thr Gly Asn Cys
            195                 200                 205

Pro Pro Asp Val Glu Asn Lys Ile Glu Gly Gly Pro Lys Thr Cys
        210                 215                 220

Lys Ala Ala Gly Thr Cys Pro Pro Asp Val Ile Pro Lys Ile Glu Gly
225                 230                 235                 240

Gly Gly Pro Ala Lys Cys Gln Leu Ser Gly Asp Cys Leu Pro Asp Val
                245                 250                 255

Lys Asn Lys Val Glu Ala Gly Gly Pro Gln Thr Cys Lys Ala Ala Gly
            260                 265                 270

Thr Cys Pro Ser Asp Val Ile Pro Lys Ile Glu His Gly Gly Pro Ser
        275                 280                 285

Thr Cys Lys Ala Ala Gly Thr Cys Pro Pro Asp Val Val Asn Lys Val
    290                 295                 300

Glu Gly Gly Gly Pro Lys Thr Cys Lys Gln Ser Gly Thr Cys Pro Pro
305                 310                 315                 320

Asp Val Val Pro Lys Val Glu Gly Gly Pro Arg Thr Cys Lys Gln
                325                 330                 335

Ser Gly Thr Cys Pro Pro Asp Val Val Asp Lys Val Glu Gly
            340                 345                 350

<210> SEQ ID NO 42
<211> LENGTH: 232
<212> TYPE: PRT
<213> ORGANISM: Artificial
<220> FEATURE:
<223> OTHER INFORMATION: Trx-cHPVL2.6mer: L2 N-terminal peptides from
      cutaneous HPV genotypes 1a, 2a, 3, 4, 10, and 63 in Pyrococcus
      furiosus thioredoxin

<400> SEQUENCE: 42

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Pro Ser Cys Lys Ile
            20                  25                  30

Ser Asn Thr Cys Pro Pro Asp Ile Gln Asn Lys Ile Glu His Gly Gly
        35                  40                  45

Pro Arg Thr Cys Lys Gln Ala Gly Thr Cys Pro Pro Asp Ile Ile Pro
    50                  55                  60

Arg Val Glu Gln Gly Gly Pro Arg Thr Cys Lys Ala Ala Gly Thr Cys
65                  70                  75                  80

Pro Pro Asp Val Ile Pro Lys Val Glu Gly Gly Pro Ala Lys Cys
                85                  90                  95

Gln Leu Ser Gly Asn Cys Leu Pro Asp Val Lys Asn Lys Val Glu Ala
            100                 105                 110

Gly Gly Pro Arg Thr Cys Lys Ala Ser Gly Thr Cys Pro Pro Asp Val
        115                 120                 125

Ile Pro Lys Val Glu Gly Gly Pro Ala Cys Lys Val Ala Asn
    130                 135                 140

Asn Cys Pro Pro Asp Ile Gln Asn Lys Ile Gln Gly Gly Pro Cys
145                 150                 155                 160

Arg Leu Val Glu Arg Phe Met Thr Glu Leu Ser Glu Tyr Phe Glu Asp
                165                 170                 175

Ile Gln Ile Val His Ile Asn Ala Gly Lys Trp Lys Asn Ile Val Asp
```

```
              180                 185                 190
Lys Phe Asn Ile Leu Asn Val Pro Thr Leu Val Tyr Leu Lys Asp Gly
            195                 200                 205

Arg Glu Val Gly Arg Gln Asn Leu Ile Arg Ser Lys Glu Glu Ile Leu
        210                 215                 220

Lys Lys Leu Lys Glu Leu Gln Glu
225                 230

<210> SEQ ID NO 43
<211> LENGTH: 299
<212> TYPE: PRT
<213> ORGANISM: Artificial
<220> FEATURE:
<223> OTHER INFORMATION: Trx-cHPVL2.9mer: L2 N-terminal peptides from
      cutaneous HPV genotypes 1a, 2a, 3, 4, 10, 41, 63, 88, and 95 in
      Pyrococcus furiosus thioredoxin

<400> SEQUENCE: 43

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Pro Ser Cys Lys Ile
            20                  25                  30

Ser Asn Thr Cys Pro Pro Asp Ile Gln Asn Lys Ile Glu His Gly Gly
        35                  40                  45

Pro Arg Thr Cys Lys Gln Ala Gly Thr Cys Pro Pro Asp Ile Ile Pro
    50                  55                  60

Arg Val Glu Gln Gly Gly Pro Arg Thr Cys Lys Ala Ala Gly Thr Cys
65                  70                  75                  80

Pro Pro Asp Val Ile Pro Lys Val Glu Gly Gly Pro Ala Lys Cys
                85                  90                  95

Gln Leu Ser Gly Asn Cys Leu Pro Asp Val Lys Asn Lys Val Glu Ala
            100                 105                 110

Gly Gly Pro Arg Thr Cys Lys Ala Ser Gly Thr Cys Pro Pro Asp Val
        115                 120                 125

Ile Pro Lys Val Glu Gly Gly Pro Lys Thr Cys Lys Ala Thr Gly
    130                 135                 140

Gly Asp Cys Pro Pro Asp Val Ile Lys Arg Tyr Glu Gln Gly Gly Pro
145                 150                 155                 160

Pro Ala Cys Lys Val Ala Asn Asn Cys Pro Pro Asp Ile Gln Asn Lys
                165                 170                 175

Ile Glu Gln Gly Gly Pro Arg His Cys Lys Ala Thr Gly Asn Cys Pro
            180                 185                 190

Pro Asp Val Glu Asn Lys Ile Glu Gly Gly Pro Ala Lys Cys Gln
        195                 200                 205

Leu Ser Gly Asp Cys Leu Pro Asp Val Lys Asn Lys Val Glu Ala Gly
    210                 215                 220

Gly Pro Cys Arg Leu Val Glu Arg Phe Met Thr Glu Leu Ser Glu Tyr
225                 230                 235                 240

Phe Glu Asp Ile Gln Ile Val His Ile Asn Ala Gly Lys Trp Lys Asn
                245                 250                 255

Ile Val Asp Lys Phe Asn Ile Leu Asn Val Pro Thr Leu Val Tyr Leu
            260                 265                 270

Lys Asp Gly Arg Glu Val Gly Arg Gln Asn Leu Ile Arg Ser Lys Glu
        275                 280                 285

Glu Ile Leu Lys Lys Leu Lys Glu Leu Gln Glu
    290                 295
```

<210> SEQ ID NO 44
<211> LENGTH: 277
<212> TYPE: PRT
<213> ORGANISM: Artificial
<220> FEATURE:
<223> OTHER INFORMATION: Trx-cHPVL2.8mer: L2 N-terminal peptides from cutaneous HPV genotypes 1a, 2a, 3, 4, 5, 6, 41, 88 in Pyrococcus furiosus thioredoxin

<400> SEQUENCE: 44

```
Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Pro Ser Cys Lys Ile
            20                  25                  30

Ser Asn Thr Cys Pro Pro Asp Ile Gln Asn Lys Ile Glu His Gly Gly
        35                  40                  45

Pro Arg Thr Cys Lys Gln Ala Gly Thr Cys Pro Pro Asp Ile Ile Pro
    50                  55                  60

Arg Val Glu Gln Gly Gly Pro Arg Thr Cys Lys Ala Ala Gly Thr Cys
65                  70                  75                  80

Pro Pro Asp Val Ile Pro Lys Val Glu Gly Gly Pro Ala Lys Cys
                85                  90                  95

Gln Leu Ser Gly Asn Cys Leu Pro Asp Val Lys Asn Lys Val Glu Ala
            100                 105                 110

Gly Gly Pro Gln Thr Cys Lys Gln Ala Gly Thr Cys Pro Pro Asp Val
        115                 120                 125

Ile Asn Lys Val Glu Gln Gly Gly Pro Gln Thr Cys Lys Leu Thr Gly
    130                 135                 140

Thr Cys Pro Pro Asp Val Ile Pro Lys Val Glu His Gly Gly Pro Lys
145                 150                 155                 160

Thr Cys Lys Ala Thr Gly Gly Asp Cys Pro Pro Asp Val Ile Lys Arg
                165                 170                 175

Tyr Glu Gln Gly Gly Pro Arg His Cys Lys Ala Thr Gly Asn Cys Pro
            180                 185                 190

Pro Asp Val Glu Asn Lys Ile Glu Gly Gly Pro Cys Arg Leu Val
        195                 200                 205

Glu Arg Phe Met Thr Glu Leu Ser Glu Tyr Phe Glu Asp Ile Gln Ile
    210                 215                 220

Val His Ile Asn Ala Gly Lys Trp Lys Asn Ile Val Asp Lys Phe Asn
225                 230                 235                 240

Ile Leu Asn Val Pro Thr Leu Val Tyr Leu Lys Asp Gly Arg Glu Val
                245                 250                 255

Gly Arg Gln Asn Leu Ile Arg Ser Lys Glu Glu Ile Leu Lys Lys Leu
            260                 265                 270

Lys Glu Leu Gln Glu
        275
```

<210> SEQ ID NO 45
<211> LENGTH: 321
<212> TYPE: PRT
<213> ORGANISM: Artificial
<220> FEATURE:
<223> OTHER INFORMATION: Trx-cHPVL2.10mer: L2 N-terminal peptides from cutaneous HPV genotypes 1a, 2a, 3, 4, 5, 6, 9, 10, 41, 88 in Pyrococcus furiosus thioredoxin

<400> SEQUENCE: 45

```
Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Pro Ser Cys Lys Ile
            20                  25                  30

Ser Asn Thr Cys Pro Pro Asp Ile Gln Asn Lys Ile Glu His Gly Gly
        35                  40                  45

Pro Arg Thr Cys Lys Gln Ala Gly Thr Cys Pro Pro Asp Ile Ile Pro
    50                  55                  60

Arg Val Glu Gln Gly Pro Arg Thr Cys Lys Ala Ala Gly Thr Cys
65                  70                  75                  80

Pro Pro Asp Val Ile Pro Lys Val Glu Gly Gly Pro Ala Lys Cys
                85                  90                  95

Gln Leu Ser Gly Asn Cys Leu Pro Asp Val Lys Asn Lys Val Glu Ala
            100                 105                 110

Gly Gly Pro Gln Thr Cys Lys Gln Ala Gly Thr Cys Pro Pro Asp Val
        115                 120                 125

Ile Asn Lys Val Glu Gln Gly Gly Pro Gln Thr Cys Lys Leu Thr Gly
    130                 135                 140

Thr Cys Pro Pro Asp Val Ile Pro Lys Val Glu His Gly Gly Pro Arg
145                 150                 155                 160

Gly Cys Lys Ala Ala Gly Thr Cys Pro Pro Asp Val Ile Asn Lys Val
                165                 170                 175

Glu His Gly Gly Pro Arg Thr Cys Lys Ala Ser Gly Thr Cys Pro Pro
            180                 185                 190

Asp Val Ile Pro Lys Val Glu Gly Gly Pro Lys Thr Cys Lys Ala
        195                 200                 205

Thr Gly Gly Asp Cys Pro Pro Asp Val Ile Lys Arg Tyr Glu Gln Gly
    210                 215                 220

Gly Pro Arg His Cys Lys Ala Thr Gly Asn Cys Pro Pro Asp Val Glu
225                 230                 235                 240

Asn Lys Ile Glu Gly Gly Pro Cys Arg Leu Val Glu Arg Phe Met
                245                 250                 255

Thr Glu Leu Ser Glu Tyr Phe Glu Asp Ile Gln Ile Val His Ile Asn
            260                 265                 270

Ala Gly Lys Trp Lys Asn Ile Val Asp Lys Phe Asn Ile Leu Asn Val
        275                 280                 285

Pro Thr Leu Val Tyr Leu Lys Asp Gly Arg Glu Val Gly Arg Gln Asn
    290                 295                 300

Leu Ile Arg Ser Lys Glu Glu Ile Leu Lys Lys Leu Lys Glu Leu Gln
305                 310                 315                 320

Glu

<210> SEQ ID NO 46
<211> LENGTH: 365
<212> TYPE: PRT
<213> ORGANISM: Artificial
<220> FEATURE:
<223> OTHER INFORMATION: Trx-cHPVL2.12mer: L2 N-terminal peptides from
      cutaneous HPV genotypes 1a, 2a, 3, 4, 5, 6, 9, 10, 41, 69, 88,
      and 95 in Pyrococcus furiosus thioredoxin

<400> SEQUENCE: 46

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Pro Ser Cys Lys Ile
            20                  25                  30
```

Ser Asn Thr Cys Pro Pro Asp Ile Gln Asn Lys Ile Glu His Gly Gly
        35                  40                  45

Pro Arg Thr Cys Lys Gln Ala Gly Thr Cys Pro Pro Asp Ile Ile Pro
    50                  55                  60

Arg Val Glu Gln Gly Gly Pro Arg Thr Cys Lys Ala Ala Gly Thr Cys
65                  70                  75                  80

Pro Pro Asp Val Ile Pro Lys Val Gly Gly Pro Ala Lys Cys
                85                  90                  95

Gln Leu Ser Gly Asn Cys Leu Pro Asp Val Lys Asn Lys Val Glu Ala
            100                 105                 110

Gly Gly Pro Gln Thr Cys Lys Gln Ala Gly Thr Cys Pro Pro Asp Val
            115                 120                 125

Ile Asn Lys Val Glu Gln Gly Gly Pro Gln Thr Cys Lys Leu Thr Gly
        130                 135                 140

Thr Cys Pro Pro Asp Val Ile Pro Lys Val Glu His Gly Gly Pro Arg
145                 150                 155                 160

Gly Cys Lys Ala Ala Gly Thr Cys Pro Pro Asp Val Ile Asn Lys Val
                165                 170                 175

Glu His Gly Gly Pro Arg Thr Cys Lys Ala Ser Gly Thr Cys Pro Pro
            180                 185                 190

Asp Val Ile Pro Lys Val Glu Gly Gly Pro Lys Thr Cys Lys Ala
        195                 200                 205

Thr Gly Gly Asp Cys Pro Pro Asp Val Ile Lys Arg Tyr Glu Gln Gly
        210                 215                 220

Gly Pro Arg His Cys Lys Ala Thr Gly Asn Cys Pro Pro Asp Val Glu
225                 230                 235                 240

Asn Lys Ile Glu Gly Gly Pro Lys Thr Cys Lys Ala Ala Gly Thr
                245                 250                 255

Cys Pro Pro Asp Val Ile Pro Lys Ile Glu Gly Gly Pro Ala Lys
                260                 265                 270

Cys Gln Leu Ser Gly Asp Cys Leu Pro Asp Val Lys Asn Lys Val Glu
        275                 280                 285

Ala Gly Gly Pro Cys Arg Leu Val Glu Arg Phe Met Thr Glu Leu Ser
        290                 295                 300

Glu Tyr Phe Glu Asp Ile Gln Ile Val His Ile Asn Ala Gly Lys Trp
305                 310                 315                 320

Lys Asn Ile Val Asp Lys Phe Asn Ile Leu Asn Val Pro Thr Leu Val
                325                 330                 335

Tyr Leu Lys Asp Gly Arg Glu Val Gly Arg Gln Asn Leu Ile Arg Ser
            340                 345                 350

Lys Glu Glu Ile Leu Lys Lys Leu Lys Glu Leu Gln Glu
        355                 360                 365

<210> SEQ ID NO 47
<211> LENGTH: 409
<212> TYPE: PRT
<213> ORGANISM: Artificial
<220> FEATURE:
<223> OTHER INFORMATION: Trx-cHPVL2.14mer: L2 N-terminal peptides from
      HPV genotypes 1a, 2a, 3, 4, 5, 6, 9, 10, 31, 41, 51, 69, 88, and
      95 in Pyrococcus furiosus thioredoxin

<400> SEQUENCE: 47

Met Ile Ile Glu Tyr Asp Gly Glu Ile Asp Phe Thr Lys Gly Arg Val
1               5                   10                  15

-continued

```
Val Leu Trp Phe Ser Ile Pro Gly Cys Gly Pro Ser Cys Lys Ile
         20                  25                  30
Ser Asn Thr Cys Pro Pro Asp Ile Gln Asn Lys Ile Glu His Gly Gly
             35                  40                  45
Pro Arg Thr Cys Lys Gln Ala Gly Thr Cys Pro Pro Asp Ile Ile Pro
 50                  55                  60
Arg Val Glu Gln Gly Gly Pro Arg Thr Cys Lys Ala Ala Gly Thr Cys
65                  70                  75                  80
Pro Pro Asp Val Ile Pro Lys Val Glu Gly Gly Pro Ala Lys Cys
             85                  90                  95
Gln Leu Ser Gly Asn Cys Leu Pro Asp Val Lys Asn Lys Val Glu Ala
            100                 105                 110
Gly Gly Pro Gln Thr Cys Lys Gln Ala Gly Thr Cys Pro Pro Asp Val
            115                 120                 125
Ile Asn Lys Val Glu Gln Gly Gly Pro Gln Thr Cys Lys Leu Thr Gly
            130                 135                 140
Thr Cys Pro Pro Asp Val Ile Pro Lys Val Glu His Gly Gly Pro Arg
145                 150                 155                 160
Gly Cys Lys Ala Ala Gly Thr Cys Pro Pro Asp Val Ile Asn Lys Val
                165                 170                 175
Glu His Gly Gly Pro Arg Thr Cys Lys Ala Ser Gly Thr Cys Pro Pro
            180                 185                 190
Asp Val Ile Pro Lys Val Glu Gly Gly Pro Lys Thr Cys Lys Ala
            195                 200                 205
Thr Gly Gly Asp Cys Pro Pro Asp Val Ile Lys Arg Tyr Glu Gln Gly
210                 215                 220
Gly Pro Arg His Cys Lys Ala Thr Gly Asn Cys Pro Pro Asp Val Glu
225                 230                 235                 240
Asn Lys Ile Glu Gly Gly Pro Lys Thr Cys Lys Ala Ala Gly Thr
                245                 250                 255
Cys Pro Pro Asp Val Ile Pro Lys Ile Glu Gly Gly Pro Ala Lys
            260                 265                 270
Cys Gln Leu Ser Gly Asp Cys Leu Pro Asp Val Lys Asn Lys Val Glu
            275                 280                 285
Ala Gly Gly Pro Gln Thr Cys Lys Ala Ala Gly Thr Cys Pro Ser Asp
            290                 295                 300
Val Ile Pro Lys Ile Glu His Gly Gly Pro Ser Thr Cys Lys Ala Ala
305                 310                 315                 320
Gly Thr Cys Pro Pro Asp Val Val Asn Lys Val Glu Gly Gly Pro
                325                 330                 335
Cys Arg Leu Val Glu Arg Phe Met Thr Glu Leu Ser Glu Tyr Phe Glu
            340                 345                 350
Asp Ile Gln Ile Val His Ile Asn Ala Gly Lys Trp Lys Asn Ile Val
            355                 360                 365
Asp Lys Phe Asn Ile Leu Asn Val Pro Thr Leu Val Tyr Leu Lys Asp
            370                 375                 380
Gly Arg Glu Val Gly Arg Gln Asn Leu Ile Arg Ser Lys Glu Ile
385                 390                 395                 400
Leu Lys Lys Leu Lys Glu Leu Gln Glu
                405
```

<210> SEQ ID NO 48
<211> LENGTH: 453
<212> TYPE: PRT

<213> ORGANISM: Artificial
<220> FEATURE:
<223> OTHER INFORMATION: Trx-cHPVL2.16mer: L2 N-terminal peptides from
HPV genotypes 1a, 2a, 3, 4,5, 6, 9, 10, 18, 31, 39, 41, 51, 69,
88, and 95 in Pyrococcus furiosus thioredoxin

<400> SEQUENCE: 48

```
Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Pro Ser Cys Lys Ile
            20                  25                  30

Ser Asn Thr Cys Pro Pro Asp Ile Gln Asn Lys Ile Glu His Gly Gly
        35                  40                  45

Pro Arg Thr Cys Lys Gln Ala Gly Thr Cys Pro Pro Asp Ile Ile Pro
    50                  55                  60

Arg Val Glu Gln Gly Gly Pro Arg Thr Cys Lys Ala Ala Gly Thr Cys
65                  70                  75                  80

Pro Pro Asp Val Ile Pro Lys Val Glu Gly Gly Pro Ala Lys Cys
                85                  90                  95

Gln Leu Ser Gly Asn Cys Leu Pro Asp Val Lys Asn Lys Val Glu Ala
            100                 105                 110

Gly Gly Pro Gln Thr Cys Lys Gln Ala Gly Thr Cys Pro Pro Asp Val
        115                 120                 125

Ile Asn Lys Val Glu Gln Gly Gly Pro Gln Thr Cys Lys Leu Thr Gly
    130                 135                 140

Thr Cys Pro Pro Asp Val Ile Pro Lys Val Glu His Gly Gly Pro Arg
145                 150                 155                 160

Gly Cys Lys Ala Ala Gly Thr Cys Pro Pro Asp Val Ile Asn Lys Val
                165                 170                 175

Glu His Gly Gly Pro Arg Thr Cys Lys Ala Ser Gly Thr Cys Pro Pro
            180                 185                 190

Asp Val Ile Pro Lys Val Glu Gly Gly Pro Lys Thr Cys Lys Ala
        195                 200                 205

Thr Gly Gly Asp Cys Pro Pro Asp Val Ile Lys Arg Tyr Glu Gln Gly
210                 215                 220

Gly Pro Arg His Cys Lys Ala Thr Gly Asn Cys Pro Pro Asp Val Glu
225                 230                 235                 240

Asn Lys Ile Glu Gly Gly Pro Lys Thr Cys Lys Ala Ala Gly Thr
            245                 250                 255

Cys Pro Pro Asp Val Ile Pro Lys Ile Glu Gly Gly Pro Ala Lys
        260                 265                 270

Cys Gln Leu Ser Gly Asp Cys Leu Pro Asp Val Lys Asn Lys Val Glu
    275                 280                 285

Ala Gly Gly Pro Gln Thr Cys Lys Ala Ala Gly Thr Cys Pro Ser Asp
290                 295                 300

Val Ile Pro Lys Ile Glu His Gly Gly Pro Ser Thr Cys Lys Ala Ala
305                 310                 315                 320

Gly Thr Cys Pro Pro Asp Val Val Asn Lys Val Glu Gly Gly Gly Pro
                325                 330                 335

Lys Thr Cys Lys Gln Ser Gly Thr Cys Pro Pro Asp Val Pro Lys
            340                 345                 350

Val Glu Gly Gly Gly Pro Arg Thr Cys Lys Gln Ser Gly Thr Cys Pro
        355                 360                 365

Pro Asp Val Val Asp Lys Val Glu Gly Gly Gly Pro Cys Arg Leu Val
    370                 375                 380
```

```
Glu Arg Phe Met Thr Glu Leu Ser Glu Tyr Phe Asp Ile Gln Ile
385                 390                 395                 400

Val His Ile Asn Ala Gly Lys Trp Lys Asn Ile Val Asp Lys Phe Asn
                405                 410                 415

Ile Leu Asn Val Pro Thr Leu Val Tyr Leu Lys Asp Gly Arg Glu Val
            420                 425                 430

Gly Arg Gln Asn Leu Ile Arg Ser Lys Glu Glu Ile Leu Lys Lys Leu
        435                 440                 445

Lys Glu Leu Gln Glu
    450
```

<210> SEQ ID NO 49
<211> LENGTH: 109
<212> TYPE: PRT
<213> ORGANISM: Escherichia coli

<400> SEQUENCE: 49

```
Met Gly Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105
```

<210> SEQ ID NO 50
<211> LENGTH: 138
<212> TYPE: PRT
<213> ORGANISM: Methanosaeta thermophila

<400> SEQUENCE: 50

```
Met Asp Glu Leu Asp Glu Ile Arg Arg Lys Leu Glu Glu Leu Lys
1               5                   10                  15

Arg Glu Leu Ala Ala Arg Ser Gln Gly Thr Pro Thr Ile Glu Tyr Pro
            20                  25                  30

Asp Arg Pro Val Leu Val Thr Asp Ser Ser Ile Asp Ala Gly Ile Arg
        35                  40                  45

Gln Tyr Pro Val Phe Val Val Asp Cys Trp Ala Glu Trp Cys Gly Pro
    50                  55                  60

Cys Arg Ala Ile Ala Pro Val Ile Asp Glu Met Ala Arg Glu Leu Lys
65                  70                  75                  80

Gly Arg Val Val Phe Gly Lys Leu Asn Val Asp Gln Asn Pro Leu Thr
                85                  90                  95

Ser Arg Lys Tyr Gly Ile Thr Ala Ile Pro Thr Leu Val Phe Arg
            100                 105                 110

Asn Gly Arg Leu Val Asp Arg Leu Val Gly Ala Tyr Pro Lys Gln Ile
        115                 120                 125

Leu Met Ser Arg Val Arg Lys Tyr Leu Asp
    130                 135
```

<210> SEQ ID NO 51
<211> LENGTH: 100
<212> TYPE: PRT
<213> ORGANISM: Pyrococcus furiosus

<400> SEQUENCE: 51

```
Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Cys Arg Leu Val Glu
            20                  25                  30

Arg Phe Met Thr Glu Leu Ser Glu Tyr Phe Glu Asp Ile Gln Ile Val
        35                  40                  45

His Ile Asn Ala Gly Lys Trp Lys Asn Ile Val Asp Lys Phe Asn Ile
    50                  55                  60

Leu Asn Val Pro Thr Leu Val Tyr Leu Lys Asp Gly Arg Glu Val Gly
65                  70                  75                  80

Arg Gln Asn Leu Ile Arg Ser Lys Glu Glu Ile Leu Lys Lys Leu Lys
                85                  90                  95

Glu Leu Gln Glu
            100
```

<210> SEQ ID NO 52
<211> LENGTH: 330
<212> TYPE: DNA
<213> ORGANISM: Escherichia coli

<400> SEQUENCE: 52

```
atgggcgata aaattattca cctgactgac gacagttttg acacggatgt actcaaagcg      60
gacggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggcgtga                                     330
```

<210> SEQ ID NO 53
<211> LENGTH: 417
<212> TYPE: DNA
<213> ORGANISM: Methanosaeta thermophila

<400> SEQUENCE: 53

```
atggacgagc tggacgaaat ccgccgtaaa aaactggaag aactgaaacg tgaactggct      60
gcccgtagtc aaggaacacc gacgatcgag tatcctgacc gccctgtact ggttactgat     120
tctagcattg atgccgggat ccgccaatat cctgtctttg tggtggactg ttgggctgaa     180
tggtgcggtc cgtgtcgtgc tattgctccg gtgatcgatg aaatggcccg tgagctgaaa     240
ggacgtgtgg tattcgggaa actgaacgtg gaccaaaatc cgctgacgag tcgtaaatat     300
ggcattaccg ccatccctac actgctggtt ttccgtaacg tcgtctggt tgatcgcctg     360
gttggtgctt atccgaaaca aattctgatg tctcgtgtcc gtaaatatct ggactag       417
```

<210> SEQ ID NO 54
<211> LENGTH: 303
<212> TYPE: DNA
<213> ORGANISM: Pyrococcus furiosus

<400> SEQUENCE: 54

```
atgattatcg agtatgacgg cgaaatcgac ttcaccaaag gtcgtgttgt actgtggttt      60
agcattccgg gatgcggtcc gtgtcgtctg gttgaacgct tcatgaccga actgagcgag     120
tattttgagg atatccaaat tgtccatatc aatgccggca atggaaaaaa catcgtagac     180
aaattcaata ttctgaacgt gccgaccctg gtatatctga agatggccg tgaggttgga     240 cgccaaaacc tgattcgttc taaagaagag attctgaaaa aactgaaaga gctgcaggag     300
taa                                                                   303
```

<210> SEQ ID NO 55
<211> LENGTH: 55
<212> TYPE: PRT
<213> ORGANISM: Artificial
<220> FEATURE:
<223> OTHER INFORMATION: IMX313T

<400> SEQUENCE: 55

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Gly Arg Arg Arg Arg Arg Ser
    50                  55

<210> SEQ ID NO 56
<211> LENGTH: 13
<212> TYPE: PRT
<213> ORGANISM: Artificial
<220> FEATURE:
<223> OTHER INFORMATION: Pan HLA-DR reactive epitope (PADRE)

<400> SEQUENCE: 56

Ala Lys Phe Val Ala Ala Trp Thr Leu Lys Ala Ala Ala
1               5                   10

<210> SEQ ID NO 57
<211> LENGTH: 3
<212> TYPE: PRT
<213> ORGANISM: Artificial
<220> FEATURE:
<223> OTHER INFORMATION: GGP linker

<400> SEQUENCE: 57

Gly Gly Pro
1

<210> SEQ ID NO 58
<211> LENGTH: 4
<212> TYPE: PRT
<213> ORGANISM: Artificial
<220> FEATURE:
<223> OTHER INFORMATION: GPGP linker

<400> SEQUENCE: 58

Gly Pro Gly Pro
1

<210> SEQ ID NO 59
<211> LENGTH: 5
<212> TYPE: PRT
<213> ORGANISM: Artificial

```
<220> FEATURE:
<223> OTHER INFORMATION: GPGPG linker

<400> SEQUENCE: 59

Gly Pro Gly Pro Gly
1               5

<210> SEQ ID NO 60
<211> LENGTH: 4
<212> TYPE: PRT
<213> ORGANISM: Artificial
<220> FEATURE:
<223> OTHER INFORMATION: SGSG linker

<400> SEQUENCE: 60

Ser Gly Ser Gly
1

<210> SEQ ID NO 61
<211> LENGTH: 699
<212> TYPE: DNA
<213> ORGANISM: Artificial
<220> FEATURE:
<223> OTHER INFORMATION: Trx-cHPL2.6mer encoding sequence, optimized for
      E. coli codon usage

<400> SEQUENCE: 61
atgattatcg agtatgatgg cgagattgac ttcaccaaag gtcgcgtcgt actgtggttt      60
agcattcccg gttgcggtcc gccgtcctgc aaaatctcga cacctgtcc gccagatatc     120 cagaacaaaa tcgagcatgg cggtcctcgc acctgtaaac aagcaggcac ctgtccaccc     180
gacatcattc cgcgtgtaga gcaaggtggc cctcgcacgt gcaaagcagc gggtacttgc     240
ccgccagatg tgattccgaa agttgaaggc ggtggtcccg cgaaatgcca gttaagcggg     300
aattgtctgc cggatgtgaa gaacaaggtc gaagctggag ccccgcgtac gtgcaaagcg     360
agtggcacat gtccaccgga tgtcattccc aaagtggaag cggcggaccc tccgcctgc    420 aaagttgcca ataattgccc gcctgacatt cagaacaaga ttgaacaggg cggtccgtgc     480
cgtcttgtgg aacggtttat gaccgagtta tccgaatact tcgaggacat tcagatcgtg     540
cacattaatg cgggcaaatg gaagaacatc gttgacaaat tcaacatcct caatgtccct     600
accctggttt acctcaaaga tggtcgcgaa gttgggcgcc agaacttgat tcgcagcaaa     660
gaagagattc tgaagaaact gaaagaattg caagaataa                           699

<210> SEQ ID NO 62
<211> LENGTH: 900
<212> TYPE: DNA
<213> ORGANISM: Artificial
<220> FEATURE:
<223> OTHER INFORMATION: Trx-cHPVL2.9mer encoding sequence, optimized
      for E. coli codon usage

<400> SEQUENCE: 62
atgattatcg agtatgatgg cgagattgac ttcaccaaag gtcgcgtcgt actgtggttt      60
agcattcccg gttgcggtcc gccgtcctgc aaaatctcga ataccctgtcc accggacatc    120 cagaacaaaa tcgagcatgg tggcccacgt acctgtaaac aggcgggaac ttgtcctccg     180
gacattattc cgcgcgtaga gcaaggtggc ccgcgtacgt gcaaagcggc tgggacctgt     240
ccgccggatg tgattccgaa agttgaaggc ggaggtcccg ctaaatgcca actgtctggg     300
aactgcttac cggatgtcaa gaacaaagtc gaagcgggtg cccgcgcac atgcaaagcc      360
```

| | |
|---|---|
| agtggtacgt gcccaccgga tgtaattccc aaagtggaag gtggcgggcc caagacgtgt | 420 |
| aaagcaactg gcggggattg cccgcctgat gtcatcaaac gctatgaaca gggtggccct | 480 |
| cccgcatgca agttgccaa taattgcccg cctgacattc agaacaagat tgaacaaggc | 540 |
| ggtccacggc actgtaaagc aaccggtaat tgtccgccag acgtggagaa caaaatcgaa | 600 |
| ggcggtgggc cagcgaaatg ccagttgagc ggcgattgtc tgccggatgt gaagaacaag | 660 |
| gttgaagccg gcggtccgtg ccgtcttgtg aacggtttta tgaccgagtt atccgaatac | 720 |
| ttcgaggaca ttcagatcgt gcacattaat gcgggcaaat ggaagaacat cgttgacaaa | 780 |
| ttcaacatcc tcaatgtccc taccctggtt tacctcaaag atggtcgcga agttgggcgc | 840 |
| cagaacttga ttcgcagcaa agaagagatt ctgaagaaac tgaaagaatt gcaagaataa | 900 |

<210> SEQ ID NO 63
<211> LENGTH: 834
<212> TYPE: DNA
<213> ORGANISM: Artificial
<220> FEATURE:
<223> OTHER INFORMATION: Trx-cHPVL2.8mer encoding sequence, optimized
      for E. coli codon usage

<400> SEQUENCE: 63

| | |
|---|---|
| atgatcatcg agtatgacgg cgagattgac ttcaccaagg gacgcgtcgt gctttggttc | 60 |
| agcatcccg gttgcggccc cccaagctgc aagatttcaa acacatgtcc gccggatatc | 120 |
| cagaacaaga ttgaacacgg cggcccacgc acttgcaaac aggccgggac ctgtccgccc | 180 |
| gacattatcc cgcgcgtcga gcaaggagga cctcgtactt gcaaagctgc cggaaccctgt | 240 |
| ccgcccgacg taatccctaa ggttgagggc ggaggaccgg ccaaatgtca gttgtctggt | 300 |
| aactgcttac cggacgtaaa gaacaaggtt gaagccggtg acccaaaac gtgcaaacaa | 360 |
| gctggtaccct gtccgcccga cgttatcaat aaggtagagc aaggtgggcc tcaaacgtgt | 420 |
| aagttgacag gtacttgccc gcctgacgtg attcctaaag tagagcacgg tgggcccaag | 480 |
| acctgcaaag cgacaggagg tgactgcccc cctgatgtca tcaaacgcta tgagcagggg | 540 |
| ggacctcgtc actgcaaagc aaccgggaac tgcccaccgg acgtcgagaa caagattgag | 600 |
| ggaggtgggc catgtcgctt ggtcgagcgt tttatgactg agcttctga atatttcgag | 660 |
| gatattcaaa ttgtccacat taacgctggt aagtggaaaa acattgttga caaatttaac | 720 |
| atccttaacg tgcccacact tgtgtacctt aaagatgggc gtgaggtggg tcgtcagaat | 780 |
| cttatccgtt caaaagagga aatcttgaag aaactgaaag gcttcagga ataa | 834 |

<210> SEQ ID NO 64
<211> LENGTH: 966
<212> TYPE: DNA
<213> ORGANISM: Artificial
<220> FEATURE:
<223> OTHER INFORMATION: Trx-cHPVL2.10mer encoding sequence, optimized
      for E. coli codon usage

<400> SEQUENCE: 64

| | |
|---|---|
| atgattattg aatacgacgg tgagatcgat tttaccaaag gccgcgtagt attgtggttt | 60 |
| agcattccag gctgcggccc gccgtcgtgc aaaattagta cacttgtcc acccgatatt | 120 |
| caaaacaaaa ttgaacatgg aggaccccgt acatgcaaac aagcaggcac gtgccccct | 180 |
| gatattattc ctcgtgtaga gcaaggaggg cctcgtacgt gcaaagcagc aggtacatgc | 240 |
| ccaccagatg tcatccctaa ggtcgagggt ggcggtccgg caaagtgtca gctgtctggt | 300 |
| aattgtctgc cggatgtgaa gaataaggta gaggcgggtg gtccccaaac ctgtaagcag | 360 |

```
gctgggacct gcccaccgga cgtaatcaac aaggtcgagc aagggggccc tcagacttgc    420
aagcttacag ggacatgccc gccagacgta atccctaaag ttgaacacgg tgggcctcgc    480
ggatgtaaag ccgccgggac ttgtccacca gacgtaatta acaaagtgga gcatggtgga    540
ccccgtacat gtaaggcgtc aggcacgtgc ccaccgacg ttatcccgaa agttgaaggc     600
ggaggtccga aaacgtgtaa agctacaggt ggagattgcc caccggacgt aatcaagcgc    660
tatgaacagg gtgggccccg tcactgtaaa gcaactggga actgccctcc cgacgtggaa    720
aataagattg aaggtggagg cccgtgccgc ttagtcgagc gcttcatgac cgagctgtca    780
gagtactttg aggacattca gattgtccac atcaacgcag aaaatggaa aaacatcgtt     840 gacaagttta acattcttaa tgtccccaca ttagtgtatc ttaaagatgg ccgtgaagtt    900
ggacgccaaa acttaattcg ctcgaaggag gaaatcttga gaagttaaa agaattgcaa     960 gaataa                                                               966
```

<210> SEQ ID NO 65
<211> LENGTH: 1098
<212> TYPE: DNA
<213> ORGANISM: Artificial
<220> FEATURE:
<223> OTHER INFORMATION: Trx-cHPVL2.12mer encoding sequence, optimized
      for E. coli codon usage

<400> SEQUENCE: 65

```
atgattatcg aatatgacgg agaaatcgat ttcactaagg gacgtgttgt gctttggttc    60
tctattcccg gctgcggacc gcccagttgt aaaatctcga atacctgccc tccagacatc   120
cagaataaga tcgagcatgg cggtcctcgc acatgcaaac aagcgggaac ctgtccccca   180
gacatcatcc cccgcgtaga acaaggtgga ccgcgcacgt gtaaggctgc tggcaccgt    240 cctccagacg tgattccgaa ggtcgagggt ggcggacccg ctaagtgtca actttcaggg   300
aactgcctgc ccgatgttaa gaataaagtg gaggcgggag gccgcagac ctgtaagcag    360 gcggggacat gtcctcctga tgttattaac aaggtagagc aggggggccc acaaacatgt   420
aaactgactg gaacgtgccc gcccgacgtt attccgaaag tagagcatgg cggccctcgt   480
ggctgcaaag ctgccggcac gtgcccgccg gatgttatca caaagtgga acatggtggt    540 cctcgtactt gtaaggcatc cgggacttgt ccgccagatg tgatcccgaa ggtcgaaggt   600
ggggggccaa agacctgcaa agcgacagga ggggactgtc cgcctgatgt catcaaacgt   660
tatgagcaag gaggccccg ccactgcaag gccactggga actgtccacc ggatgtcgag    720
aacaagatcg agggaggcgg cccgaagacg tgtaaggccg caggtacgtg cccccccagat  780 gtcatcccaa agattgaagg cggaggtcca gcgaaatgcc agttatcggg agactgtctt   840
ccagatgtaa agaacaaggt ggaagcaggt ggaccgtgcc gccttgtcga acgtttcatg   900
accgagttga gcaatatttt tgaagatatt caaattgtgc acatcaatgc aggaaagtgg   960
aaaaatatcg tggataagtt caacattttg aacgtcccca ctcttgtgta ccttaaggat  1020
ggtcgcgaag tcggacgcca gaatcttatt cgctcaaaag aagaaatttt gaaaaagtta  1080
aaagaattgc aagagtaa                                                1098
```

<210> SEQ ID NO 66
<211> LENGTH: 1230
<212> TYPE: DNA
<213> ORGANISM: Artificial
<220> FEATURE:
<223> OTHER INFORMATION: Trx-cHPVL2.14mer encoding sequence, optimized for E. coli codon usage

<400> SEQUENCE: 66

```
atgattatcg agtacgatgg tgagatcgac tttaccaaag gcgtgttgt tctgtggttc      60
tcgatccctg gctgtgggcc gccatcatgc aaaatctcca atacctgccc accagatatt    120
cagaataaaa tcgaacatgg aggccctcgc acatgtaaac aagcaggaac ctgcccgcca    180
gatatcattc ctcgtgttga acaagggggg ccacgtactt gtaaagcagc cggaacttgc    240
cctcccgatg taattcctaa agtggaaggt ggggcccctg caaaatgtca gcttagcggc    300
aactgcttac ctgacgtgaa aaataaagtg gaagccggag gcctcagac ctgcaaacag     360
gcgggcacgt gcccccctga tgtgatcaat aaagtcgagc aaggcggtcc acagacgtgc    420
aaattgactg gcacgtgtcc accagatgta atcccgaagg tagaacatgg agggcctcgc    480
ggatgcaaag ctgctggaac ttgtcccccg acgtaatta ataaggttga acatggcggt     540
ccccgtacat gtaaggcgtc cgggacttgt ccaccagacg tgatcccgaa agtagaagga    600
gggggaccaa aaacgtgtaa agctaccgga ggagattgtc cgcctgacgt tatcaaacgt    660
tacgagcagg gggtccccg ccattgcaag gcgactggca actgcccgcc ggacgttgag     720
aacaaaatcg agggtggcgg accaaagaca tgtaaggcag cgggcacctg cccacccgat    780
gtcattccaa aaatcgaggg cggaggacct gccaagtgcc agcttagtgg cgattgtctg    840
ccggacgtta aaacaaagt ggaagcgggt gggccacaaa catgcaaggc agcaggtact     900
tgtccgtccg atgtcatccc aaagattgag cacggcggcc catcgacctg taaagcggcc    960
gggacctgcc ctccagacgt agttaataag gtagaggggg gcggtccgtg tcgcttggtg   1020
gagcgtttca tgacggagtt atcggagtat tttgaagata ttcaaatcgt ccacatcaat   1080
gctggtaagt ggaagaacat tgtggataaa tttaacatcc ttaatgttcc tacacttgtc   1140
tacttgaagg acggacgtga agtcggtcgt cagaacttaa ttcgctcaaa ggaggagatt   1200
ttgaaaaagt gaaggagtt acaggagtaa                                     1230
```

<210> SEQ ID NO 67
<211> LENGTH: 1362
<212> TYPE: DNA
<213> ORGANISM: Artificial
<220> FEATURE:
<223> OTHER INFORMATION: Trx-cHPVL2.16mer encoding sequence, optimized for E. coli codon usage

<400> SEQUENCE: 67

```
atgatcattg agtatgacgg tgaaattgac ttcactaaag gccgtgtcgt gctttggttt     60
tcaatccctg gttgtggtcc tccgtcgtgt aagatttcta acacgtgtcc tccggatatc    120
caaaacaaga ttgaacacgg tgggccacgt acctgcaaac aagcgggtac gtgtccccc     180
gacattatcc ctcgtgttga gcaggggggc ccgcgcacgt gcaaagccgc cggcacctgc    240
ccgcctgacg taatccccaa agtggagggc ggtggaccgg ccaaatgtca gctgagtggg    300
aattgccttc ctgatgtaaa gaataaagtc gaggccggag gaccccagac ttgcaagcaa    360
gcggggacct gtccccccaga cgtgattaat aaagtggaac agggtgggcc tcagacttgt    420
aaattaactg gcacctgccc cccagacgta attccgaaag tagagcacgg gggcccacgt    480
ggctgtaagg ccgcagggac atgtccgccg acgttatca acaaggtaga acatggggg      540
ccacgcacgt gcaaggcttc cggaacctgc ccccctgatg taattcctaa ggttgagggc    600
ggcggtccaa agacctgtaa ggctaccggc ggggactgcc ccccggacgt gattaagcgt    660
```

```
tacgaacagg gaggccctcg tcactgtaaa gcgacaggaa attgtccgcc agacgtggaa      720
aacaaaatcg aaggaggggg cccaaagact tgcaaagcag ctggtacatg tccccctgac      780
gtcatcccca agatcgaagg tggaggtccc gcgaaatgcc aattatctgg agattgcctg      840
cctgatgtga aaaacaaagt ggaggcggga ggcccccaga cttgcaaagc ggctggcact      900
tgtccatcgg acgtcatccc caaaattgag catggagggc cgtcgacgtg taaggcagct      960
gggacatgcc caccagatgt agtcaacaaa gtcgagggtg gtggaccaaa aacgtgtaaa     1020
cagagcggca cttgtccacc ggatgttgtg cctaaagtgg aaggggggg cccacgcacg      1080 tgtaaacaat cgggcacctg ccctccagac gtggtcgaca aagtcgaggg aggggggccg     1140
tgccgtttag tggagcgctt catgactgag ttgtcagaat attttgaaga tatccagatt     1200
gtgcacatca atgctgggaa gtggaaaaac attgttgaca agtttaacat ccttaatgta     1260 cctaccttg tctatcttaa agatgggcgc gaagtaggtc gtcaaaacct gatccgctcc      1320
aaagaagaga ttcttaaaaa gttgaaagaa ttgcaggaat aa                        1362
```